(12) United States Patent
Noguera-Troise et al.

(10) Patent No.: US 8,048,418 B2
(45) Date of Patent: Nov. 1, 2011

(54) THERAPEUTIC METHODS FOR INHIBITING TUMOR GROWTH WITH COMBINATION OF DLL4 ANTAGONISTS AND VEGF ANTAGONISTS

(75) Inventors: Irene Noguera-Troise, Bay Shore, NY (US); Gavin Thurston, White Plains, NY (US); Nicholas Gale, Yorktown Heights, NY (US); Eric Smith, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/435,030

(22) Filed: May 4, 2009

(65) Prior Publication Data

US 2009/0246199 A1 Oct. 1, 2009

Related U.S. Application Data

(63) Continuation-in-part of application No. 11/264,243, filed on Oct. 31, 2005, now abandoned, application No. 12/435,030, which is a continuation-in-part of application No. 11/639,894, filed on Dec. 15, 2006, now abandoned.

(60) Provisional application No. 60/623,658, filed on Oct. 29, 2004, provisional application No. 60/751,173, filed on Dec. 16, 2005, provisional application No. 60/771,276, filed on Feb. 8, 2006, provisional application No. 60/788,456, filed on Mar. 31, 2006, provisional application No. 60/830,543, filed on Jul. 12, 2006.

(51) Int. Cl.
A61K 39/395 (2006.01)
A61K 38/16 (2006.01)

(52) U.S. Cl. ............... 424/134.1; 424/174.1; 514/8.1; 514/19.3; 530/387.3

(58) Field of Classification Search ............ None
See application file for complete search history.

(56) References Cited

U.S. PATENT DOCUMENTS

| | | | |
|---|---|---|---|
| 6,121,045 A | 9/2000 | McCarthy et al. | |
| 6,379,925 B1 | 4/2002 | Kitajewski et al. | |
| 6,664,098 B1 | 12/2003 | Sakano | |
| 6,984,522 B2 | 1/2006 | Clark et al. | |
| 7,022,499 B2 | 4/2006 | Sakano | |
| 7,087,411 B2 | 8/2006 | Daly et al. | |
| 2006/0030694 A1 | 2/2006 | Kitajewski et al. | |
| 2006/0122373 A1 | 6/2006 | McCarthy et al. | |
| 2007/0213266 A1 | 9/2007 | Gill et al. | |
| 2008/0014196 A1 | 1/2008 | Yan | |
| 2008/0175847 A1 | 7/2008 | Yan et al. | |

FOREIGN PATENT DOCUMENTS

| | | |
|---|---|---|
| EP | 1004669 A1 | 5/2000 |
| WO | WO98/45434 A1 | 10/1998 |
| WO | WO03/042246 A2 | 5/2003 |
| WO | WO03/050502 A2 | 6/2003 |

OTHER PUBLICATIONS

Duarte, A., et al. (2004) Dosage-sensitive requirement for mouse Dll4 in artery development. Gene & Dev. 18: doi: 10.1101/gad.1239004.

Gale, N.W. et al. (2004) Haploinsufficiency of delta-like 4 ligand results in embryonic lethality due to major defects in arterial and vascular development. Proc. Natl. Acad. Sci. USA. 101(45):15949-15954.

Krebs, L.T., et al. (2004) Haploinsufficient lethality and formation of arteriovenous malformations in Notch pathway mutants. Gene & Dev. 18: doi: 10.1101/gad.1239204.

Liu, Z-J., et al. (2003) Regulation of Notch1 and Dll4 by Vascular Endothelial Growth Factor in Arterial Endothelial Cells: Implications for Modulating Arteriogenesis and Angiogenesis. Mo. Cell. Bio. 23(1):14-25.

Mailhos, C., et al. (2001) Delta4, an endothelial specific Notch ligand expressed at sites of physiological and tumor angiogenesis. Differentiation. 69(2-3):135-144.

Noguera I. et al. (2005) Expression of Delta-like 4 (Dll4) ligand in mouse tumor models. Proceedings of the Annual Meeting of the American Association for Cancer Research 46(Suppl S):1104.

Patel, N.S. et al. (2005) Up-regulation of Delta-like 4 Ligand in Human Tumor Vasculature and the Role of Basal Expression in Endothelial Cell Function. Cancer Research 65(19):8690-8697.

Shutter, J.R., et al. (2000) Dll4, a novel Notch ligand expressed in arterial endothelium. Gene & Dev. 14:1313-1318.

*Primary Examiner* — Robert Landsman
*Assistant Examiner* — Ian Dang
(74) *Attorney, Agent, or Firm* — Valeta Gregg, Esq.; Izumi Yokoyama, Esq.

(57) ABSTRACT

Disclosed is a therapeutic method for inhibiting development or growth of tumors that are resistant to the blockade of delta-like ligand 4 (Dll4), or vascular endothelial growth factor (VEGF), or to other therapeutic agents, by administering the combination of Dll4 antagonist and VEGF antagonist. The combined administration of these two agents, concurrently or sequentially, exhibits synergistic effects on blood vessel development and growth, thereby more effectively inhibiting the tumor growth than an administration of either agent alone. The Dll4 antagonist can be an anti-Dll4 antibody or antibody fragment capable of inhibiting the binding of Dll4 to a Notch receptor, or a fusion protein comprising the extracellular domain of Dll4 or a soluble Notch receptor, or a fragment thereof, fused to a multimerizing component. The VEGF antagonist can be a VEGF trap, anti-VEGF antibody or antibody fragment capable of inhibiting the binding of VEGF to a VEGF receptor.

6 Claims, 7 Drawing Sheets

Human HT1080 Sarcoma Xenograft Model

A673-Rhabdomyosarcoma-human

SEQUENCE LISTING

<160> NUMBER OF SEQ ID NOS: 30

<210> SEQ ID NO 1
<211> LENGTH: 2058
<212> TYPE: DNA
<213> ORGANISM: Homo sapiens

<400> SEQUENCE: 1

```
atggcggcag cgtcccggag cgcctctggc tgggcgctac tgctgctggt ggcactttgg      60
cagcagcgcg cggccggctc cggcgtcttc cagctgcagc tgcaggagtt catcaacgag     120
cgcggcgtac tggccagtgg gcggccttgc gagcccggct gccggacttt cttccgcgtc     180
tgccttaagc acttccaggc ggtcgtctcg cccggaccct gcaccttcgg gaccgtctcc     240
acgccggtat tgggcaccaa ctccttcgct gtccgggaca cagtagcgg cgggggcgc     300 aaccctctcc aactgcccct caatttcacc tggccgggta ccttctcgct catcatcgaa     360
gcttggcacg cgccaggaga cgacctgcgg ccagaggcct gccaccaga tgcactcatc     420 agcaagatcg ccatccaggg ctccctagct gtgggtcaga actggttatt ggatgagcaa     480
accagcaccc tcacaaggct gcgctactct taccgggtca tctgcagtga caactactat     540
ggagacaact gctcccgcct gtgcaagaag cgcaatgacc acttcggcca ctatgtgtgc     600
cagccagatg gcaacttgtc ctgcctgccc ggttggactg ggaatattg ccaacagcct     660 atctgtcttt cgggctgtca tgaacagaat ggctactgca gcaagccagc agagtgcctc     720
tgccgcccag ctggcagggg ccggctgtgt aacgaatgca tcccccacaa tggctgtcgc     780
cacggcacct gcagcactcc ctggcaatgt acttgtgatg agggctgggg aggcctgttt     840
tgtgaccaag atctcaacta ctgcacccac cactccccat gcaagaatgg ggcaacgtgc     900
tccaacagtg ggcagcgaag ctacacctgc acctgtcgcc caggctacac tggtgtggac     960
tgtgagctga gctcagcga gtgtgacagc aaccctgtc gcaatggagg cagctgtaag    1020
gaccaggagg atggctacca ctgcctgtgt cctccgggct actatggcct gcattgtgaa    1080
cacagcacct tgagctgcgc cgactccccc tgcttcaatg gggctcctg ccgggagcgc    1140 aaccagggg ccaactatgc ttgtgaatgt ccccccaact tcaccggctc caactgcgag    1200
aagaaagtgg acaggtgcac cagcaacccc tgtgccaacg ggggacagtg cctgaaccga    1260
ggtccaagcc gcatgtgccg ctgccgtcct ggattcacgg gcacctactg tgaactccac    1320
gtcagcgact gtgcccgtaa cccttgcgcc cacggtggca cttgccatga cctggagaat    1380
gggctcatgt gcacctgccc tgccggcttc tctggccgac gctgtgaggt gcggacatcc    1440
atcgatgcct gtgcctcgag tccctgcttc aacagggcca cctgctacac cgacctctcc    1500
acagacacct ttgtgtgcaa ctgcccttat ggctttgtgg gcagccgctg cgagttcccc    1560
gtgggcttgc cgcccagctt cccctgggtg ccgtctcgc tgggtgtggg gctggcagtg    1620
ctgctggtac tgctgggcat ggtggcagtg gctgtgcggc agctgcggct tcgacggccg    1680
gacgacggca gcagggaagc catgaacaac ttgtcggact ccagaagga caacctgatt    1740 cctgccgccc agcttaaaaa cacaaaccag aagaaggagc tggaagtgga ctgtggcctg    1800
gacaagtcca actgtggcaa acagcaaaac cacacattgg actataatct ggccccaggg    1860
cccctggggc gggggaccat gccaggaaag tttcccccaca gtgacaagag cttaggagag    1920
```

```
aaggcgccac tgcggttaca cagtgaaaag ccagagtgtc ggatatcagc gatatgctcc    1980
cccagggact ccatgtacca gtctgtgtgt ttgatatcag aggagaggaa tgaatgtgtc    2040
attgccacgg aggtataa                                                   2058
```

```
<210> SEQ ID NO 2
<211> LENGTH: 685
<212> TYPE: PRT
<213> ORGANISM: Homo sapiens

<400> SEQUENCE: 2
```

```
Met Ala Ala Ser Arg Ser Ala Ser Gly Trp Ala Leu Leu Leu
 1               5                  10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350
```

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 3
<211> LENGTH: 3427
<212> TYPE: DNA
<213> ORGANISM: Mus musculus

<400> SEQUENCE: 3
ctcgcaggct aggaacccga ggccaagagc tgcagccaaa gtcacttggg tgcagtgtac     60
tccctcacta gcccgctcga gaccctagga tttgctccag acacgtact tagagcagcc    120 accgcccagt cgccctcacc tggattacct accgaggcat cgagcagcgg agtttttgag    180
aaggcgacaa gggagcagcg tcccgagggg aatcagcttt tcaggaactc ggctggcaga    240

-continued

```
cgggacttgc gggagagcga catccctaac aagcagattc ggagtcccgg agtggagagg    300
acaccccaag ggatgacgcc tgcgtccdgg agcgcctgtc gctgggcgct actgctgctg    360
gcggtactgt ggccgcagca gcgcgctgcg ggctccggca tcttccagct gcggctgcag    420
gagttcgtca accagcgcgg tatgctggcc aatgggcagt cctgcgaacc gggctgccgg    480
actttcttcc gcatttgcct taagcacttc caggcaacct tctccgaggg accctgcacc    540
tttggcaatg tctccacgcc ggtattgggc accaactcct tcgtcgtcag ggacaagaat    600
agcggcagtg gtcgcaaccc tctgcagttg cccttcaatt tcacctggcc gggaaccttc    660
tcactcaaca tccaagcttg gcacacaccg ggagacgacc tgcggccaga gcttcgcca    720 ggaaactctc tcatcagcca aatcatcatc caaggctctc ttgctgtggg taagatttgg    780
cgaacagacg agcaaaatga caccctcacc agactgagct actcttaccg ggtcatctgc    840
agtgacaact actatggaga gagctgttct cgcctatgca agaagcgcga tgaccacttc    900
ggacattatg agtgccagcc agatggcagc ctgtcctgcc tgccgggctg gactgggaag    960
tactgtgacc agcctatatg tctttctggc tgtcatgagc agaatggtta ctgcagcaag   1020
ccagatgagt gcatctgccg tccaggttgg cagggtcgcc tgtgcaatga atgtatcccc   1080
cacaatggct gtcgtcatgg cacctgcagc atccctggc agtgtgcctg cgatgaggga   1140
tggggaggtc tgttttgtga ccaagatctc aactactgta ctcaccactc tccgtgcaag   1200
aatggatcaa cgtgttccaa cagtgggcca aagggttata cctgcacctg tctcccaggc   1260
tacactggtg agcactgtga gctgggactc agcaagtgtg ccagcaaccc ctgtcgaaat   1320
ggtggcagct gtaaggacca ggagaatagc taccactgcc tgtgtccccc aggctactat   1380
ggccagcact gtgagcatag taccttgacc tgtgcggact cacctgcttc aatgggggc   1440 tcttgccggg agcgcaacca ggggtccagt tatgcctgcg aatgccccc caactttacc   1500 ggctctaact gtgagaagaa agtagacagg tgtaccagca cccgtgtgc caatggaggc   1560 cagtgcctga acagaggtcc aagccgaacc tgccgctgcc ggcctggatt cacaggcacc   1620
cactgtgaac tgcacatcag cgattgtgcc cgaagtccct gtgcccacgg gggcacttgc   1680
cacgatctgg agaatgggcc tgtgtgcacc tgccccgctg gcttctctgg caggcgctgc   1740
gaggtgcgga taacccacga tgcctgtgcc tccggaccct gcttcaatgg gccaccctgc   1800
tacactggcc tctcccaaa caacttcgtc tgcaactgtc cttatggctt tgtgggcagc   1860
cgctgcgagt ttcccgtggg cttgccaccc agcttccccct gggtagctgt ctcgctgggc   1920
gtggggctag tggtactgct ggtgctgctg gtcatggtgg tagtggctgt gcggcagctg   1980
cggcttcgga ggcccgatga cgagagcagg gaagccatga caatctgtc agacttccag   2040 aaggacaacc taatccctgc cgcccagctc aaaaacacaa accagaagaa ggagctggaa   2100
gtggactgtg gtctggacaa gtccaattgt ggcaaactgc agaaccacac attggactac   2160
aatctagccc cgggactcct aggacggggc agcatgcctg gaagtatcc tcacagtgac   2220 aagagcttag gagagaaggt gccacttcgg ttacacagtg agaagccaga gtgtcgaata   2280
tcagccattt gctctcccag ggactctatg taccaatcag tgtgtttgat atcagaagag   2340
aggaacgagt gtgtgattgc cacagaggta aaggcagga gcctactcag acacccagct   2400
ccggcccagc agctgggcct tccttctgca ttgtttacat tgcatcctgt atgggacatc   2460
tttagtatgc acagtgctgc tctgcggagg aggagggaat ggcatgaact gaacagactg   2520
tgaacccgcc aagagttgca ccggctctgc acacctccag gagtctgcct ggcttcagat   2580
gggcagcccc gccaagggaa cagagttgag gagttagagg agcatcagtt gagctgatat   2640
```

```
ctaaggtgcc tctcgaactt ggacttgctc tgccaacagt ggtcatcatg gagctcttga    2700
ctgttctcca gagagtggca gtggccctag tgggtcttgg cgctgctgta gctcctgtgg    2760
gcatctgtat ttccaaagtg cctttgccca gactccatcc tcacagctgg gcccaaatga    2820
gaaagcagag aggaggcttg caaaggatag gcctcccgca ggcagaacag ccttggagtt    2880
tggcattaag caggagctac tctgcaggtg aggaaagccc gaggagggga cacgtgtgac    2940
tcctgcctcc aaccccagca ggtggggtgc cacctgcagc ctctaggcaa gagttggtcc    3000
ttcccctggt cctggtgcct ctgggctcat gtgaacagat gggcttaggg cacgcccctt    3060
ttgccagcca ggggtacagg cctcactggg gagctcaggg ccttcatgct aaactcccaa    3120
taagggagat ggggggaagg gggctgtggc ctaggccctt ccctccctca cacccatttt    3180
tgggcccttg agcctgggct ccaccagtgc ccactgttgc cccgagacca accttgaagc    3240
cgattttcaa aaatcaataa tatgaggttt tgttttgtag tttattttgg aatctagtat    3300
tttgataatt taagaatcag aagcactggc ctttctacat tttataacat tattttgtat    3360
ataatgtgta tttataatat gaaacagatg tgtacataaa aaaaaaaaa aaaaaaaaa     3420 aaaaaaa                                                             3427
```

<210> SEQ ID NO 4
<211> LENGTH: 686
<212> TYPE: PRT
<213> ORGANISM: Mus musculus

<400> SEQUENCE: 4

```
Met Thr Pro Ala Ser Arg Ser Ala Cys Arg Trp Ala Leu Leu Leu Leu
1               5                   10                  15

Ala Val Leu Trp Pro Gln Gln Arg Ala Ala Gly Ser Gly Ile Phe Gln
            20                  25                  30

Leu Arg Leu Gln Glu Phe Val Asn Gln Arg Gly Met Leu Ala Asn Gly
        35                  40                  45

Gln Ser Cys Glu Pro Gly Cys Arg Thr Phe Phe Arg Ile Cys Leu Lys
    50                  55                  60

His Phe Gln Ala Thr Phe Ser Glu Gly Pro Cys Thr Phe Gly Asn Val
65                  70                  75                  80

Ser Thr Pro Val Leu Gly Thr Asn Ser Phe Val Val Arg Asp Lys Asn
                85                  90                  95

Ser Gly Ser Gly Arg Asn Pro Leu Gln Leu Pro Phe Asn Phe Thr Trp
            100                 105                 110

Pro Gly Thr Phe Ser Leu Asn Ile Gln Ala Trp His Thr Pro Gly Asp
        115                 120                 125

Asp Leu Arg Pro Glu Thr Ser Pro Gly Asn Ser Leu Ile Ser Gln Ile
    130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
            180                 185                 190

Asp Asp His Phe Gly His Tyr Glu Cys Gln Pro Asp Gly Ser Leu Ser
        195                 200                 205

Cys Leu Pro Gly Trp Thr Gly Lys Tyr Cys Asp Gln Pro Ile Cys Leu
    210                 215                 220

Ser Gly Cys His Glu Gln Asn Gly Tyr Cys Ser Lys Pro Asp Glu Cys
225                 230                 235                 240
```

```
Ile Cys Arg Pro Gly Trp Gln Gly Arg Leu Cys Asn Glu Cys Ile Pro
              245                 250                 255

His Asn Gly Cys Arg His Gly Thr Cys Ser Ile Pro Trp Gln Cys Ala
            260                 265                 270

Cys Asp Glu Gly Trp Gly Gly Leu Phe Cys Asp Gln Asp Leu Asn Tyr
                275                 280                 285

Cys Thr His His Ser Pro Cys Lys Asn Gly Ser Thr Cys Ser Asn Ser
        290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                    325                 330                 335

Gly Gly Ser Cys Lys Asp Gln Glu Asn Ser Tyr His Cys Leu Cys Pro
                340                 345                 350

Pro Gly Tyr Tyr Gly Gln His Cys Glu His Ser Thr Leu Thr Cys Ala
            355                 360                 365

Asp Ser Pro Cys Phe Asn Gly Gly Ser Cys Arg Glu Arg Asn Gln Gly
        370                 375                 380

Ser Ser Tyr Ala Cys Glu Cys Pro Pro Asn Phe Thr Gly Ser Asn Cys
385                 390                 395                 400

Glu Lys Lys Val Asp Arg Cys Thr Ser Asn Pro Cys Ala Asn Gly Gly
                405                 410                 415

Gln Cys Leu Asn Arg Gly Pro Ser Arg Thr Cys Arg Cys Arg Pro Gly
                420                 425                 430

Phe Thr Gly Thr His Cys Glu Leu His Ile Ser Asp Cys Ala Arg Ser
            435                 440                 445

Pro Cys Ala His Gly Gly Thr Cys His Asp Leu Glu Asn Gly Pro Val
    450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                485                 490                 495

Tyr Thr Gly Leu Ser Pro Asn Asn Phe Val Cys Asn Cys Pro Tyr Gly
                500                 505                 510

Phe Val Gly Ser Arg Cys Glu Phe Pro Val Gly Leu Pro Pro Ser Phe
            515                 520                 525

Pro Trp Val Ala Val Ser Leu Gly Val Gly Leu Val Val Leu Leu Val
    530                 535                 540

Leu Leu Val Met Val Val Val Ala Val Arg Gln Leu Arg Leu Arg Arg
545                 550                 555                 560

Pro Asp Asp Glu Ser Arg Glu Ala Met Asn Asn Leu Ser Asp Phe Gln
                565                 570                 575

Lys Asp Asn Leu Ile Pro Ala Ala Gln Leu Lys Asn Thr Asn Gln Lys
            580                 585                 590

Lys Glu Leu Glu Val Asp Cys Gly Leu Asp Lys Ser Asn Cys Gly Lys
        595                 600                 605

Leu Gln Asn His Thr Leu Asp Tyr Asn Leu Ala Pro Gly Leu Leu Gly
    610                 615                 620

Arg Gly Ser Met Pro Gly Lys Tyr Pro His Ser Asp Lys Ser Leu Gly
625                 630                 635                 640

Glu Lys Val Pro Leu Arg Leu His Ser Glu Lys Pro Glu Cys Arg Ile
                645                 650                 655

Ser Ala Ile Cys Ser Pro Arg Asp Ser Met Tyr Gln Ser Val Cys Leu
```

```
            660             665             670
Ile Ser Glu Glu Arg Asn Glu Cys Val Ile Ala Thr Glu Val
            675             680             685
```

<210> SEQ ID NO 5
<211> LENGTH: 9312
<212> TYPE: DNA
<213> ORGANISM: Homo sapiens

<400> SEQUENCE: 5

| | |
|---|---|
| atgccgccgc tcctggcgcc cctgctctgc ctggcgctgc tgcccgcgct cgccgcacga | 60 |
| ggcccgcgat gctcccagcc cggtgagacc tgcctgaatg cgggaagtg tgaagcggcc | 120 |
| aatggcacgg aggcctgcgt ctgtggcggg gccttcgtgg gccgcgatg ccaggacccc | 180 |
| aacccgtgcc tcagcacccc ctgcaagaac gccgggacat gccacgtggt ggaccgcaga | 240 |
| ggcgtggcag actatgcctg cagctgtgcc ctgggcttct ctgggcccct ctgcctgaca | 300 |
| cccctggaca atgcctgcct caccaacccc tgccgcaacg gggcacctg cgacctgctc | 360 |
| acgctgacgg agtacaagtg ccgctgcccg ccggctggt cagggaaatc gtgccagcag | 420 |
| gctgacccgt gcgcctccaa cccctgcgcc aacgtggcc agtgcctgcc cttcgaggcc | 480 |
| tcctacatct gccactgccc acccagcttc atggcccca cctgccggca ggatgtcaac | 540 |
| gagtgtggcc agaagcccgg gctttgccgc acggaggca cctgccacaa cgaggtcggc | 600 |
| tcctaccgct gcgtctgccg cgccacccac actggcccca actgcgagcg ccctacgtg | 660 |
| ccctgcagcc cctcgccctg ccagaacggg ggcacctgcc gccccacggg cgacgtcacc | 720 |
| cacgagtgtg cctgcctgcc aggcttcacc ggccagaact gtgaggaaaa tatcgacgat | 780 |
| tgtccaggaa acaactgcaa gaacgggggt gcctgtgtgg acggcgtgaa cacctacaac | 840 |
| tgccgctgcc cgccagagtg gacaggtcag tactgtaccg aggatgtgga cgagtgccag | 900 |
| ctgatgccaa atgcctgcca gaacggcggg acctgccaca caccacggg tggctacaac | 960 |
| tgcgtgtgtg tcaacggctg gactggtgag gactgcagcg agaacattga tgactgtgcc | 1020 |
| agcgccgcct gcttccacgg cgccacctgc catgaccgtg tggcctcctt ctactgcgag | 1080 |
| tgtccccatg gccgcacagg tctgctgtgc caccccaacg acgcatgcat cagcaacccc | 1140 |
| tgtaacgagg gctccaactg cgacaccaac cctgtcaatg caaggccat ctgcacctgc | 1200 |
| ccctcggggt acacgggccc ggcctgcagc caggacgtgg atgagtgctc gctgggtgcc | 1260 |
| aaccccctgcg agcatgcggg caagtgcatc aacacgctgg gctccttcga gtgccagtgt | 1320 |
| ctgcagggct acacgggccc ccgatgcgag atcgacgtca cgagtgcgt ctcgaacccg | 1380 |
| tgccagaacg acgccacctg cctggaccag attggggagt ccagtgcat ctgcatgccc | 1440 |
| ggctacgagg gtgtgcactg cgaggtcaac acagacgagt gtgccagcag ccctgcctg | 1500 |
| cacaatggcc gctgcctgga caagatcaat gagttccagt gcgagtgccc cacgggcttc | 1560 |
| actgggcatc tgtgccagta cgatgtggac gagtgtgcca gcacccctg caagaatggt | 1620 |
| gccaagtgcc tggacggacc caacacttac acctgtgtgt gcacggaagg gtacacgggg | 1680 |
| acgcactgcg aggtggacat cgatgagtgc gaccccgacc ctgccactca cggtcctgc | 1740 |
| aaggacggcg tcgccacctt cacctgcctc tgccgcccag gctacacggg ccaccactgc | 1800 |
| gagaccaaca tcaacgagtg ctccagccag ccctgccgcc acggggcac tgccaggac | 1860 |
| cgcgacaacg cctacctctg cttctgcctg aagggaccaa caggacccaa ctgcgagatc | 1920 |
| aacctggatg actgtgccag cagccctgc gactcgggca cctgtctgga caagatcgat | 1980 |
| ggctacgagt gtgcctgtga gccgggctac acagggagca tgtgtaacat caacatcgat | 2040 |

```
gagtgtgcgg gcaacccctg ccacaacggg ggcacctgcg aggacggcat caatggcttc    2100
acctgccgct gccccgaggg ctaccacgac cccacctgcc tgtctgaggt caatgagtgc    2160
aacagcaacc cctgcgtcca cggggcctgc cgggacagcc tcaacgggta caagtgcgac    2220
tgtgaccctg ggtggagtgg gaccaactgt gacatcaaca acaatgagtg tgaatccaac    2280
ccttgtgtca acggcggcac ctgcaaagac atgaccagtg gctacgtgtg cacctgccgg    2340
gagggcttca gcggtcccaa ctgccagacc aacatcaacg agtgtgcgtc caacccatgt    2400
ctgaaccagg gcacgtgtat tgacgacgtt gccgggtaca agtgcaactg cctgctgccc    2460
tacacaggtg ccacgtgtga ggtggtgctg gccccgtgtg cccccagccc ctgcagaaac    2520
ggcggggagt gcaggcaatc cgaggactat gagagcttct cctgtgtctg ccccacgggc    2580
tggcaagcag ggcagacctg tgaggtcgac atcaacgagt gcgttctgag cccgtgccgg    2640
cacggcgcat cctgccagaa cacccacggc ggctaccgct gccactgcca ggccggctac    2700
agtgggcgca actgcgagac cgacatcgac gactgccggc ccaacccgtg tcacaacggg    2760
ggctcctgca cagacggcat caacacggcc ttctgcgact gcctgccgg cttccggggc    2820 actttctgtg aggaggacat caacgagtgt gccagtgacc cctgccgcaa cggggccaac    2880
tgcacggact gcgtggacag ctacacgtgc acctgccccg caggcttcag cgggatccac    2940
tgtgagaaca acacgcctga ctgcacagag agctcctgct tcaacggtgg cacctgcgtg    3000
gacggcatca actcgttcac ctgcctgtgt ccacccggct tcacgggcag ctactgccag    3060
cacgatgtca atgagtgcga ctcacagccc tgcctgcatg gcggcacctg tcaggacggc    3120
tgcggctcct acaggtgcac ctgcccccag ggctacactg gccccaactg ccagaacctt    3180
gtgcactggt gtgactcctc gccctgcaag aacggcggca aatgctgcca gcccacacc    3240 cagtaccgct gcgagtgccc cagcggctgg accggccttt actgcgacgt gcccagcgtg    3300
tcctgtgagg tggctgcgca gcgacaaggt gttgacgttg cccgcctgtg ccagcatgga    3360
gggctctgtg tggacgcggg caacacgcac cactgccgct gccaggcggg ctacacaggc    3420
agctactgtg aggacctggt ggacgagtgc tcacccagcc cctgccagaa cggggccacc    3480
tgcacggact acctgggcgg ctactcctgc aagtgcgtgg ccggctacca cggggtgaac    3540
tgctctgagg agatcgacga gtgcctctcc caccccctgcc agaacggggg cacctgcctc    3600
gacctcccca acacctacaa gtgctcctgc ccacggggca ctcagggtgt gcactgtgag    3660
atcaacgtgg acgactgcaa tccccccgtt gaccccgtgt cccggagccc caagtgcttt    3720
aacaacggca cctgcgtgga ccaggtgggc ggctacagct gcacctgccc gccgggcttc    3780
gtgggtgagc gctgtgaggg ggatgtcaac gagtgcctgt ccaatccctg cgacgcccgt    3840
ggcacccaga actgcgtgca gcgcgtcaat gacttccact gcgagtgccg tgctggtcac    3900
accgggcgcc gctgcgagtc cgtcatcaat ggctgcaaag gcaagccctg caagaatggg    3960
ggcacctgcg ccgtggcctc caacaccgcc cgcgggttca tctgcaagtg ccctgcgggc    4020
ttcgagggcg ccacgtgtga gaatgacgct cgtacctgcg gcagcctgcg ctgcctcaac    4080
ggcggcacat gcatctccgg cccgcgcagc cccacctgcc tgtgcctggg ccccttcacg    4140 ggcccccgaat gccagttccc ggccagcagc cctgcctgg cggcaaccc ctgctacaac    4200 caggggacct gtgagcccac atccgagagc cccttctacc gttgcctgtg cccgccaaa    4260 ttcaacgggc tcttgtgcca catcctggac tacagcttcg ggggtggggc cgggcgcgac    4320
atccccccgc cgctgatcga ggaggcgtgc gagctgcccg agtgccagga ggacgcgggc    4380
aacaaggtct gcagcctgca gtgcaacaac cacgcgtgcg gctgggacgg cggtgactgc    4440
```

```
tccctcaact tcaatgaccc ctggaagaac tgcacgcagt ctctgcagtg ctggaagtac   4500
ttcagtgacg gccactgtga cagccagtgc aactcagccg gctgcctctt cgacggcttt   4560
gactgccagc gtgcggaagg ccagtgcaac cccctgtacg accagtactg caaggaccac   4620
ttcagcgacg ggcactgcga ccagggctgc aacagcgcgg agtgcgagtg ggacgggctg   4680
gactgtgcgg agcatgtacc cgagaggctg gcggccggca cgctggtggt ggtggtgctg   4740
atgccgccgg agcagctgcg caacagctcc ttccacttcc tgcgggagct cagccgcgtg   4800
ctgcacacca acgtggtctt caagcgtgac gcacacggcc agcagatgat cttcccctac   4860
tacggccgcg aggaggagct gcgcaagcac cccatcaagc gtgccgccga gggctgggcc   4920
gcacctgacg ccctgctggg ccaggtgaag gcctcgctgc tccctggtgg cagcgagggt   4980
gggcggcggc ggagggagct ggaccccatg gacgtccgcg gctccatcgt ctacctggag   5040
attgacaacc ggcagtgtgt gcaggcctcc tcgcagtgct tccagagtgc caccgacgtg   5100
gccgcattcc tgggagcgct cgcctcgctg gcagcctca acatccccta caagatcgag   5160
gccgtgcaga gtgagaccgt ggagccgccc ccgccggcgc agctgcactt catgtacgtg   5220
gcggcggccg cctttgtgct tctgttcttc gtgggctgcg gggtgctgct gtcccgcaag   5280
cgccggcggc agcatggcca gctctggttc cctgagggct tcaaagtgtc tgaggccagc   5340
aagaagaagc ggcgggagcc cctcggcgag gactccgtgg gcctcaagcc cctgaagaac   5400
gcttcagacg gtgccctcat ggacgacaac cagaatgagt gggggacga ggacctggag   5460 accaagaagt tccggttcga ggagcccgtg gttctgcctg acctggacga ccagacagac   5520
caccggcagt ggactcagca gcacctggat gccgctgacc tgcgcatgtc tgccatggcc   5580
cccacaccgc cccagggtga ggttgacgcc gactgcatgg acgtcaatgt ccgcgggcct   5640
gatggcttca ccccgctcat gatcgcctcc tgcagcgggg cggcctgga cgggcaac    5700 agcgaggaag aggaggacgc gccggccgtc atctccgact tcatctacca gggcgccagc   5760
ctgcacaacc agacagaccg cacgggcgag accgccttgc acctggccgc cgctactca   5820 cgctctgatg ccgccaagcg cctgctggag gccagcgcag atgccaacat ccaggacaac   5880
atgggccgca ccccgctgca tgcggctgtg tctgccgacg cacaaggtgt cttccagatc   5940
ctgatccgga accgagccac agacctggat gcccgcatgc atgatggcac gacgccactg   6000
atcctggctg cccgcctggc cgtggagggc atgctggagg acctcatcaa ctcacacgcc   6060
gacgtcaacg ccgtagatga cctgggcaag tccgccctgc actgggccgc cgccgtgaac   6120
aatgtggatg ccgcagttgt gctcctgaag aacgggctca acaaagatat gcagaacaac   6180
agggaggaga cacccctgtt tctggccgcc cgggagggca gctacgagac cgccaaggtg   6240
ctgctggacc actttgccaa ccgggacatc acggatcata tggaccgcct gccgcgcgac   6300
atcgcacagg agcgcatgca tcacgacatc gtgaggctgc tggacgagta caacctggtg   6360
cgcagcccgc agctgcacgg agcccgctg ggggcacgc ccaccctgtc gccccgctc    6420 tgctcgccca acggctacct gggcagcctc aagcccggcg tgcagggcaa gaaggtccgc   6480
aagcccagca gcaaaggcct ggcctgtgga agcaaggagg ccaaggacct caaggcacgg   6540
aggaagaagt cccaggacgg caagggctgc ctgctggaca gctccggcat gctctcgccc   6600
gtggactccc tggagtcacc ccatggctac ctgtcagacg tggcctcgcc gccactgctg   6660
ccctccccgt tccagcagtc tccgtccgtg cccctcaacc acctgcctgg gatgcccgac   6720
acccacctgg gcatcgggca cctgaacgtg gcggccaagc ccgagatggc ggcgctgggt   6780 ggggcggcc ggctggcctt tgagactggc ccacctcgtc tctcccacct gcctgtggcc   6840
```

```
tctggcacca gcaccgtcct gggctccagc agcggagggg ccctgaattt cactgtgggc    6900
gggtccacca gtttgaatgg tcaatgcgag tggctgtccc ggctgcagag cggcatggtg    6960
ccgaaccaat acaaccctct gcgggggagt gtggcaccag gcccctgag cacacaggcc     7020 ccctccctgc agcatggcat ggtaggcccg ctgcacagta gccttgctgc cagcgccctg    7080
tcccagatga tgagctacca gggcctgccc agcacccggc tggccaccca gcctcacctg    7140
gtgcagaccc agcaggtgca gccacaaaac ttacagatgc agcagcagaa cctgcagcca    7200
gcaaacatcc agcagcagca aagcctgcag ccgccaccac caccaccaca gccgcacctt    7260
ggcgtgagct cagcagccag cggccacctg gccggagct tcctgagtgg agagccgagc     7320
caggcagacg tgcagccact gggcccagc agcctggcgg tgcacactat tctgccccag     7380
gagagccccg ccctgcccac gtcgctgcca tcctcgctgg tcccaccgt gaccgcagcc     7440 cagttcctga cgcccccctc gcagcacagc tactcctcgc ctgtggacaa caccccagc     7500 caccagctac aggtgcctga gcaccccttc ctcacccgt ccctgagtc ccctgaccag      7560 tggtccagct cgtccccgca ttccaacgtc tccgactggt ccgagggcgt ctccagccct    7620
cccaccagca tgcagtccca gatcgcccgc attccggagg ccttcaagta acgcgcgc     7680 cccacgagac cccggcttcc tttcccaagc cttcgggcgt ctgtgtgcgc tctgtggatg    7740
ccagggccga ccagaggagc cttttaaaa cacatgtttt tatacaaaat aagaacgagg     7800 atttaatt ttttagtat ttatttatgt actttattt tacacagaaa cactgccttt        7860
ttatttatat gtactgtttt atctggcccc aggtagaaac ttttatctat tctgagaaaa    7920
caagcaagtt ctgagagcca gggttttcct acgtaggatg aaaagattct tctgtgttta    7980
taaaatataa acaaagattc atgatttata atgccattt atttattgat tccttttttc     8040
aaaatccaaa aagaaatgat gttggagaag ggaagttgaa cgagcatagt ccaaaaagct    8100
cctggggcgt ccaggccgcg cccttttccc gacgcccacc caaccccaag ccagcccggc    8160
cgctccacca gcatcacctg cctgttagga gaagctgcat ccagaggcaa acggaggcaa    8220
agctggctca ccttccgcac gcggattaat ttgcatctga aataggaaac aagtgaaagc    8280
atatgggtta gatgttgcca tgtgttttag atggttctt gcaagcatgc ttgtgaaaat     8340
gtgttctcgg agtgtgtatg ccaagagtgc acccatggta ccaatcatga atctttgttt    8400
caggttcagt attatgtagt tgttcgttgg ttatacaagt tcttggtccc tccagaacca    8460
ccccggcccc ctgcccgttc ttgaaatgta ggcatcatgc atgtcaaaca tgagatgtgt    8520
ggactgtggc acttgcctgg gtcacacacg gaggcatcct accctttct ggggaaagac     8580 actgcctggg ctgaccccgg tggcggcccc agcacctcag cctgcacagt gtcccccagg    8640
ttccgaagaa gatgctccag caacacagcc tgggcccag ctcgcgggac ccgacccccc     8700
gtgggctccc gtgttttgta ggagacttgc cagagccggg cacattgagc tgtgcaacgc    8760
cgtgggctgc gtcctttggt cctgtccccg cagccctggc aggggcatg cggtcgggca     8820 ggggctggag ggaggcgggg gctgcccttg ggccaccct cctagtttgg gaggagcaga     8880 ttttttgcaat accaagtata gcctatggca gaaaaatgt ctgtaaatat gttttaaag     8940 gtggattttg tttaaaaaat cttaatgaat gagtctgttg tgtgtcatgc cagtgaggga    9000
cgtcagactt ggctcagctc ggggagcctt agccgcccat gcactggga cgctccgctg     9060 ccgtgccgcc tgcactcctc agggcagcct ccccggctc tacggggcc gcgtggtgcc      9120 atcccccaggg ggcatgacca gatgcgtccc aagatgttga ttttactgt gttttataaa    9180 atagagtgta gtttacagaa aaagactta aaagtgatct acatgaggaa ctgtagatga     9240
```

```
tgtatttttt tcatctttt tgttaactga tttgcaataa aaatgatact gatggtgaaa    9300
aaaaaaaaaa aa                                                      9312
```

<210> SEQ ID NO 6
<211> LENGTH: 2556
<212> TYPE: PRT
<213> ORGANISM: Homo sapiens

<400> SEQUENCE: 6

```
Met Pro Pro Leu Leu Ala Pro Leu Leu Cys Leu Ala Leu Leu Pro Ala
 1               5                  10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
             35                  40                  45

Gly Gly Ala Phe Val Gly Pro Arg Cys Gln Asp Pro Asn Pro Cys Leu
         50                  55                  60

Ser Thr Pro Cys Lys Asn Ala Gly Thr Cys His Val Val Asp Arg Arg
 65                  70                  75                  80

Gly Val Ala Asp Tyr Ala Cys Ser Cys Ala Leu Gly Phe Ser Gly Pro
                 85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
```

```
                  355                 360                 365
Leu Cys His Leu Asn Asp Ala Cys Ile Ser Asn Pro Cys Asn Glu Gly
370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
                420                 425                 430

Leu Gly Ser Phe Glu Cys Gln Cys Leu Gln Gly Tyr Thr Gly Pro Arg
                435                 440                 445

Cys Glu Ile Asp Val Asn Glu Cys Val Ser Asn Pro Cys Gln Asn Asp
                450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
                500                 505                 510

Gln Cys Glu Cys Pro Thr Gly Phe Thr Gly His Leu Cys Gln Tyr Asp
                515                 520                 525

Val Asp Glu Cys Ala Ser Thr Pro Cys Lys Asn Gly Ala Lys Cys Leu
                530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
                580                 585                 590

Pro Gly Tyr Thr Gly His His Cys Glu Thr Asn Ile Asn Glu Cys Ser
                595                 600                 605

Ser Gln Pro Cys Arg His Gly Gly Thr Cys Gln Asp Arg Asp Asn Ala
610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
                660                 665                 670

Ser Met Cys Asn Ile Asn Ile Asp Glu Cys Ala Gly Asn Pro Cys His
                675                 680                 685

Asn Gly Gly Thr Cys Glu Asp Gly Ile Asn Gly Phe Thr Cys Arg Cys
                690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
                755                 760                 765

Lys Asp Met Thr Ser Gly Tyr Val Cys Thr Cys Arg Glu Gly Phe Ser
770                 775                 780
```

-continued

```
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
            805                 810                 815
Cys Leu Leu Pro Tyr Thr Gly Ala Thr Cys Glu Val Val Leu Ala Pro
            820                 825                 830
Cys Ala Pro Ser Pro Cys Arg Asn Gly Gly Glu Cys Arg Gln Ser Glu
            835                 840                 845
Asp Tyr Glu Ser Phe Ser Cys Val Cys Pro Thr Gly Trp Gln Ala Gly
            850                 855                 860
Gln Thr Cys Glu Val Asp Ile Asn Glu Cys Val Leu Ser Pro Cys Arg
865                 870                 875                 880
His Gly Ala Ser Cys Gln Asn Thr His Gly Gly Tyr Arg Cys His Cys
                885                 890                 895
Gln Ala Gly Tyr Ser Gly Arg Asn Cys Glu Thr Asp Ile Asp Asp Cys
                900                 905                 910
Arg Pro Asn Pro Cys His Asn Gly Gly Ser Cys Thr Asp Gly Ile Asn
            915                 920                 925
Thr Ala Phe Cys Asp Cys Leu Pro Gly Phe Arg Gly Thr Phe Cys Glu
            930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
                965                 970                 975
Ser Gly Ile His Cys Glu Asn Asn Thr Pro Asp Cys Thr Glu Ser Ser
                980                 985                 990
Cys Phe Asn Gly Gly Thr Cys Val Asp Gly Ile Asn Ser Phe Thr Cys
            995                 1000                1005
Leu Cys Pro Pro Gly Phe Thr Gly Ser Tyr Cys Gln His Asp Val Asn
            1010                1015                1020
Glu Cys Asp Ser Gln Pro Cys Leu His Gly Gly Thr Cys Gln Asp Gly
1025                1030                1035                1040
Cys Gly Ser Tyr Arg Cys Thr Cys Pro Gln Gly Tyr Thr Gly Pro Asn
                1045                1050                1055
Cys Gln Asn Leu Val His Trp Cys Asp Ser Ser Pro Cys Lys Asn Gly
                1060                1065                1070
Gly Lys Cys Trp Gln Thr His Thr Gln Tyr Arg Cys Glu Cys Pro Ser
            1075                1080                1085
Gly Trp Thr Gly Leu Tyr Cys Asp Val Pro Ser Val Ser Cys Glu Val
            1090                1095                1100
Ala Ala Gln Arg Gln Gly Val Asp Val Ala Arg Leu Cys Gln His Gly
1105                1110                1115                1120
Gly Leu Cys Val Asp Ala Gly Asn Thr His His Cys Arg Cys Gln Ala
                1125                1130                1135
Gly Tyr Thr Gly Ser Tyr Cys Glu Asp Leu Val Asp Glu Cys Ser Pro
                1140                1145                1150
Ser Pro Cys Gln Asn Gly Ala Thr Cys Thr Asp Tyr Leu Gly Gly Tyr
                1155                1160                1165
Ser Cys Lys Cys Val Ala Gly Tyr His Gly Val Asn Cys Ser Glu Glu
            1170                1175                1180
Ile Asp Glu Cys Leu Ser His Pro Cys Gln Asn Gly Gly Thr Cys Leu
1185                1190                1195                1200
Asp Leu Pro Asn Thr Tyr Lys Cys Ser Cys Pro Arg Gly Thr Gln Gly
            1205                1210                1215
```

-continued

Val His Cys Glu Ile Asn Val Asp Asp Cys Asn Pro Val Asp Pro
1220               1225               1230

Val Ser Arg Ser Pro Lys Cys Phe Asn Asn Gly Thr Cys Val Asp Gln
1235               1240               1245

Val Gly Gly Tyr Ser Cys Thr Cys Pro Pro Gly Phe Val Gly Glu Arg
1250               1255               1260

Cys Glu Gly Asp Val Asn Glu Cys Leu Ser Asn Pro Cys Asp Ala Arg
1265               1270               1275               1280

Gly Thr Gln Asn Cys Val Gln Arg Val Asn Asp Phe His Cys Glu Cys
            1285               1290               1295

Arg Ala Gly His Thr Gly Arg Arg Cys Glu Ser Val Ile Asn Gly Cys
            1300               1305               1310

Lys Gly Lys Pro Cys Lys Asn Gly Gly Thr Cys Ala Val Ala Ser Asn
            1315               1320               1325

Thr Ala Arg Gly Phe Ile Cys Lys Cys Pro Ala Gly Phe Glu Gly Ala
            1330               1335               1340

Thr Cys Glu Asn Asp Ala Arg Thr Cys Gly Ser Leu Arg Cys Leu Asn
1345               1350               1355               1360

Gly Gly Thr Cys Ile Ser Gly Pro Arg Ser Pro Thr Cys Leu Cys Leu
            1365               1370               1375

Gly Pro Phe Thr Gly Pro Glu Cys Gln Phe Pro Ala Ser Ser Pro Cys
            1380               1385               1390

Leu Gly Gly Asn Pro Cys Tyr Asn Gln Gly Thr Cys Glu Pro Thr Ser
            1395               1400               1405

Glu Ser Pro Phe Tyr Arg Cys Leu Cys Pro Ala Lys Phe Asn Gly Leu
        1410               1415               1420

Leu Cys His Ile Leu Asp Tyr Ser Phe Gly Gly Gly Ala Gly Arg Asp
1425               1430               1435               1440

Ile Pro Pro Pro Leu Ile Glu Glu Ala Cys Glu Leu Pro Glu Cys Gln
            1445               1450               1455

Glu Asp Ala Gly Asn Lys Val Cys Ser Leu Gln Cys Asn Asn His Ala
            1460               1465               1470

Cys Gly Trp Asp Gly Gly Asp Cys Ser Leu Asn Phe Asn Asp Pro Trp
            1475               1480               1485

Lys Asn Cys Thr Gln Ser Leu Gln Cys Trp Lys Tyr Phe Ser Asp Gly
            1490               1495               1500

His Cys Asp Ser Gln Cys Asn Ser Ala Gly Cys Leu Phe Asp Gly Phe
1505               1510               1515               1520

Asp Cys Gln Arg Ala Glu Gly Gln Cys Asn Pro Leu Tyr Asp Gln Tyr
            1525               1530               1535

Cys Lys Asp His Phe Ser Asp Gly His Cys Asp Gln Gly Cys Asn Ser
            1540               1545               1550

Ala Glu Cys Glu Trp Asp Gly Leu Asp Cys Ala Glu His Val Pro Glu
            1555               1560               1565

Arg Leu Ala Ala Gly Thr Leu Val Val Val Leu Met Pro Pro Glu
            1570               1575               1580

Gln Leu Arg Asn Ser Ser Phe His Phe Leu Arg Glu Leu Ser Arg Val
1585               1590               1595               1600

Leu His Thr Asn Val Val Phe Lys Arg Asp Ala His Gly Gln Gln Met
            1605               1610               1615

Ile Phe Pro Tyr Tyr Gly Arg Glu Glu Glu Leu Arg Lys His Pro Ile
            1620               1625               1630

Lys Arg Ala Ala Glu Gly Trp Ala Ala Pro Asp Ala Leu Leu Gly Gln

-continued

```
                1635                1640                1645
Val Lys Ala Ser Leu Leu Pro Gly Gly Ser Glu Gly Gly Arg Arg Arg
    1650                1655                1660
Arg Glu Leu Asp Pro Met Asp Val Arg Gly Ser Ile Val Tyr Leu Glu
1665                1670                1675                1680
Ile Asp Asn Arg Gln Cys Val Gln Ala Ser Ser Gln Cys Phe Gln Ser
                1685                1690                1695
Ala Thr Asp Val Ala Ala Phe Leu Gly Ala Leu Ala Ser Leu Gly Ser
    1700                1705                1710
Leu Asn Ile Pro Tyr Lys Ile Glu Ala Val Gln Ser Glu Thr Val Glu
            1715                1720                1725
Pro Pro Pro Ala Gln Leu His Phe Met Tyr Val Ala Ala Ala Ala
    1730                1735                1740
Phe Val Leu Leu Phe Val Gly Cys Gly Val Leu Leu Ser Arg Lys
1745                1750                1755                1760
Arg Arg Arg Gln His Gly Gln Leu Trp Phe Pro Glu Gly Phe Lys Val
                1765                1770                1775
Ser Glu Ala Ser Lys Lys Lys Arg Arg Glu Pro Leu Gly Glu Asp Ser
            1780                1785                1790
Val Gly Leu Lys Pro Leu Lys Asn Ala Ser Asp Gly Ala Leu Met Asp
    1795                1800                1805
Asp Asn Gln Asn Glu Trp Gly Asp Glu Asp Leu Glu Thr Lys Lys Phe
    1810                1815                1820
Arg Phe Glu Glu Pro Val Val Leu Pro Asp Leu Asp Asp Gln Thr Asp
1825                1830                1835                1840
His Arg Gln Trp Thr Gln Gln His Leu Asp Ala Ala Asp Leu Arg Met
                1845                1850                1855
Ser Ala Met Ala Pro Thr Pro Pro Gln Gly Glu Val Asp Ala Asp Cys
        1860                1865                1870
Met Asp Val Asn Val Arg Gly Pro Asp Gly Phe Thr Pro Leu Met Ile
    1875                1880                1885
Ala Ser Cys Ser Gly Gly Gly Leu Glu Thr Gly Asn Ser Glu Glu Glu
    1890                1895                1900
Glu Asp Ala Pro Ala Val Ile Ser Asp Phe Ile Tyr Gln Gly Ala Ser
1905                1910                1915                1920
Leu His Asn Gln Thr Asp Arg Thr Gly Glu Thr Ala Leu His Leu Ala
            1925                1930                1935
Ala Arg Tyr Ser Arg Ser Asp Ala Ala Lys Arg Leu Leu Glu Ala Ser
    1940                1945                1950
Ala Asp Ala Asn Ile Gln Asp Asn Met Gly Arg Thr Pro Leu His Ala
    1955                1960                1965
Ala Val Ser Ala Asp Ala Gln Gly Val Phe Gln Ile Leu Ile Arg Asn
    1970                1975                1980
Arg Ala Thr Asp Leu Asp Ala Arg Met His Asp Gly Thr Thr Pro Leu
1985                1990                1995                2000
Ile Leu Ala Ala Arg Leu Ala Val Glu Gly Met Leu Glu Asp Leu Ile
        2005                2010                2015
Asn Ser His Ala Asp Val Asn Ala Val Asp Asp Leu Gly Lys Ser Ala
    2020                2025                2030
Leu His Trp Ala Ala Ala Val Asn Asn Val Asp Ala Ala Val Val Leu
        2035                2040                2045
Leu Lys Asn Gly Ala Asn Lys Asp Met Gln Asn Asn Arg Glu Glu Thr
    2050                2055                2060
```

```
Pro Leu Phe Leu Ala Ala Arg Glu Gly Ser Tyr Glu Thr Ala Lys Val
2065                2070                2075                2080

Leu Leu Asp His Phe Ala Asn Arg Asp Ile Thr Asp His Met Asp Arg
            2085                2090                2095

Leu Pro Arg Asp Ile Ala Gln Glu Arg Met His His Asp Ile Val Arg
        2100                2105                2110

Leu Leu Asp Glu Tyr Asn Leu Val Arg Ser Pro Gln Leu His Gly Ala
    2115                2120                2125

Pro Leu Gly Gly Thr Pro Thr Leu Ser Pro Pro Leu Cys Ser Pro Asn
2130                2135                2140

Gly Tyr Leu Gly Ser Leu Lys Pro Gly Val Gln Gly Lys Lys Val Arg
    2145                2150                2155                2160

Lys Pro Ser Ser Lys Gly Leu Ala Cys Gly Ser Lys Glu Ala Lys Asp
            2165                2170                2175

Leu Lys Ala Arg Arg Lys Lys Ser Gln Asp Gly Lys Gly Cys Leu Leu
        2180                2185                2190

Asp Ser Ser Gly Met Leu Ser Pro Val Asp Ser Leu Glu Ser Pro His
    2195                2200                2205

Gly Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro Asp
2225                2230                2235                2240

Thr His Leu Gly Ile Gly His Leu Asn Val Ala Ala Lys Pro Glu Met
            2245                2250                2255

Ala Ala Leu Gly Gly Gly Gly Arg Leu Ala Phe Glu Thr Gly Pro Pro
        2260                2265                2270

Arg Leu Ser His Leu Pro Val Ala Ser Gly Thr Ser Thr Val Leu Gly
    2275                2280                2285

Ser Ser Ser Gly Gly Ala Leu Asn Phe Thr Val Gly Gly Ser Thr Ser
    2290                2295                2300

Leu Asn Gly Gln Cys Glu Trp Leu Ser Arg Leu Gln Ser Gly Met Val
2305                2310                2315                2320

Pro Asn Gln Tyr Asn Pro Leu Arg Gly Ser Val Ala Pro Gly Pro Leu
            2325                2330                2335

Ser Thr Gln Ala Pro Ser Leu Gln His Gly Met Val Gly Pro Leu His
        2340                2345                2350

Ser Ser Leu Ala Ala Ser Ala Leu Ser Gln Met Met Ser Tyr Gln Gly
    2355                2360                2365

Leu Pro Ser Thr Arg Leu Ala Thr Gln Pro His Leu Val Gln Thr Gln
    2370                2375                2380

Gln Val Gln Pro Gln Asn Leu Gln Met Gln Gln Asn Leu Gln Pro
2385                2390                2395                2400

Ala Asn Ile Gln Gln Gln Gln Ser Leu Gln Pro Pro Pro Pro Pro
            2405                2410                2415

Gln Pro His Leu Gly Val Ser Ser Ala Ala Ser Gly His Leu Gly Arg
        2420                2425                2430

Ser Phe Leu Ser Gly Glu Pro Ser Gln Ala Asp Val Gln Pro Leu Gly
    2435                2440                2445

Pro Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala Ala
2465                2470                2475                2480

Gln Phe Leu Thr Pro Pro Ser Gln His Ser Tyr Ser Ser Pro Val Asp
            2485                2490                2495
```

Asn Thr Pro Ser His Gln Leu Gln Val Pro Glu His Pro Phe Leu Thr
        2500                2505                2510

Pro Ser Pro Glu Ser Pro Asp Gln Trp Ser Ser Ser Pro His Ser
     2515                2520                2525

Asn Val Ser Asp Trp Ser Glu Gly Val Ser Ser Pro Pro Thr Ser Met
  2530                2535                2540

Gln Ser Gln Ile Ala Arg Ile Pro Glu Ala Phe Lys
2545                2550                2555

<210> SEQ ID NO 7
<211> LENGTH: 6009
<212> TYPE: DNA
<213> ORGANISM: Homo sapiens

<400> SEQUENCE: 7

| | | | | | |
|---|---|---|---|---|---|
| atgcagcccc | cttcactgct | gctgctgctg | ctgctgctgc | tgctatgtgt | ctcagtggtc | 60 |
| agacccagag | ggctgctgtg | tgggagtttc | ccagaaccct | gtgccaatgg | aggcacctgc | 120 |
| ctgagcctgt | ctctgggaca | agggacctgc | cagtgtgccc | ctggcttcct | gggtgagacg | 180 |
| tgccagtttc | ctgaccccctg | ccagaacgcc | cagctctgcc | aaaatggagg | cagctgccaa | 240 |
| gccctgcttc | ccgctcccct | agggctcccc | agctctccct | ctccattgac | acccagcttc | 300 |
| ttgtgcactt | gcctcctgg | cttcactggt | gagagatgcc | aggccaagct | tgaagaccct | 360 |
| tgtcctccct | ccttctgttc | caaaaggggc | cgctgccaca | tccaggcctc | gggccgccca | 420 |
| cagtgctcct | gcatgcctgg | atggacaggt | gagcagtgcc | agcttcggga | cttctgttca | 480 |
| gccaacccat | gtgttaatgg | aggggtgtgt | ctggccacgt | accccagat | ccagtgccac | 540 |
| tgcccaccgg | gcttcgaggg | ccatgcctgt | gaacgtgatg | tcaacgagtg | cttccaggac | 600 |
| ccaggaccct | gccccaaagg | cacctcctgc | cataacaccc | tgggctcctt | ccagtgcctc | 660 |
| tgccctgtgg | ggcaggaggg | tccacgttgt | gagctgcggg | caggaccctg | ccctcctagg | 720 |
| ggctgttcga | atgggggcac | ctgccagctg | atgccagaga | aagactccac | cttcacctc | 780 |
| tgcctctgtc | cccaggtttt | cataggcccg | gctgtgaggt | gaatccaga | caactgtgtc | 840 |
| agccaccaat | gtcagaatgg | gggcacttgc | caggatgggc | tggacacta | cacctgcctc | 900 |
| tgcccagaaa | cctggacagg | ctgggactgc | tccgaagatg | tggatgagtg | tgaggcccag | 960 |
| ggtcccccctc | actgcagaaa | cggggggcacc | tgccagaact | ctgctggtag | ctttcactgc | 1020 |
| gtgtgtgtga | gtggctgggg | gggcacaagc | tgtgaggaga | acctggatga | ctgtattgct | 1080 |
| gccacctgtg | ccccgggatc | cacctgcatt | gaccgggtgg | gctctttctc | ctgcctctgc | 1140 |
| ccacctggac | gcacaggact | cctgtgccac | ttggaagaca | tgtgtctgag | ccagccgtgc | 1200 |
| catggggatg | cccaatgcag | caccaacccc | ctcacaggct | ccacactctg | cctgtgtcag | 1260 |
| cctggctatt | cggggcccac | ctgccaccag | gacctggacg | agtgtctgat | ggcccagcaa | 1320 |
| ggcccaagtc | cctgtgaaca | tggcggttcc | tgcctcaaca | ctcctggctc | cttcaactgc | 1380 |
| ctctgtccac | ctggctacac | aggctcccgt | tgtgaggctg | atcacaatga | gtgcctctcc | 1440 |
| cagccctgcc | acccaggaag | cacctgtctg | gacttacttg | ccaccttcca | ctgcctctgc | 1500 |
| ccgccaggct | tagaagggca | gctctgtgag | gtggagacca | acgagtgtgc | ctcagctccc | 1560 |
| tgcctgaacc | acgcggattg | ccatgacctg | ctcaacggct | tccagtgcat | ctgcctgcct | 1620 |
| ggattctccg | gcacccgatg | tgaggaggat | atcgatgagt | gcagaagctc | tcctgtgcc | 1680 |
| aatggtgggc | agtgccagga | ccagcctgga | gccttccact | gcaagtgtct | cccaggcttt | 1740 |
| gaagggccac | gctgtcaaac | agaggtggat | gagtgcctga | gtgacccatg | tccgttgga | 1800 |

```
gccagctgcc ttgatcttcc aggagccttc ttttgcctct gcccctctgg tttcacaggc   1860
cagctctgtg aggttcccct gtgtgctccc aacctgtgcc agcccaagca gatatgtaag   1920
gaccagaaag acaaggccaa ctgcctctgt cctgatggaa gccctggctg tgccccacct   1980
gaggacaact gcacctgcca ccacgggcac tgccagagat cctcatgtgt gtgtgacgtg   2040
ggttggacgg ggccagagtg tgaggcagag ctaggggggct gcatctctgc accctgtgcc   2100
catgggggga cctgctaccc ccagccctct ggctacaact gcacctgccc tacaggctac   2160
acaggaccca cctgtagtga ggagatgaca gcttgtcact cagggccatg tctcaatggc   2220
ggctcctgca accctagccc tggaggctac tactgcacct gccctccaag ccacacaggg   2280
ccccagtgcc aaaccagcac tgactactgt gtgtctgccc cgtgcttcaa tgggggtacc   2340
tgtgtgaaca ggcctggcac cttctcctgc ctctgtgcca tgggcttcca gggcccgcgc   2400
tgtgagggaa agctccgccc cagctgtgca gacagcccct gtaggaatag gcaacctgc    2460
caggacagcc ctcagggtcc ccgctgcctc tgccccactg gctacaccgg aggcagctgc   2520
cagactctga tggacttatg tgcccagaag ccctgcccac gcaattccca ctgcctccag   2580
actgggccct ccttccactg cttgtgcctc caggatggaa ccgggcctct ctgcaacctt   2640
ccactgtcct cctgccagaa ggctgcactg agccaaggca tagacgtctc ttccctttgc   2700
cacaatggag gctctgtgt cgacagcggc ccctcctatt tctgccactg ccccctgga    2760
ttccaaggca gcctgtgcca ggatcacgtg aacccatgtg agtccaggcc ttgccagaac   2820
ggggccacct gcatggccca gcccagtggg tatctctgcc agtgtgcccc aggctacgat   2880
ggacagaact gctcaaagga actcgatgct tgtcagtccc aaccctgtca caaccatgga   2940
acctgtactc ccaaacctgg aggcttccac tgtgcctgcc ctccaggctt gtgggggcta   3000
cgctgtgagg gagacgtgga cgagtgtctg gaccagccct gccaccccac aggcactgca   3060
gcctgccact ctctggccaa tgccttctac tgccagtgtc tgcctggaca cacaggccag   3120
tggtgtgagg tggagataga cccctgccac agccaaccct gctttcatgg agggacctgt   3180
gaggccacag caggatcacc cctgggtttc atctgccact gccccaaggg ttttgaaggc   3240
cccacctgca gccacagggc cccttcctgc ggcttccatc actgccacca cggaggcctg   3300
tgtctgccct cccctaagcc aggcttccca ccacgctgtg cctgcctcag tggctatggg   3360
ggtcctgact gcctgacccc accagctcct aaaggctgtg gccctccctc ccatgccta   3420
tacaatggca gctgctcaga gaccacgggc ttgggggggcc caggctttcg atgctcctgc   3480
cctcacagct ctccagggcc ccggtgtcag aaacccggag ccaaggggtg tgagggcaga   3540
agtggagatg gggcctgcga tgctggctgc agtggcccgg gaggaaactg ggatggaggg   3600
gactgctctc tgggagtccc agaccctgg aagggctgcc cctcccactc tcggtgctgg   3660
cttctcttcc gggacgggca gtgccaccca cagtgtgact ctgaagagtg tctgtttgat   3720
ggctacgact gtgagacccc tccagcctgc actccagcct atgaccagta ctgccatgat   3780
cacttccaca acgggcactg tgagaaaggc tgcaacactg cagagtgtgg ctggatgga    3840
ggtgactgca ggcctgaaga tgggaccca gagtgggggc cctccctggc cctgctggtg   3900
gtactgagcc ccccagccct agaccagcag ctgtttgccc tggcccgggt gctgtccctg   3960
actctgaggg taggactctg ggtaaggaag atcgtgatg gcaggacat ggtgtacccc    4020
tatcctgggg cccgggctga agaaaagcta ggaggaactc gggacccac ctatcaggag   4080
agagcagccc ctcaaacaca gcccctgggc aaggagaccg actccctcag tgctgggttt   4140
gtggtggtca tgggtgtgga tttgtcccgc tgtggccctg accacccggc atcccgctgt   4200
```

```
cctgggacc ctgggcttct actccgcttc cttgctgcga tggctgcagt gggagccctg    4260
gagcccctgc tgcctggacc actgctggct gtccaccctc atgcagggac cgcaccccct    4320
gccaaccagc ttccctggcc tgtgctgtgc tccccagtgg ccggggtgat tctcctggcc    4380
ctagggctc ttctcgtcct ccagctcatc cggcgtcgac gccgagagca tggagctctc    4440
tggctgcccc ctggtttcac tcgacggcct cggactcagt cagctccca ccgacgccgg    4500
cccccactag gcgaggacag cattggtctc aaggcactga agccaaaggc agaagttgat    4560
gaggatggag ttgtgatgtg ctcaggccct gaggagggag aggaggtggg ccaggctgaa    4620
gaaacaggcc caccctccac gtgccagctc tggtctctga gtggtggctg tggggcgctc    4680
cctcaggcag ccatgctaac tcctccccag gaatctgaga tggaagcccc tgacctggac    4740
acccgtggac ctgatggggt gacaccctg atgtcagcag tttgctgtgg ggaagtacag    4800
tccgggacct tccaaggggc atggttggga tgtcctgagc cctgggaacc tctgctggat    4860
ggaggggcct gtccccaggc tcacaccgtg gcactgggg agaccccct gcacctggct    4920
gcccgattct cccggccaac cgctgcccgc cgcctccttg aggctggagc aaccccaac    4980
cagccagacc gggcagggcg cacacccctt catgctgctg tggctgctga tgctcggag    5040
gtctgccagc ttctgctccg tagcagacaa actgcagtgg acgctcgcac agaggacggg    5100
accacaccct tgatgctggc tgccaggctg gcggtggaag acctggttga agaactgatt    5160
gcagcccaag cagacgtggg ggcagagat aaatggggga aaactgcgct gcactgggct    5220
gctgccgtga caacgcccg agccgcccgc tcgcttctcc aggccggagc cgataaagat    5280
gcccaggaca acagggagca gacgccgcta ttcctggcgg cgcgggaagg agcggtggaa    5340
gtagcccagc tactgctggg gctggggca gcccagagc tgcgggacca ggctgggcta    5400
gcgccggcgg acgtcgctca ccaacgtaac cactgggatc tgctgacgct gctggaaggg    5460
gctgggccac cagaggcccg tcacaaagcc acgccgggcc gcgaggctgg gcccttcccg    5520
cgcgcacgga cggtgtcagt aagcgtgccc ccgcatgggg gcgggctct gccgcgctgc    5580
cggacgctgt cagccggagc aggccctcgt ggggcggag cttgtctgca ggctcggact    5640
tggtccgtag acttggctgc gcggggggc ggggcctatt ctcattgccg gagcctctcg    5700
ggagtaggag caggaggagg cccgacccct cgcggccgta ggttttctgc aggcatgcgc    5760
gggcctcggc ccaaccctgc gataatgcga ggaagatacg gagtggctgc cgggcgcgga    5820
ggcagggtct caacggatga ctggcccgt gattgggtgg ccctgggagc ttgcggttct    5880
gcctccaaca ttccgatccc gcctccttgc cttactccgt ccccggagcg gggatcacct    5940
caacttgact gtggtccccc agccctccaa gaaatgccca taaccaagg aggagagggt    6000
aaaaaatag                                                              6009
```

<210> SEQ ID NO 8
<211> LENGTH: 2003
<212> TYPE: PRT
<213> ORGANISM: Homo sapiens

<400> SEQUENCE: 8

```
Met Gln Pro Pro Ser Leu Leu Leu Leu Leu Leu Leu Leu Leu
  1               5                  10                  15

Cys Val Ser Val Val Arg Pro Arg Gly Leu Leu Cys Gly Ser Phe Pro
             20                  25                  30

Glu Pro Cys Ala Asn Gly Gly Thr Cys Leu Ser Leu Ser Leu Gly Gln
         35                  40                  45
```

```
Gly Thr Cys Gln Cys Ala Pro Gly Phe Leu Gly Glu Thr Cys Gln Phe
 50                  55                  60

Pro Asp Pro Cys Gln Asn Ala Gln Leu Cys Gln Asn Gly Gly Ser Cys
 65                  70                  75                  80

Gln Ala Leu Leu Pro Ala Pro Leu Gly Leu Pro Ser Ser Pro Ser Pro
                 85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
            115                 120                 125

Lys Arg Gly Arg Cys His Ile Gln Ala Ser Gly Arg Pro Gln Cys Ser
130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
            195                 200                 205

Thr Ser Cys His Asn Thr Leu Gly Ser Phe Gln Cys Leu Cys Pro Val
210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
            275                 280                 285

Gly Thr Cys Gln Asp Gly Leu Asp Thr Tyr Thr Cys Leu Cys Pro Glu
            290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
            355                 360                 365

Thr Cys Ile Asp Arg Val Gly Ser Phe Ser Cys Leu Cys Pro Pro Gly
370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
            435                 440                 445

Gly Gly Ser Cys Leu Asn Thr Pro Gly Ser Phe Asn Cys Leu Cys Pro
            450                 455                 460

Pro Gly Tyr Thr Gly Ser Arg Cys Glu Ala Asp His Asn Glu Cys Leu
465                 470                 475                 480
```

```
Ser Gln Pro Cys His Pro Gly Ser Thr Cys Leu Asp Leu Leu Ala Thr
            485                 490                 495

Phe His Cys Leu Cys Pro Pro Gly Leu Glu Gly Gln Leu Cys Glu Val
        500                 505                 510

Glu Thr Asn Glu Cys Ala Ser Ala Pro Cys Leu Asn His Ala Asp Cys
    515                 520                 525

His Asp Leu Leu Asn Gly Phe Gln Cys Ile Cys Leu Pro Gly Phe Ser
530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
            580                 585                 590

Cys Leu Ser Asp Pro Cys Pro Val Gly Ala Ser Cys Leu Asp Leu Pro
        595                 600                 605

Gly Ala Phe Phe Cys Leu Cys Pro Ser Gly Phe Thr Gly Gln Leu Cys
    610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
            660                 665                 670

Gln Arg Ser Ser Cys Val Cys Asp Val Gly Trp Thr Gly Pro Glu Cys
        675                 680                 685

Glu Ala Glu Leu Gly Gly Cys Ile Ser Ala Pro Cys Ala His Gly Gly
    690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr Tyr
            740                 745                 750

Cys Thr Cys Pro Pro Ser His Thr Gly Pro Gln Cys Gln Thr Ser Thr
        755                 760                 765

Asp Tyr Cys Val Ser Ala Pro Cys Phe Asn Gly Gly Thr Cys Val Asn
    770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
                805                 810                 815

Asn Arg Ala Thr Cys Gln Asp Ser Pro Gln Gly Pro Arg Cys Leu Cys
            820                 825                 830

Pro Thr Gly Tyr Thr Gly Gly Ser Cys Gln Thr Leu Met Asp Leu Cys
        835                 840                 845

Ala Gln Lys Pro Cys Pro Arg Asn Ser His Cys Leu Gln Thr Gly Pro
    850                 855                 860

Ser Phe His Cys Leu Cys Leu Gln Gly Trp Thr Gly Pro Leu Cys Asn
865                 870                 875                 880

Leu Pro Leu Ser Ser Cys Gln Lys Ala Ala Leu Ser Gln Gly Ile Asp
                885                 890                 895

Val Ser Ser Leu Cys His Asn Gly Gly Leu Cys Val Asp Ser Gly Pro
```

```
                    900             905             910
Ser Tyr Phe Cys His Cys Pro Pro Gly Phe Gln Gly Ser Leu Cys Gln
            915                 920             925

Asp His Val Asn Pro Cys Glu Ser Arg Pro Cys Gln Asn Gly Ala Thr
            930                 935             940

Cys Met Ala Gln Pro Ser Gly Tyr Leu Cys Gln Cys Ala Pro Gly Tyr
945                 950             955             960

Asp Gly Gln Asn Cys Ser Lys Glu Leu Asp Ala Cys Gln Ser Gln Pro
                965             970             975

Cys His Asn His Gly Thr Cys Thr Pro Lys Pro Gly Gly Phe His Cys
            980             985             990

Ala Cys Pro Pro Gly Phe Val Gly Leu Arg Cys Glu Gly Asp Val Asp
            995             1000            1005

Glu Cys Leu Asp Gln Pro Cys His Pro Thr Gly Thr Ala Ala Cys His
            1010            1015            1020

Ser Leu Ala Asn Ala Phe Tyr Cys Gln Cys Leu Pro Gly His Thr Gly
1025            1030            1035            1040

Gln Trp Cys Glu Val Glu Ile Asp Pro Cys His Ser Gln Pro Cys Phe
            1045            1050            1055

His Gly Gly Thr Cys Glu Ala Thr Ala Gly Ser Pro Leu Gly Phe Ile
            1060            1065            1070

Cys His Cys Pro Lys Gly Phe Glu Gly Pro Thr Cys Ser His Arg Ala
            1075            1080            1085

Pro Ser Cys Gly Phe His His Cys His His Gly Gly Leu Cys Leu Pro
            1090            1095            1100

Ser Pro Lys Pro Gly Phe Pro Pro Arg Cys Ala Cys Leu Ser Gly Tyr
1105            1110            1115            1120

Gly Gly Pro Asp Cys Leu Thr Pro Pro Ala Pro Lys Gly Cys Gly Pro
                1125            1130            1135

Pro Ser Pro Cys Leu Tyr Asn Gly Ser Cys Ser Glu Thr Thr Gly Leu
            1140            1145            1150

Gly Gly Pro Gly Phe Arg Cys Ser Cys Pro His Ser Ser Pro Gly Pro
            1155            1160            1165

Arg Cys Gln Lys Pro Gly Ala Lys Gly Cys Glu Gly Arg Ser Gly Asp
            1170            1175            1180

Gly Ala Cys Asp Ala Gly Cys Ser Gly Pro Gly Gly Asn Trp Asp Gly
1185            1190            1195            1200

Gly Asp Cys Ser Leu Gly Val Pro Asp Pro Trp Lys Gly Cys Pro Ser
                1205            1210            1215

His Ser Arg Cys Trp Leu Leu Phe Arg Asp Gly Gln Cys His Pro Gln
            1220            1225            1230

Cys Asp Ser Glu Glu Cys Leu Phe Asp Gly Tyr Asp Cys Glu Thr Pro
            1235            1240            1245

Pro Ala Cys Thr Pro Ala Tyr Asp Gln Tyr Cys His Asp His Phe His
            1250            1255            1260

Asn Gly His Cys Glu Lys Gly Cys Asn Thr Ala Glu Cys Gly Trp Asp
1265            1270            1275            1280

Gly Gly Asp Cys Arg Pro Glu Asp Gly Asp Pro Glu Trp Gly Pro Ser
                1285            1290            1295

Leu Ala Leu Leu Val Val Leu Ser Pro Pro Ala Leu Asp Gln Gln Leu
            1300            1305            1310

Phe Ala Leu Ala Arg Val Leu Ser Leu Thr Leu Arg Val Gly Leu Trp
            1315            1320            1325
```

-continued

Val Arg Lys Asp Arg Asp Gly Arg Asp Met Val Tyr Pro Tyr Pro Gly
1330                1335                1340

Ala Arg Ala Glu Glu Lys Leu Gly Gly Thr Arg Asp Pro Thr Tyr Gln
1345                1350                1355                1360

Glu Arg Ala Ala Pro Gln Thr Gln Pro Leu Gly Lys Glu Thr Asp Ser
            1365                1370                1375

Leu Ser Ala Gly Phe Val Val Met Gly Val Asp Leu Ser Arg Cys
        1380                1385                1390

Gly Pro Asp His Pro Ala Ser Arg Cys Pro Trp Asp Pro Gly Leu Leu
    1395                1400                1405

Leu Arg Phe Leu Ala Ala Met Ala Ala Val Gly Ala Leu Glu Pro Leu
1410                1415                1420

Leu Pro Gly Pro Leu Leu Ala Val His Pro His Ala Gly Thr Ala Pro
1425                1430                1435                1440

Pro Ala Asn Gln Leu Pro Trp Pro Val Leu Cys Ser Pro Val Ala Gly
            1445                1450                1455

Val Ile Leu Leu Ala Leu Gly Ala Leu Leu Val Leu Gln Leu Ile Arg
        1460                1465                1470

Arg Arg Arg Arg Glu His Gly Ala Leu Trp Leu Pro Pro Gly Phe Thr
    1475                1480                1485

Arg Arg Pro Arg Thr Gln Ser Ala Pro His Arg Arg Arg Pro Pro Leu
    1490                1495                1500

Gly Glu Asp Ser Ile Gly Leu Lys Ala Leu Lys Pro Lys Ala Glu Val
1505                1510                1515                1520

Asp Glu Asp Gly Val Val Met Cys Ser Gly Pro Glu Glu Gly Glu Glu
            1525                1530                1535

Val Gly Gln Ala Glu Glu Thr Gly Pro Pro Ser Thr Cys Gln Leu Trp
        1540                1545                1550

Ser Leu Ser Gly Gly Cys Gly Ala Leu Pro Gln Ala Ala Met Leu Thr
    1555                1560                1565

Pro Pro Gln Glu Ser Glu Met Glu Ala Pro Asp Leu Asp Thr Arg Gly
    1570                1575                1580

Pro Asp Gly Val Thr Pro Leu Met Ser Ala Val Cys Cys Gly Glu Val
1585                1590                1595                1600

Gln Ser Gly Thr Phe Gln Gly Ala Trp Leu Gly Cys Pro Glu Pro Trp
            1605                1610                1615

Glu Pro Leu Leu Asp Gly Gly Ala Cys Pro Gln Ala His Thr Val Gly
        1620                1625                1630

Thr Gly Glu Thr Pro Leu His Leu Ala Ala Arg Phe Ser Arg Pro Thr
    1635                1640                1645

Ala Ala Arg Arg Leu Leu Glu Ala Gly Ala Asn Pro Asn Gln Pro Asp
    1650                1655                1660

Arg Ala Gly Arg Thr Pro Leu His Ala Ala Val Ala Ala Asp Ala Arg
1665                1670                1675                1680

Glu Val Cys Gln Leu Leu Leu Arg Ser Arg Gln Thr Ala Val Asp Ala
            1685                1690                1695

Arg Thr Glu Asp Gly Thr Thr Pro Leu Met Leu Ala Ala Arg Leu Ala
        1700                1705                1710

Val Glu Asp Leu Val Glu Glu Leu Ile Ala Gln Ala Asp Val Gly
    1715                1720                1725

Ala Arg Asp Lys Trp Gly Lys Thr Ala Leu His Trp Ala Ala Ala Val
    1730                1735                1740

Asn Asn Ala Arg Ala Ala Arg Ser Leu Leu Gln Ala Gly Ala Asp Lys
1745                1750                1755                1760

-continued

```
Asp Ala Gln Asp Asn Arg Glu Gln Thr Pro Leu Phe Leu Ala Ala Arg
            1765                1770                1775
Glu Gly Ala Val Glu Val Ala Gln Leu Leu Leu Gly Leu Gly Ala Ala
        1780                1785                1790
Arg Glu Leu Arg Asp Gln Ala Gly Leu Ala Pro Ala Asp Val Ala His
        1795                1800                1805
Gln Arg Asn His Trp Asp Leu Leu Thr Leu Leu Glu Gly Ala Gly Pro
        1810                1815                1820
Pro Glu Ala Arg His Lys Ala Thr Pro Gly Arg Glu Ala Gly Pro Phe
1825                1830                1835                1840
Pro Arg Ala Arg Thr Val Ser Val Ser Val Pro His Gly Gly
            1845                1850                1855
Ala Leu Pro Arg Cys Arg Thr Leu Ser Ala Gly Ala Gly Pro Arg Gly
            1860                1865                1870
Gly Gly Ala Cys Leu Gln Ala Arg Thr Trp Ser Val Asp Leu Ala Ala
        1875                1880                1885
Arg Gly Gly Gly Ala Tyr Ser His Cys Arg Ser Leu Ser Gly Val Gly
        1890                1895                1900
Ala Gly Gly Gly Pro Thr Pro Arg Gly Arg Arg Phe Ser Ala Gly Met
1905                1910                1915                1920
Arg Gly Pro Arg Pro Asn Pro Ala Ile Met Arg Gly Arg Tyr Gly Val
            1925                1930                1935
Ala Ala Gly Arg Gly Gly Arg Val Ser Thr Asp Asp Trp Pro Cys Asp
            1940                1945                1950
Trp Val Ala Leu Gly Ala Cys Gly Ser Ala Ser Asn Ile Pro Ile Pro
        1955                1960                1965
Pro Pro Cys Leu Thr Pro Ser Pro Glu Arg Gly Ser Pro Gln Leu Asp
        1970                1975                1980
Cys Gly Pro Pro Ala Leu Gln Glu Met Pro Ile Asn Gln Gly Gly Glu
1985                1990                1995                2000
Gly Lys Lys

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
gaggtccaag ccgaacctg                                                  19

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
atcgctgatg tgcagttcac a                                               21

<210> SEQ ID NO 11
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 11
cgctgccggc ctggattcac                                              20

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
gatgcaagcc cggaagaa                                                18

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
tcgcaattca gaaaggctac tg                                           22

<210> SEQ ID NO 14
<211> LENGTH: 17
<212> TYPE: DNA
<213> ORGANISM: Artificial Sequence
<220> FEATURE:
<223> OTHER INFORMATION: Synthetic

<400> SEQUENCE: 14
cgcagaggga tcataga                                                 17

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
ctacacatcg ccgctttcg                                               19

<210> SEQ ID NO 16
<211> LENGTH: 18
<212> TYPE: DNA
<213> ORGANISM: Artificial Sequence
<220> FEATURE:
<223> OTHER INFORMATION: Synthetic

<400> SEQUENCE: 16
cgcgtacttg gccttggt                                                18

<210> SEQ ID NO 17
<211> LENGTH: 15
<212> TYPE: DNA
<213> ORGANISM: Artificial Sequence
<220> FEATURE:
<223> OTHER INFORMATION: Synthetic

<400> SEQUENCE: 17
ccaccaggac atcgt                                                   15

<210> SEQ ID NO 18
<211> LENGTH: 530
<212> TYPE: PRT
```

<213> ORGANISM: Mus musculus

<400> SEQUENCE: 18

```
Met Thr Pro Ala Ser Arg Ser Ala Cys Arg Trp Ala Leu Leu Leu
1               5                   10                  15

Ala Val Leu Trp Pro Gln Gln Arg Ala Ala Gly Ser Gly Ile Phe Gln
            20                  25                  30

Leu Arg Leu Gln Glu Phe Val Asn Gln Arg Gly Met Leu Ala Asn Gly
            35                  40                  45

Gln Ser Cys Glu Pro Gly Cys Arg Thr Phe Phe Arg Ile Cys Leu Lys
50                  55                  60

His Phe Gln Ala Thr Phe Ser Glu Gly Pro Cys Thr Phe Gly Asn Val
65                  70                  75                  80

Ser Thr Pro Val Leu Gly Thr Asn Ser Phe Val Val Arg Asp Lys Asn
                85                  90                  95

Ser Gly Ser Gly Arg Asn Pro Leu Gln Leu Pro Phe Asn Phe Thr Trp
            100                 105                 110

Pro Gly Thr Phe Ser Leu Asn Ile Gln Ala Trp His Thr Pro Gly Asp
        115                 120                 125

Asp Leu Arg Pro Glu Thr Ser Pro Gly Asn Ser Leu Ile Ser Gln Ile
130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
            180                 185                 190

Asp Asp His Phe Gly His Tyr Glu Cys Gln Pro Asp Gly Ser Leu Ser
        195                 200                 205

Cys Leu Pro Gly Trp Thr Gly Lys Tyr Cys Asp Gln Pro Ile Cys Leu
210                 215                 220

Ser Gly Cys His Glu Gln Asn Gly Tyr Cys Ser Lys Pro Asp Glu Cys
225                 230                 235                 240

Ile Cys Arg Pro Gly Trp Gln Gly Arg Leu Cys Asn Glu Cys Ile Pro
                245                 250                 255

His Asn Gly Cys Arg His Gly Thr Cys Ser Ile Pro Trp Gln Cys Ala
            260                 265                 270

Cys Asp Glu Gly Trp Gly Gly Leu Phe Cys Asp Gln Asp Leu Asn Tyr
        275                 280                 285

Cys Thr His His Ser Pro Cys Lys Asn Gly Ser Thr Cys Ser Asn Ser
290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                325                 330                 335

Gly Gly Ser Cys Lys Asp Gln Glu Asn Ser Tyr His Cys Leu Cys Pro
            340                 345                 350

Pro Gly Tyr Tyr Gly Gln His Cys Glu His Ser Thr Leu Thr Cys Ala
        355                 360                 365

Asp Ser Pro Cys Phe Asn Gly Gly Ser Cys Arg Glu Arg Asn Gln Gly
370                 375                 380

Ser Ser Tyr Ala Cys Glu Cys Pro Pro Asn Phe Thr Gly Ser Asn Cys
385                 390                 395                 400

Glu Lys Lys Val Asp Arg Cys Thr Ser Asn Pro Cys Ala Asn Gly Gly
```

```
                        405                 410                 415
Gln Cys Leu Asn Arg Gly Pro Ser Arg Thr Cys Arg Cys Arg Pro Gly
            420                 425                 430

Phe Thr Gly Thr His Cys Glu Leu His Ile Ser Asp Cys Ala Arg Ser
        435                 440                 445

Pro Cys Ala His Gly Gly Thr Cys His Asp Leu Glu Asn Gly Pro Val
    450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                485                 490                 495

Tyr Thr Gly Leu Ser Pro Asn Asn Phe Val Cys Asn Cys Pro Tyr Gly
            500                 505                 510

Phe Val Gly Ser Arg Cys Glu Phe Pro Val Gly Leu Pro Pro Ser Phe
        515                 520                 525

Pro Trp
    530

<210> SEQ ID NO 19
<211> LENGTH: 458
<212> TYPE: PRT
<213> ORGANISM: Artificial Sequence
<220> FEATURE:
<223> OTHER INFORMATION: Synthetic

<400> SEQUENCE: 19

Met Val Ser Tyr Trp Asp Thr Gly Val Leu Leu Cys Ala Leu Leu Ser
1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240
```

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
        260                 265                 270

Val Val Val Asp Val Ser His Glu Asp Pro Glu Val Lys Phe Asn Trp
275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 20
<211> LENGTH: 227
<212> TYPE: PRT
<213> ORGANISM: Homo sapiens

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 21
<211> LENGTH: 272
<212> TYPE: PRT
<213> ORGANISM: Artificial Sequence
<220> FEATURE:
<223> OTHER INFORMATION: Synthetic

<400> SEQUENCE: 21

Val Ile Cys Ser Asp Asn Tyr Tyr Gly Asp Asn Cys Ser Arg Leu Cys
1               5                   10                  15

Lys Lys Arg Asn Asp His Phe Gly His Tyr Val Cys Gln Pro Asp Gly
            20                  25                  30

Asn Leu Ser Cys Leu Pro Gly Trp Thr Gly Glu Tyr Cys Asp Lys Thr
        35                  40                  45

His Thr Cys Pro Pro Cys Pro Ala Pro Glu Leu Leu Gly Gly Pro Ser
    50                  55                  60

Val Phe Leu Phe Pro Pro Lys Pro Lys Asp Thr Leu Met Ile Ser Arg
65                  70                  75                  80

Thr Pro Glu Val Thr Cys Val Val Val Asp Val Ser His Glu Asp Pro
                85                  90                  95

Glu Val Lys Phe Asn Trp Tyr Val Asp Gly Val Glu Val His Asn Ala
            100                 105                 110

Lys Thr Lys Pro Arg Glu Glu Gln Tyr Asn Ser Thr Tyr Arg Val Val
        115                 120                 125

Ser Val Leu Thr Val Leu His Gln Asp Trp Leu Asn Gly Lys Glu Tyr
    130                 135                 140

Lys Cys Lys Val Ser Asn Lys Ala Leu Pro Ala Pro Ile Glu Lys Thr
145                 150                 155                 160

Ile Ser Lys Ala Lys Gly Gln Pro Arg Glu Pro Gln Val Tyr Thr Leu
                165                 170                 175

Pro Pro Ser Arg Asp Glu Leu Thr Lys Asn Gln Val Ser Leu Thr Cys
            180                 185                 190

Leu Val Lys Gly Phe Tyr Pro Ser Asp Ile Ala Val Glu Trp Glu Ser
        195                 200                 205

Asn Gly Gln Pro Glu Asn Asn Tyr Lys Thr Thr Pro Pro Val Leu Asp
    210                 215                 220

Ser Asp Gly Ser Phe Phe Leu Tyr Ser Lys Leu Thr Val Asp Lys Ser
225                 230                 235                 240

Arg Trp Gln Gln Gly Asn Val Phe Ser Cys Ser Val Met His Glu Ala
                245                 250                 255

Leu His Asn His Tyr Thr Gln Lys Ser Leu Ser Leu Ser Pro Gly Lys
            260                 265                 270

<210> SEQ ID NO 22
<211> LENGTH: 418

```
<212> TYPE: PRT
<213> ORGANISM: Artificial Sequence
<220> FEATURE:
<223> OTHER INFORMATION: Synthetic

<400> SEQUENCE: 22

Ser Gly Val Phe Gln Leu Gln Leu Gln Glu Phe Ile Asn Glu Arg Gly
  1               5                  10                  15

Val Leu Ala Ser Gly Arg Pro Cys Glu Pro Gly Cys Arg Thr Phe Phe
             20                  25                  30

Arg Val Cys Leu Lys His Phe Gln Ala Val Val Ser Pro Gly Pro Cys
         35                  40                  45

Thr Phe Gly Thr Val Ser Thr Pro Val Leu Gly Thr Asn Ser Phe Ala
 50                  55                  60

Val Arg Asp Asp Ser Ser Gly Gly Arg Asn Pro Leu Gln Leu Pro
 65                  70                  75                  80

Phe Asn Phe Thr Trp Pro Gly Thr Phe Ser Leu Ile Ile Glu Ala Trp
                 85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Asp
            180                 185                 190

Lys Thr His Thr Cys Pro Pro Cys Pro Ala Pro Glu Leu Leu Gly Gly
        195                 200                 205

Pro Ser Val Phe Leu Phe Pro Pro Lys Pro Lys Asp Thr Leu Met Ile
210                 215                 220

Ser Arg Thr Pro Glu Val Thr Cys Val Val Val Asp Val Ser His Glu
225                 230                 235                 240

Asp Pro Glu Val Lys Phe Asn Trp Tyr Val Asp Gly Val Glu Val His
                245                 250                 255

Asn Ala Lys Thr Lys Pro Arg Glu Glu Gln Tyr Asn Ser Thr Tyr Arg
            260                 265                 270

Val Val Ser Val Leu Thr Val Leu His Gln Asp Trp Leu Asn Gly Lys
        275                 280                 285

Glu Tyr Lys Cys Lys Val Ser Asn Lys Ala Leu Pro Ala Pro Ile Glu
290                 295                 300

Lys Thr Ile Ser Lys Ala Lys Gly Gln Pro Arg Glu Pro Gln Val Tyr
305                 310                 315                 320

Thr Leu Pro Pro Ser Arg Asp Glu Leu Thr Lys Asn Gln Val Ser Leu
                325                 330                 335

Thr Cys Leu Val Lys Gly Phe Tyr Pro Ser Asp Ile Ala Val Glu Trp
            340                 345                 350

Glu Ser Asn Gly Gln Pro Glu Asn Asn Tyr Lys Thr Thr Pro Pro Val
        355                 360                 365

Leu Asp Ser Asp Gly Ser Phe Phe Leu Tyr Ser Lys Leu Thr Val Asp
370                 375                 380

Lys Ser Arg Trp Gln Gln Gly Asn Val Phe Ser Cys Ser Val Met His
```

```
385                 390                 395                 400
Glu Ala Leu His Asn His Tyr Thr Gln Lys Ser Leu Ser Leu Ser Pro
                405                 410                 415
Gly Lys

<210> SEQ ID NO 23
<211> LENGTH: 410
<212> TYPE: PRT
<213> ORGANISM: Artificial Sequence
<220> FEATURE:
<223> OTHER INFORMATION: Synthetic

<400> SEQUENCE: 23

Gln Gln Pro Ile Cys Leu Ser Gly Cys His Glu Gln Asn Gly Tyr Cys
1               5                   10                  15

Ser Lys Pro Ala Glu Cys Leu Cys Arg Pro Gly Trp Gln Gly Arg Leu
            20                  25                  30

Cys Asn Glu Cys Ile Pro His Asn Gly Cys Arg His Gly Thr Cys Ser
        35                  40                  45

Thr Pro Trp Gln Cys Thr Cys Asp Glu Gly Trp Gly Gly Leu Phe Cys
    50                  55                  60

Asp Gln Asp Leu Asn Tyr Cys Thr His His Ser Pro Cys Lys Asn Gly
65                  70                  75                  80

Ala Thr Cys Ser Asn Ser Gly Gln Arg Ser Tyr Thr Cys Thr Cys Arg
                85                  90                  95

Pro Gly Tyr Thr Gly Val Asp Cys Glu Leu Glu Leu Ser Glu Cys Asp
            100                 105                 110

Ser Asn Pro Cys Arg Asn Gly Gly Ser Cys Lys Asp Gln Glu Asp Gly
        115                 120                 125

Tyr His Cys Leu Cys Pro Pro Gly Tyr Tyr Gly Leu His Cys Glu His
    130                 135                 140

Ser Thr Leu Ser Cys Ala Asp Ser Pro Cys Phe Asn Gly Gly Ser Cys
145                 150                 155                 160

Arg Glu Arg Asn Gln Gly Ala Asn Tyr Ala Cys Glu Cys Pro Pro Asn
                165                 170                 175

Phe Thr Gly Ser Asn Cys Glu Asp Lys Thr His Thr Cys Pro Pro Cys
            180                 185                 190

Pro Ala Pro Glu Leu Leu Gly Gly Pro Ser Val Phe Leu Phe Pro Pro
        195                 200                 205

Lys Pro Lys Asp Thr Leu Met Ile Ser Arg Thr Pro Glu Val Thr Cys
    210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
                245                 250                 255

Glu Gln Tyr Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
        275                 280                 285

Lys Ala Leu Pro Ala Pro Ile Glu Lys Thr Ile Ser Lys Ala Lys Gly
    290                 295                 300

Gln Pro Arg Glu Pro Gln Val Tyr Thr Leu Pro Pro Ser Arg Asp Glu
305                 310                 315                 320

Leu Thr Lys Asn Gln Val Ser Leu Thr Cys Leu Val Lys Gly Phe Tyr
                325                 330                 335
```

-continued

```
Pro Ser Asp Ile Ala Val Glu Trp Glu Ser Asn Gly Gln Pro Glu Asn
                340                 345                 350

Asn Tyr Lys Thr Thr Pro Pro Val Leu Asp Ser Asp Gly Ser Phe Phe
            355                 360                 365

Leu Tyr Ser Lys Leu Thr Val Asp Lys Ser Arg Trp Gln Gln Gly Asn
370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
                405                 410

<210> SEQ ID NO 24
<211> LENGTH: 370
<212> TYPE: PRT
<213> ORGANISM: Artificial Sequence
<220> FEATURE:
<223> OTHER INFORMATION: Synthetic

<400> SEQUENCE: 24

Gln Gln Pro Ile Cys Leu Ser Gly Cys His Glu Gln Asn Gly Tyr Cys
1               5                   10                  15

Ser Lys Pro Ala Glu Cys Leu Cys Arg Pro Gly Trp Gln Gly Arg Leu
            20                  25                  30

Cys Asn Glu Cys Ile Pro His Asn Gly Cys Arg His Gly Thr Cys Ser
        35                  40                  45

Thr Pro Trp Gln Cys Thr Cys Asp Glu Gly Trp Gly Gly Leu Phe Cys
    50                  55                  60

Asp Gln Asp Leu Asn Tyr Cys Thr His His Ser Pro Cys Lys Asn Gly
65                  70                  75                  80

Ala Thr Cys Ser Asn Ser Gly Gln Arg Ser Tyr Thr Cys Thr Cys Arg
                85                  90                  95

Pro Gly Tyr Thr Gly Val Asp Cys Glu Leu Glu Leu Ser Glu Cys Asp
            100                 105                 110

Ser Asn Pro Cys Arg Asn Gly Gly Ser Cys Lys Asp Gln Glu Asp Gly
        115                 120                 125

Tyr His Cys Leu Cys Pro Pro Gly Tyr Tyr Gly Leu His Cys Glu Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
```

```
            290                 295                 300
Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
                340                 345                 350

Glu Ala Leu His Asn His Tyr Thr Gln Lys Ser Leu Ser Leu Ser Pro
            355                 360                 365

Gly Lys
    370

<210> SEQ ID NO 25
<211> LENGTH: 332
<212> TYPE: PRT
<213> ORGANISM: Artificial Sequence
<220> FEATURE:
<223> OTHER INFORMATION: Synthetic

<400> SEQUENCE: 25

Gln Gln Pro Ile Cys Leu Ser Gly Cys His Glu Gln Asn Gly Tyr Cys
1               5                   10                  15

Ser Lys Pro Ala Glu Cys Leu Cys Arg Pro Gly Trp Gln Gly Arg Leu
            20                  25                  30

Cys Asn Glu Cys Ile Pro His Asn Gly Cys Arg His Gly Thr Cys Ser
        35                  40                  45

Thr Pro Trp Gln Cys Thr Cys Asp Glu Gly Trp Gly Gly Leu Phe Cys
    50                  55                  60

Asp Gln Asp Leu Asn Tyr Cys Thr His His Ser Pro Cys Lys Asn Gly
65                  70                  75                  80

Ala Thr Cys Ser Asn Ser Gly Gln Arg Ser Tyr Thr Cys Thr Cys Arg
                85                  90                  95

Pro Gly Tyr Thr Gly Val Asp Cys Glu Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285
```

Phe Phe Leu Tyr Ser Lys Leu Thr Val Asp Lys Ser Arg Trp Gln Gln
            290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
            325                 330

<210> SEQ ID NO 26
<211> LENGTH: 292
<212> TYPE: PRT
<213> ORGANISM: Artificial Sequence
<220> FEATURE:
<223> OTHER INFORMATION: Synthetic

<400> SEQUENCE: 26

Gln Gln Pro Ile Cys Leu Ser Gly Cys His Glu Gln Asn Gly Tyr Cys
1               5                   10                  15

Ser Lys Pro Ala Glu Cys Leu Cys Arg Pro Gly Trp Gln Gly Arg Leu
            20                  25                  30

Cys Asn Glu Cys Ile Pro His Asn Gly Cys Arg His Gly Thr Cys Ser
        35                  40                  45

Thr Pro Trp Gln Cys Thr Cys Asp Glu Gly Trp Gly Gly Leu Phe Cys
    50                  55                  60

Asp Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Asp Glu Leu Thr Lys Asn Gln Val
    195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290

<210> SEQ ID NO 27
<211> LENGTH: 5862

<212> TYPE: DNA
<213> ORGANISM: Artificial Sequence
<220> FEATURE:
<223> OTHER INFORMATION: Synthetic

<400> SEQUENCE: 27

```
atgccacggc tcctgacgcc cttgctctgc ctaacgctgc tgcccgcgct cgccgcaaga      60
ggcttgagat gctcccagcc aagtgggacc tgcctgaatg gaggtaggtg cgaagtggcc     120
agcggcactg aagcctgtgt ctgcagcgga gcctttgtgg gccaacgatg ccaggactcc     180
aatccttgcc tcagcacacc gtgtaagaat gctggaacgt gccacgttgt ggaccatggt     240
ggcactgtgg attatgcctg cagctgtccc ctgggtttct ctgggcccct ctgcctgaca     300
cctctggaca cgcctgcct ggccaacccc tgccgcaatg ggcacctg tgacctgctc        360
actctcacag agtacaagtg ccgctgccca ccagggtggt caggaaaatc atgtcagcag     420
gctgacccct gtgcctccaa cccctgtgcc aatggtggcc agtgcctgcc ctttgagtct     480
tcatacatct gtcgctgccc gcctggcttc catggcccca cctgcaggca agatgttaat     540
gagtgcagcc agaaccctgg gctgtgccgc catggaggca cctgccacaa tgagatcggc     600
tcctatcgct gtgcctgccg tgccacccat actggtcccc actgtgaact gcccctatgtg    660
ccctgcagcc cctcacctg ccagaatgga ggcacctgcc gtcctacagg ggacaccacc     720
cacgagtgtg cctgcttgcc aggttttgct ggacagaact gtgaagaaaa tgtggatgac    780
tgtccaggaa acaactgcaa gaatgggggt gcctgtgtgg acggcgtgaa tacctacaat    840
tgccgctgcc caccggagtg gacgggtcag tactgtacag aggatgtgga cgaatgtcag    900
ctcatgccca atgcctgcca gaatggcgga acctgccaca cacacacgg cggctacaac    960
tgtgtgtgtg tcaatgggtg gactggcgag gactgcagtg agaacattga tgactgtgcc   1020
agtgccgcct gtttccaggg tgccacttgc cacgaccgtg tggcttcctt ctactgcgaa   1080
tgtccgcatg gcgcacagg tctgctgtgc cacctcaacg atgcgtgcat cagcaacccc   1140
tgcaacgagg gctccaactg tgacaccaac cctgtcaacg gcaaagccat ctgcacctgc   1200
ccctcggggt acacagggcc agcctgcagc caggacgtgg atgagtgtgc tctgggtgcc   1260
aacccttgtg agcacgcagg caaatgcctc aacacactgg gttctttttga gtgccagtgt   1320
ctacagggct cacgggacc ccgctgtgag attgatgtta atgagtgcat ctccaaccca   1380
tgtcagaatg atgccacttg cctggaccag attggggagt ccaatgcat atgtatgcca    1440
ggttatgaag gtgtatactg tgaaatcaac acggatgagt cgccagcag ccccgtctg    1500
cacaatggcc actgcatgga caagatcaat gagttccaat gtcagtgccc caaaggcttc   1560
aacgggcacc tgtgccagta tgatgtggat gagtgtgcca gcaccatg caagaacggt    1620
gccaagtgcc tggatgggcc caacacctat acctgcgtgt gtacagaagg ttacacaggg   1680
acccactgcg aagtggacat tgacgagtgt gaccctgacc cctgccacta tggttcctgt   1740
aaggatggtg tggccacctt tacctgcctg tgccagccag gctacacagg ccatcactgt   1800
gagaccaaca tcaatgagtg ccacagccaa ccgtgccgcc atgggggcac ctgccaggac   1860
cgtgacaact cctacctctg cttatgcctc aagggaacca cagggcccaa ctgtgagatc   1920
aacctggatg actgcgccag caacccctgt gactctggca cctgtctgga caagattgat   1980
ggctacgaat gtcctgtga accaggctac acaggaagca tgtgtaacgt caacattgac   2040
gaatgtgcgg gcagcccctg ccacaacggg ggcacttgtg aggatggcat cgcgggcttc   2100
acttgccgct gccccgaggg ctaccatgac cccacgtgcc tgtccgaggt caacgagtgc   2160
aacagtaacc cctgcatcca cggagcttgc cgggatggcc tcaatgggta caagtgtgac   2220
```

```
tgtgccctg ggtggagtgg aacaaactgt gacatcaaca acaacgagtg tgagtccaac    2280
ccttgtgtca acggtggcac ctgcaaggac atgaccagtg gctacgtatg cacctgccga    2340
gaaggcttca gtggcctaa ttgccagacc aacatcaacg aatgtgcctc caacccctgc     2400
ctgaaccagg ggacctgcat tgatgatgtc gctggataca agtgcaactg tcctctgcca    2460
tatacaggag ccacgtgtga ggtggtgttg gccccatgtg ctaccagccc ctgcaaaaac    2520
agcggggtat gcaaggagtc tgaagactat gagagttttt cctgtgtctg tcccacaggc   2580
tggcaaggtc aaacctgcga ggttgacatc aatgagtgtg tgaaaagccc atgtcgccat    2640
ggggcctcct gccagaacac caatggcagc taccgctgcc tctgccaggc cggctataca   2700
ggtcgcaact gtgagagtga catcgatgac tgccgcccca cccgtgtca caatgggggt    2760 tcctgcaccg atggcatcaa cacagccttc tgcgactgcc tgccccggctt ccagggtgcc  2820 ttctgtgagg aggacatcaa tgaatgtgcc agcaatccct gccaaaatgg tgccaattgc   2880
actgactgtg tggacagcta cacatgtacc tgccccgtgg gcttcaatgg catccactgc   2940
gagaacaaca cacctgactg tactgagagc tcctgcttca atggtggtac ctgtgtggat   3000
ggtatcaact ccttcacctg tctgtgtcca cctggcttca cgggcagcta ctgtcagtat   3060
gatgtcaatg agtgtgattc acggccctgt ctgcacggtg gtacctgcca agacagctat   3120
ggtacttata agtgtacctg cccacagggc tacactggtc tcaactgcca gaaccttgtg   3180
cgctggtgcg actcggctcc ctgcaagaat ggtggcaggt gctggcagac caacacgcag   3240
taccactgtg agtgccgcag cggctggact ggcgtcaact gcgacgtgct cagtgtgtcc   3300
tgtgaggtgg ctgcacagaa gcgaggcatt gacgtcactc tcctgtgcca gcatggaggg   3360
ctctgtgtgg atgaggagga taacattac tgccactgcc aggcaggcta cacgggcagc    3420
tactgtgagg acgaggtgga cgagtgctca cctaacccct gccagaatgg agctacctgc   3480
actgactatc tcggcggctt ttcctgcaag tgtgtggctg gctaccatgg gtctaactgc   3540
tcagaggaga tcaacgagtg cctgtcccag ccctgccaga atgggggtac ctgcattgat   3600
ctgaccaact cctacaagtg ttcctgcccc cgggggacac agggtgtaca ctgtgagatc   3660
aatgttgatg actgccatcc ccccttgac cctgcctccc gaagcccaa gtgcttcaac     3720 aatggcaccct gtgtggacca ggtgggtggc tatacctgca cctgcccacc aggcttcgtc  3780
ggggagcggt gtgagggtga tgtcaatgaa tgtctctcca cccctgtga cccacgtggc    3840 acccagaact gtgtgcagcg tgttaatgac ttccactgcg agtgccgggc tggccacact   3900
ggacgccgct gtgagtcagt catcaatggc tgcaggggca accttgcaa gaatggggggt    3960 gtctgtgccg tggcctccaa caccgcccgt ggattcatct gtaggtgccc tgcgggcttc  4020
gagggtgcca catgtgagaa tgatgcccgc acttgtggca gcttacgctg cctcaacggt   4080
ggtacatgca tctcgggccc acgtagtccc acctgcctat gcctgggatc cttcaccggc   4140
cctgagtgcc agttcccagc cagcagcccc tgtgtgggta gcaaccctg ctacaatcag    4200 ggcacctgtg agcccacatc cgagaaccct ttctaccgct gtctatgccc tgccaaattc   4260
aacgggctac tgtgccacat cctggactac agcttcacag gtggcgctgg gcgcgacatt   4320 ccccaccgc agattgagga ggcctgtgag ctgcctgagt gccaggtgga tgcaggcaat    4380
aaggtctgca acctgcagtg taataatcac gcatgtggc gggatggtgg cgactgctcc    4440
ctcaacttca atgacccctg gaagaactgc acgcagtctc tacagtgctg gaagtatttt   4500
agcgacggcc actgtgacag ccagtgcaac tcggccggct gcctctttga tggcttcgac   4560
tgccagctca ccgagggaca gtgcaacccc ctgtatgacc agtactgcaa ggaccacttc   4620
```

```
agtgatggcc actgcgacca gggctgtaac agtgccgaat gtgagtggga tggcctagac    4680
tgtgctgagc atgtacccga gcggctggca gccggcaccc tggtgctggt ggtgctgctt    4740
ccacccgacc agctacggaa caactccttc cactttctgc gggagctcag ccacgtgctg    4800
cacaccaacg tggtcttcaa gcgtgatgcg caaggccagc agatgatctt cccgtactat    4860
ggccacgagg aagagctgcg caagcaccca atcaagcgct ctacagtggg ttgggccacc    4920
tcttcactgc ttcctggtac cagtggtggg cgccagcgca gggagctgga ccccatggac    4980
atccgtggct ccattgtcta cctggagatc gacaaccggc aatgtgtgca gtcatcctcg    5040
cagtgcttcc agagtgccac cgatgtggct gccttcctag gtgctcttgc gtcacttggc    5100
agcctcaata ttccttacaa gattgaggcc gtgaagagtg agccggtgga gcctccgctg    5160
ccctcgcagg gcccgggcga caaaactcac acatgcccac cgtgcccagc acctgaactc    5220
ctggggggac cgtcagtctt cctcttcccc caaaaccca aggacaccct catgatctcc    5280
cggacccctg aggtcacatg cgtggtggtg gacgtgagcc acgaagaccc tgaggtcaag    5340
ttcaactggt acgtggacgg cgtggaggtg cataatgcca agacaaagcc gcgggaggag    5400
cagtacaaca gcacgtaccg tgtggtcagc gtcctcaccg tcctgcacca ggactggctg    5460
aatggcaagg agtacaagtg caaggtctcc aacaaagccc tcccagcccc catcgagaaa    5520
accatctcca aagccaaagg gcagccccga gaaccacagg tgtacaccct gcccccatcc    5580
cgggatgagc tgaccaagaa ccaggtcagc ctgacctgcc tggtcaaagg cttctatccc    5640
agcgacatcg ccgtggagtg ggagagcaat gggcagccgg agaacaacta caagaccacg    5700
cctcccgtgc tggactccga cggctccttc ttcctctata gcaagctcac cgtggacaag    5760
agcaggtggc agcaggggaa cgtcttctca tgctccgtga tgcatgaggc tctgcacaac    5820
cactacacgc agaagagcct ctccctgtct ccgggtaaat ga                       5862
```

<210> SEQ ID NO 28
<211> LENGTH: 1953
<212> TYPE: PRT
<213> ORGANISM: Artificial Sequence
<220> FEATURE:
<223> OTHER INFORMATION: Synthetic

<400> SEQUENCE: 28

```
Met Pro Arg Leu Leu Thr Pro Leu Leu Cys Leu Thr Leu Leu Pro Ala
  1               5                  10                  15

Leu Ala Ala Arg Gly Leu Arg Cys Ser Gln Pro Ser Gly Thr Cys Leu
             20                  25                  30

Asn Gly Gly Arg Cys Glu Val Ala Ser Gly Thr Glu Ala Cys Val Cys
         35                  40                  45

Ser Gly Ala Phe Val Gly Gln Arg Cys Gln Asp Ser Asn Pro Cys Leu
     50                  55                  60

Ser Thr Pro Cys Lys Asn Ala Gly Thr Cys His Val Val Asp His Gly
 65                  70                  75                  80

Gly Thr Val Asp Tyr Ala Cys Ser Cys Pro Leu Gly Phe Ser Gly Pro
                 85                  90                  95

Leu Cys Leu Thr Pro Leu Asp Asn Ala Cys Leu Ala Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140
```

```
Ala Ser Asn Pro Cys Ala Asn Gly Gly Gln Cys Leu Pro Phe Glu Ser
145                 150                 155                 160

Ser Tyr Ile Cys Arg Cys Pro Pro Gly Phe His Gly Pro Thr Cys Arg
                165                 170                 175

Gln Asp Val Asn Glu Cys Ser Gln Asn Pro Gly Leu Cys Arg His Gly
            180                 185                 190

Gly Thr Cys His Asn Glu Ile Gly Ser Tyr Arg Cys Ala Cys Arg Ala
        195                 200                 205

Thr His Thr Gly Pro His Cys Glu Leu Pro Tyr Val Pro Cys Ser Pro
    210                 215                 220

Ser Pro Cys Gln Asn Gly Gly Thr Cys Arg Pro Thr Gly Asp Thr Thr
225                 230                 235                 240

His Glu Cys Ala Cys Leu Pro Gly Phe Ala Gly Gln Asn Cys Glu Glu
                245                 250                 255

Asn Val Asp Asp Cys Pro Gly Asn Asn Cys Lys Asn Gly Gly Ala Cys
                260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe Gln Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ala Leu Gly Ala Asn Pro Cys Glu His Ala Gly Lys Cys Leu Asn Thr
                420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Ile Ser Asn Pro Cys Gln Asn Asp
    450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
                485                 490                 495

Ser Pro Cys Leu His Asn Gly His Cys Met Asp Lys Ile Asn Glu Phe
                500                 505                 510

Gln Cys Gln Cys Pro Lys Gly Phe Asn Gly His Leu Cys Gln Tyr Asp
            515                 520                 525

Val Asp Glu Cys Ala Ser Thr Pro Cys Lys Asn Gly Ala Lys Cys Leu
            530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575
```

```
Tyr Gly Ser Cys Lys Asp Gly Val Ala Thr Phe Thr Cys Leu Cys Gln
                580                 585                 590

Pro Gly Tyr Thr Gly His His Cys Glu Thr Asn Ile Asn Glu Cys His
            595                 600                 605

Ser Gln Pro Cys Arg His Gly Gly Thr Cys Gln Asp Arg Asp Asn Ser
        610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Val Asn Ile Asp Glu Cys Ala Gly Ser Pro Cys His
        675                 680                 685

Asn Gly Gly Thr Cys Glu Asp Gly Ile Ala Gly Phe Thr Cys Arg Cys
    690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
            820                 825                 830

Cys Ala Thr Ser Pro Cys Lys Asn Ser Gly Val Cys Lys Glu Ser Glu
        835                 840                 845

Asp Tyr Glu Ser Phe Ser Cys Val Cys Pro Thr Gly Trp Gln Gly Gln
    850                 855                 860

Thr Cys Glu Val Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                885                 890                 895

Ala Gly Tyr Thr Gly Arg Asn Cys Glu Ser Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Gln Gly Ala Phe Cys Glu Glu
    930                 935                 940

Asp Ile Asn Glu Cys Ala Ser Asn Pro Cys Gln Asn Gly Ala Asn Cys
945                 950                 955                 960

Thr Asp Cys Val Asp Ser Tyr Thr Cys Thr Cys Pro Val Gly Phe Asn
                965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
```

```
              995                 1000                1005
Cys Pro Gly Phe Thr Gly Ser Tyr Cys Gln Tyr Asp Val Asn Glu
    1010                1015                1020
Cys Asp Ser Arg Pro Cys Leu His Gly Gly Thr Cys Gln Asp Ser Tyr
1025                1030                1035                1040
Gly Thr Tyr Lys Cys Thr Cys Pro Gln Gly Tyr Thr Gly Leu Asn Cys
            1045                1050                1055
Gln Asn Leu Val Arg Trp Cys Ser Ala Pro Cys Lys Asn Gly Gly
        1060                1065                1070
Arg Cys Trp Gln Thr Asn Thr Gln Tyr His Cys Glu Cys Arg Ser Gly
    1075                1080                1085
Trp Thr Gly Val Asn Cys Asp Val Leu Ser Val Ser Cys Glu Val Ala
1090                1095                1100
Ala Gln Lys Arg Gly Ile Asp Val Thr Leu Leu Cys Gln His Gly Gly
1105                1110                1115                1120
Leu Cys Val Asp Glu Gly Asp Lys His Tyr Cys His Cys Gln Ala Gly
            1125                1130                1135
Tyr Thr Gly Ser Tyr Cys Glu Asp Glu Val Asp Glu Cys Ser Pro Asn
        1140                1145                1150
Pro Cys Gln Asn Gly Ala Thr Cys Thr Asp Tyr Leu Gly Gly Phe Ser
    1155                1160                1165
Cys Lys Cys Val Ala Gly Tyr His Gly Ser Asn Cys Ser Glu Glu Ile
    1170                1175                1180
Asn Glu Cys Leu Ser Gln Pro Cys Gln Asn Gly Gly Thr Cys Ile Asp
1185                1190                1195                1200
Leu Thr Asn Ser Tyr Lys Cys Ser Cys Pro Arg Gly Thr Gln Gly Val
            1205                1210                1215
His Cys Glu Ile Asn Val Asp Asp Cys His Pro Pro Leu Asp Pro Ala
        1220                1225                1230
Ser Arg Ser Pro Lys Cys Phe Asn Asn Gly Thr Cys Val Asp Gln Val
        1235                1240                1245
Gly Gly Tyr Thr Cys Thr Cys Pro Pro Gly Phe Val Gly Glu Arg Cys
    1250                1255                1260
Glu Gly Asp Val Asn Glu Cys Leu Ser Asn Pro Cys Asp Pro Arg Gly
1265                1270                1275                1280
Thr Gln Asn Cys Val Gln Arg Val Asn Asp Phe His Cys Glu Cys Arg
            1285                1290                1295
Ala Gly His Thr Gly Arg Arg Cys Glu Ser Val Ile Asn Gly Cys Arg
        1300                1305                1310
Gly Lys Pro Cys Lys Asn Gly Gly Val Cys Ala Val Ala Ser Asn Thr
    1315                1320                1325
Ala Arg Gly Phe Ile Cys Arg Cys Pro Ala Gly Phe Glu Gly Ala Thr
    1330                1335                1340
Cys Glu Asn Asp Ala Arg Thr Cys Gly Ser Leu Arg Cys Leu Asn Gly
1345                1350                1355                1360
Gly Thr Cys Ile Ser Gly Pro Arg Ser Pro Thr Cys Leu Cys Leu Gly
            1365                1370                1375
Ser Phe Thr Gly Pro Glu Cys Gln Phe Pro Ala Ser Ser Pro Cys Val
        1380                1385                1390
Gly Ser Asn Pro Cys Tyr Asn Gln Gly Thr Cys Glu Pro Thr Ser Glu
        1395                1400                1405
Asn Pro Phe Tyr Arg Cys Leu Cys Pro Ala Lys Phe Asn Gly Leu Leu
    1410                1415                1420
```

```
Cys His Ile Leu Asp Tyr Ser Phe Thr Gly Gly Ala Gly Arg Asp Ile
1425                1430                1435                1440

Pro Pro Pro Gln Ile Glu Glu Ala Cys Glu Leu Pro Glu Cys Gln Val
                1445                1450                1455

Asp Ala Gly Asn Lys Val Cys Asn Leu Gln Cys Asn Asn His Ala Cys
                1460                1465                1470

Gly Trp Asp Gly Gly Asp Cys Ser Leu Asn Phe Asn Asp Pro Trp Lys
                1475                1480                1485

Asn Cys Thr Gln Ser Leu Gln Cys Trp Lys Tyr Phe Ser Asp Gly His
                1490                1495                1500

Cys Asp Ser Gln Cys Asn Ser Ala Gly Cys Leu Phe Asp Gly Phe Asp
1505                1510                1515                1520

Cys Gln Leu Thr Glu Gly Gln Cys Asn Pro Leu Tyr Asp Gln Tyr Cys
                1525                1530                1535

Lys Asp His Phe Ser Asp Gly His Cys Asp Gln Gly Cys Asn Ser Ala
                1540                1545                1550

Glu Cys Glu Trp Asp Gly Leu Asp Cys Ala Glu His Val Pro Glu Arg
                1555                1560                1565

Leu Ala Ala Gly Thr Leu Val Leu Val Val Leu Leu Pro Pro Asp Gln
                1570                1575                1580

Leu Arg Asn Asn Ser Phe His Phe Leu Arg Glu Leu Ser His Val Leu
1585                1590                1595                1600

His Thr Asn Val Val Phe Lys Arg Asp Ala Gln Gly Gln Gln Met Ile
                1605                1610                1615

Phe Pro Tyr Tyr Gly His Glu Glu Leu Arg Lys His Pro Ile Lys
                1620                1625                1630

Arg Ser Thr Val Gly Trp Ala Thr Ser Ser Leu Leu Pro Gly Thr Ser
                1635                1640                1645

Gly Gly Arg Gln Arg Arg Glu Leu Asp Pro Met Asp Ile Arg Gly Ser
                1650                1655                1660

Ile Val Tyr Leu Glu Ile Asp Asn Arg Gln Cys Val Gln Ser Ser Ser
1665                1670                1675                1680

Gln Cys Phe Gln Ser Ala Thr Asp Val Ala Ala Phe Leu Gly Ala Leu
                1685                1690                1695

Ala Ser Leu Gly Ser Leu Asn Ile Pro Tyr Lys Ile Glu Ala Val Lys
                1700                1705                1710

Ser Glu Pro Val Glu Pro Pro Leu Pro Ser Gln Gly Pro Gly Asp Lys
                1715                1720                1725

Thr His Thr Cys Pro Pro Cys Pro Ala Pro Glu Leu Leu Gly Gly Pro
                1730                1735                1740

Ser Val Phe Leu Phe Pro Pro Lys Pro Lys Asp Thr Leu Met Ile Ser
1745                1750                1755                1760

Arg Thr Pro Glu Val Thr Cys Val Val Val Asp Val Ser His Glu Asp
                1765                1770                1775

Pro Glu Val Lys Phe Asn Trp Tyr Val Asp Gly Val Glu Val His Asn
                1780                1785                1790

Ala Lys Thr Lys Pro Arg Glu Glu Gln Tyr Asn Ser Thr Tyr Arg Val
                1795                1800                1805

Val Ser Val Leu Thr Val Leu His Gln Asp Trp Leu Asn Gly Lys Glu
                1810                1815                1820

Tyr Lys Cys Lys Val Ser Asn Lys Ala Leu Pro Ala Pro Ile Glu Lys
1825                1830                1835                1840

Thr Ile Ser Lys Ala Lys Gly Gln Pro Arg Glu Pro Gln Val Tyr Thr
                1845                1850                1855
```

Leu Pro Pro Ser Arg Asp Glu Leu Thr Lys Asn Gln Val Ser Leu Thr
        1860                1865                1870

Cys Leu Val Lys Gly Phe Tyr Pro Ser Asp Ile Ala Val Glu Trp Glu
    1875                1880                1885

Ser Asn Gly Gln Pro Glu Asn Asn Tyr Lys Thr Thr Pro Pro Val Leu
        1890                1895                1900

Asp Ser Asp Gly Ser Phe Phe Leu Tyr Ser Lys Leu Thr Val Asp Lys
1905                1910                1915                1920

Ser Arg Trp Gln Gln Gly Asn Val Phe Ser Cys Ser Val Met His Glu
        1925                1930                1935

Ala Leu His Asn His Tyr Thr Gln Lys Ser Leu Ser Leu Ser Pro Gly
        1940                1945                1950

Lys

<210> SEQ ID NO 29
<211> LENGTH: 5862
<212> TYPE: DNA
<213> ORGANISM: Artificial Sequence
<220> FEATURE:
<223> OTHER INFORMATION: Synthetic

<400> SEQUENCE: 29

```
atgccgccgc tcctggcgcc cctgctctgc ctggcgctgc tgcccgcgct cgccgcacga      60
ggcccgcgat gctcccagcc cggtgagacc tgcctgaatg gcgggaagtg tgaagcggcc     120
aatggcacgg aggcctgcgt ctgtggcggg gccttcgtgg cccgcgatgc caggaccccc     180
aacccgtgcc tcagcacccc ctgcaagaac gccgggacat gccacgtggt ggaccgcaga     240
ggcgtggcag actatgcctg cagctgtgcc ctgggcttct ctgggcccct ctgcctgaca     300
cccctggaca tgcctgcct caccaacccc tgccgcaacg ggggcacctg cgacctgctc     360
acgctgacgg agtacaagtg ccgctgcccg cccggctggt cagggaaatc gtgccagcag     420
gctgacccgt gcgcctccaa ccctgcgcc aacggtggcc agtgcctgcc cttcgaggcc     480
tcctacatct gccactgccc acccagcttc atgggcccca cctgccggca ggatgtcaac     540
gagtgtggcc agaagcccgg gctttgccgc acggaggca cctgccacaa cgaggtcggc     600
tcctaccgct gcgtctgccg cgccacccac actggcccca actgcgagcg gcccctacgtg     660
ccctgcagcc cctcgccctg ccagaacggg ggcacctgcc gccccacggg cgacgtcacc     720
cacgagtgtg cctgcctgcc aggcttcacc ggccagaact gtgaggaaaa tatcgacgat     780
tgtccaggaa acaactgcaa gaacggggt gcctgtgtgg acggcgtgaa cacctacaac     840
tgccgctgcc cgccagagtg gacaggtcag tactgtaccg aggatgtgga cgagtgccag     900
ctgatgccaa atgcctgcca gaacggcggg acctgccaca cacccacgg tggctacaac     960
tgcgtgtgtg tcaacggctg gactggtgag gactgcagcg agaacattga tgactgtgcc    1020
agcgccgcct gcttccacgg cgccacctgc catgaccgtg tggcctcctt ctactgcgag    1080
tgtccccatg gccgcacagg tctgctgtgc cacctcaacg acgcatgcat cagcaacccc    1140
tgtaacgagg gctccaactg cgacaccaac cctgtcaatg caaggccat ctgcacctgc    1200
ccctcggggt acacgggccc ggcctgcagc caggacgtgg atgagtgctc gctgggtgcc    1260
aacccctgcg agcatgcggg caagtgcatc aacacgctgg gctccttcga gtgccagtgt    1320
ctgcagggct acacgggccc cgatgcgag atcgacgtca cgagtgcgt ctcgaacccg    1380
tgccagaacg acgccacctg cctggaccag attggggagt ccagtgcat ctgcatgccc    1440
ggctacgagg gtgtgcactg cgaggtcaac acagacgagt gtgccagcag ccctgcctg    1500
```

-continued

```
cacaatggcc gctgcctgga caagatcaat gagttccagt gcgagtgccc cacgggcttc    1560
actgggcatc tgtgccagta cgatgtggac gagtgtgcca gcaccccctg caagaatggt    1620
gccaagtgcc tggacggacc caacacttac acctgtgtgt gcacggaagg gtacacgggg    1680
acgcactgcg aggtggacat cgatgagtgc gaccccgacc cctgccacta cggctcctgc    1740
aaggacggcg tcgccacctt cacctgcctc tgccgcccag gctacacggg ccaccactgc    1800
gagaccaaca tcaacgagtg ctccagccag ccctgccgcc acggggcac ctgccaggac     1860 cgcgacaacg cctacctctg cttctgcctg aagggaccca caggacccaa ctgcgagatc    1920
aacctggatg actgtgccag cagcccctgc gactcgggca cctgtctgga caagatcgat    1980
ggctacgagt gtgcctgtga gccgggctac acagggagca tgtgtaacat caacatcgat    2040
gagtgtgcgg gcaacccctg ccacaacggg ggcacctgcg aggacggcat caatggcttc    2100
acctgccgct gccccgaggg ctaccacgac cccacctgcc tgtctgaggt caatgagtgc    2160
aacagcaacc cctgcgtcca cggggcctgc cgggacagcc tcaacgggta caagtgcgac    2220
tgtgaccctg ggtggagtgg gaccaactgt gacatcaaca acaatgagtg tgaatccaac    2280
ccttgtgtca acgcggcac ctgcaaagac atgaccagtg gctacgtgtg cacctgccgg     2340
gagggcttca gcggtcccaa ctgccagacc aacatcaacg agtgtgcgtc caacccatgt    2400
ctgaaccagg gcacgtgtat tgacgacgtt gccgggtaca agtgcaactg cctgctgccc    2460
tacacaggtg ccacgtgtga ggtggtgctg gccccgtgtg cccccagccc ctgcagaaac    2520
ggcggggagt gcaggcaatc cgaggactat gagagcttct cctgtgtctg ccccacgggc    2580
tggcaagcag ggcagacctg tgaggtcgac atcaacgagt gcgttctgag cccgtgccgg    2640
cacggcgcat cctgccagaa cacccacggc ggctaccgct gccactgcca ggccggctac    2700
agtgggcgca actgcgagac cgacatcgac gactgccggc ccaacccgtg tcacaacggg    2760
ggctcctgca cagacggcat caacacggcc ttctgcgact gcctgccgg cttccggggc     2820 actttctgtg aggaggacat caacgagtgt gccagtgacc cctgccgcaa cggggccaac    2880
tgcacggact gcgtggacag ctacacgtgc acctgccccg caggcttcag cgggatccac    2940
tgtgagaaca acacgcctga ctgcacagag agctcctgct tcaacggtgg cacctgcgtg    3000
gacggcatca actcgttcac ctgcctgtgt ccaccggct tcacgggcag ctactgccag    3060
cacgatgtca atgagtgcga ctcacagccc tgcctgcatg gcggcacctg tcaggacggc    3120
tgcggctcct acaggtgcac ctgcccccag ggctacactg gccccaactg ccagaacctt    3180
gtgcactggt gtgactcctc gccctgcaag aacggcggca aatgctggca gacccacacc    3240
cagtaccgct gcgagtgccc cagcggctgg accggccttt actgcgacgt gcccagcgtg    3300
tcctgtgagg tggctgcgca gcgacaaggt gttgacgttg cccgcctgtg ccagcatgga    3360
gggctctgtg tggacgcggg caacacgcac cactgccgct gccaggcggg ctacacaggc    3420
agctactgtg aggacctggt ggacgagtgc tcacccagcc cctgccagaa cggggccacc    3480
tgcacggact acctgggcgg ctactcctgc aagtgcgtgg ccggctacca cggggtgaac    3540
tgctctgagg agatcgacga gtgcctctcc cacccctgcc agaacggggg cacctgcctc    3600
gacctcccca cacctacaa gtgctcctgc ccacggggca ctcagggtgt gcactgtgag     3660
atcaacgtgg acgactgcaa tccccccgtt gaccccgtgt cccggagccc caagtgccttt    3720 aacaacggca cctgcgtgga ccaggtgggc ggctacagct gcacctgccc gccgggcttc    3780
gtgggtgagc gctgtgaggg ggatgtcaac gagtgcctgt ccaatccctg cgacgcccgt    3840
ggcacccaga actgcgtgca gcgcgtcaat gacttccact gcgagtgccg tgctggtcac    3900
```

```
accgggcgcc gctgcgagtc cgtcatcaat ggctgcaaag gcaagccctg caagaatggg    3960
ggcacctgcg ccgtggcctc aacaccgcc cgcgggttca tctgcaagtg ccctgcgggc    4020
ttcgagggcg ccacgtgtga aatgacgct cgtacctgcg gcagcctgcg ctgcctcaac    4080
ggcggcacat gcatctccgg cccgcgcagc cccacctgcc tgtgcctggg ccccttcacg    4140
ggccccgaat gccagttccc ggccagcagc cctgcctgg gcggcaaccc ctgctacaac    4200
caggggacct gtgagcccac atccgagagc cccttctacc gttgcctgtg ccccgccaaa    4260
ttcaacgggc tcttgtgcca catcctggac tacagcttcg ggggtggggc cgggcgcgac    4320
atccccccgc cgctgatcga ggaggcgtgc gagctgcccg agtgccagga ggacgcgggc    4380
aacaaggtct gcagcctgca gtgcaacaac cacgcgtgcg gctgggacgg cggtgactgc    4440
tccctcaact tcaatgaccc ctggaagaac tgcacgcagt ctctgcagtg ctggaagtac    4500
ttcagtgacg gccactgtga cagccagtgc aactcagccg gctgcctctt cgacggcttt    4560
gactgccagc gtgcggaagg ccagtgcaac ccctgtacg accagtactg caaggaccac    4620
ttcagcgacg ggcactgcga ccagggctgc aacagcgcgg agtgcgagtg ggacgggctg    4680
gactgtgcg agcatgtacc cgagaggctg gcggccggca cgctggtggt ggtggtgctg    4740
atgccgccgg agcagctgcg caacagctcc ttccacttcc tgcgggagct cagccgcgtg    4800
ctgcacacca acgtggtctt caagcgtgac gcacacggcc agcagatgat cttcccctac    4860
tacggccgcg aggaggagct gcgcaagcac cccatcaagc gtgccgccga gggctgggcc    4920
gcacctgacg ccctgctggg ccaggtgaag gcctcgctgc tccctggtgg cagcgagggt    4980
gggcggcggc ggagggagct ggaccccatg gacgtccgcg gctccatcgt ctacctggag    5040
attgacaacc ggcagtgtgt gcaggcctcc tcgcagtgct tccagagtgc accgacgtg    5100
gccgcattcc tgggagcgct cgcctcgctg ggcagcctca acatccccta caagatcgag    5160
gccgtgcagg gccgggcga caaaactcac acatgcccac cgtgcccagc acctgaactc    5220
ctgggggac cgtcagtctt cctcttcccc ccaaaaccca aggacaccct catgatctcc    5280
cggacccctg aggtcacatg cgtggtggtg gacgtgagcc acgaagaccc tgaggtcaag    5340
ttcaactggt acgtggacgg cgtggaggtg cataatgcca agacaaagcc gcgggaggag    5400
cagtacaaca gcacgtaccg tgtggtcagc gtcctcaccg tcctgcacca ggactggctg    5460
aatggcaagg agtacaagtg caaggtctcc aacaaagccc tcccagcccc catcgagaaa    5520
accatctcca aagccaaagg gcagccccga gaaccacagg tgtacaccct gcccccatcc    5580
cgggatgagc tgaccaagaa ccaggtcagc ctgacctgcc tggtcaaagg cttctatccc    5640
agcgacatcg ccgtggagtg ggagagcaat gggcagccgg agaacaacta caagaccacg    5700
cctcccgtgc tggactccga cggctccttc ttcctctata gcaagctcac cgtggacaag    5760
agcaggtggc agcaggggaa cgtcttctca tgctccgtga tgcatgaggc tctgcacaac    5820
cactacacgc agaagagcct ctccctgtct ccgggtaaat ga                      5862
```

<210> SEQ ID NO 30
<211> LENGTH: 1953
<212> TYPE: PRT
<213> ORGANISM: Artificial Sequence
<220> FEATURE:
<223> OTHER INFORMATION: Synthetic

<400> SEQUENCE: 30

Met Pro Pro Leu Leu Ala Pro Leu Leu Cys Leu Ala Leu Leu Pro Ala
1               5                   10                  15

-continued

```
Leu Ala Ala Arg Gly Pro Arg Cys Ser Gln Pro Gly Glu Thr Cys Leu
        20                  25                  30
Asn Gly Gly Lys Cys Glu Ala Ala Asn Gly Thr Glu Ala Cys Val Cys
            35                  40                  45
Gly Gly Ala Phe Val Gly Pro Arg Cys Gln Asp Pro Asn Pro Cys Leu
50                      55                  60
Ser Thr Pro Cys Lys Asn Ala Gly Thr Cys His Val Val Asp Arg Arg
65                  70                  75                  80
Gly Val Ala Asp Tyr Ala Cys Ser Cys Ala Leu Gly Phe Ser Gly Pro
                85                  90                  95
Leu Cys Leu Thr Pro Leu Asp Asn Ala Cys Leu Thr Asn Pro Cys Arg
            100                 105                 110
Asn Gly Gly Thr Cys Asp Leu Leu Thr Leu Thr Glu Tyr Lys Cys Arg
            115                 120                 125
Cys Pro Pro Gly Trp Ser Gly Lys Ser Cys Gln Gln Ala Asp Pro Cys
        130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
            180                 185                 190
Gly Thr Cys His Asn Glu Val Gly Ser Tyr Arg Cys Val Cys Arg Ala
        195                 200                 205
Thr His Thr Gly Pro Asn Cys Glu Arg Pro Tyr Val Pro Cys Ser Pro
210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
            245                 250                 255
Asn Ile Asp Asp Cys Pro Gly Asn Asn Cys Lys Asn Gly Gly Ala Cys
            260                 265                 270
Val Asp Gly Val Asn Thr Tyr Asn Cys Arg Cys Pro Pro Glu Trp Thr
        275                 280                 285
Gly Gln Tyr Cys Thr Glu Asp Val Asp Glu Cys Gln Leu Met Pro Asn
290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
            340                 345                 350
Arg Val Ala Ser Phe Tyr Cys Glu Cys Pro His Gly Arg Thr Gly Leu
        355                 360                 365
Leu Cys His Leu Asn Asp Ala Cys Ile Ser Asn Pro Cys Asn Glu Gly
        370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
            420                 425                 430
Leu Gly Ser Phe Glu Cys Gln Cys Leu Gln Gly Tyr Thr Gly Pro Arg
        435                 440                 445
```

```
Cys Glu Ile Asp Val Asn Glu Cys Val Ser Asn Pro Cys Gln Asn Asp
    450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                    485                 490                 495
Ser Pro Cys Leu His Asn Gly Arg Cys Leu Asp Lys Ile Asn Glu Phe
                500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
                580                 585                 590
Pro Gly Tyr Thr Gly His His Cys Glu Thr Asn Ile Asn Glu Cys Ser
        595                 600                 605
Ser Gln Pro Cys Arg His Gly Gly Thr Cys Gln Asp Arg Asp Asn Ala
    610                 615                 620
Tyr Leu Cys Phe Cys Leu Lys Gly Thr Gly Pro Asn Cys Glu Ile
625                 630                 635                 640
Asn Leu Asp Asp Cys Ala Ser Ser Pro Cys Asp Ser Gly Thr Cys Leu
                645                 650                 655
Asp Lys Ile Asp Gly Tyr Glu Cys Ala Cys Glu Pro Gly Tyr Thr Gly
                660                 665                 670
Ser Met Cys Asn Ile Asn Ile Asp Glu Cys Ala Gly Asn Pro Cys His
        675                 680                 685
Asn Gly Gly Thr Cys Glu Asp Gly Ile Asn Gly Phe Thr Cys Arg Cys
    690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
                725                 730                 735
Tyr Lys Cys Asp Cys Asp Pro Gly Trp Ser Gly Thr Asn Cys Asp Ile
                740                 745                 750
Asn Asn Asn Glu Cys Glu Ser Asn Pro Cys Val Asn Gly Gly Thr Cys
        755                 760                 765
Lys Asp Met Thr Ser Gly Tyr Val Cys Thr Cys Arg Glu Gly Phe Ser
    770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
                805                 810                 815
Cys Leu Leu Pro Tyr Thr Gly Ala Thr Cys Glu Val Val Leu Ala Pro
                820                 825                 830
Cys Ala Pro Ser Pro Cys Arg Asn Gly Gly Glu Cys Arg Gln Ser Glu
        835                 840                 845
Asp Tyr Glu Ser Phe Ser Cys Val Cys Pro Thr Gly Trp Gln Ala Gly
    850                 855                 860
Gln Thr Cys Glu Val Asp Ile Asn Glu Cys Val Leu Ser Pro Cys Arg
```

```
              865                 870                 875                 880
His Gly Ala Ser Cys Gln Asn Thr His Gly Gly Tyr Arg Cys His Cys
                885                 890                 895
Gln Ala Gly Tyr Ser Gly Arg Asn Cys Glu Thr Asp Ile Asp Asp Cys
                900                 905                 910
Arg Pro Asn Pro Cys His Asn Gly Gly Ser Cys Thr Asp Gly Ile Asn
                915                 920                 925
Thr Ala Phe Cys Asp Cys Leu Pro Gly Phe Arg Gly Thr Phe Cys Glu
                930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
                965                 970                 975
Ser Gly Ile His Cys Glu Asn Asn Thr Pro Asp Cys Thr Glu Ser Ser
                980                 985                 990
Cys Phe Asn Gly Gly Thr Cys Val Asp Gly Ile Asn Ser Phe Thr Cys
                995                1000                1005
Leu Cys Pro Pro Gly Phe Thr Gly Ser Tyr Cys Gln His Asp Val Asn
               1010                1015                1020
Glu Cys Asp Ser Gln Pro Cys Leu His Gly Gly Thr Cys Gln Asp Gly
1025                1030                1035                1040
Cys Gly Ser Tyr Arg Cys Thr Cys Pro Gln Gly Tyr Thr Gly Pro Asn
               1045                1050                1055
Cys Gln Asn Leu Val His Trp Cys Asp Ser Ser Pro Cys Lys Asn Gly
               1060                1065                1070
Gly Lys Cys Trp Gln Thr His Thr Gln Tyr Arg Cys Glu Cys Pro Ser
               1075                1080                1085
Gly Trp Thr Gly Leu Tyr Cys Asp Val Pro Ser Val Ser Cys Glu Val
               1090                1095                1100
Ala Ala Gln Arg Gln Gly Val Asp Val Ala Arg Leu Cys Gln His Gly
1105                1110                1115                1120
Gly Leu Cys Val Asp Ala Gly Asn Thr His His Cys Arg Cys Gln Ala
               1125                1130                1135
Gly Tyr Thr Gly Ser Tyr Cys Glu Asp Leu Val Asp Glu Cys Ser Pro
               1140                1145                1150
Ser Pro Cys Gln Asn Gly Ala Thr Cys Thr Asp Tyr Leu Gly Gly Tyr
               1155                1160                1165
Ser Cys Lys Cys Val Ala Gly Tyr His Gly Val Asn Cys Ser Glu Glu
               1170                1175                1180
Ile Asp Glu Cys Leu Ser His Pro Cys Gln Asn Gly Gly Thr Cys Leu
1185                1190                1195                1200
Asp Leu Pro Asn Thr Tyr Lys Cys Ser Cys Pro Arg Gly Thr Gln Gly
               1205                1210                1215
Val His Cys Glu Ile Asn Val Asp Cys Asn Pro Pro Val Asp Pro
               1220                1225                1230
Val Ser Arg Ser Pro Lys Cys Phe Asn Asn Gly Thr Cys Val Asp Gln
               1235                1240                1245
Val Gly Gly Tyr Ser Cys Thr Cys Pro Pro Gly Phe Val Gly Glu Arg
               1250                1255                1260
Cys Glu Gly Asp Val Asn Glu Cys Leu Ser Asn Pro Cys Asp Ala Arg
1265                1270                1275                1280
Gly Thr Gln Asn Cys Val Gln Arg Val Asn Asp Phe His Cys Glu Cys
               1285                1290                1295
```

-continued

```
Arg Ala Gly His Thr Gly Arg Arg Cys Glu Ser Val Ile Asn Gly Cys
            1300                1305                1310

Lys Gly Lys Pro Cys Lys Asn Gly Gly Thr Cys Ala Val Ala Ser Asn
    1315                1320                1325

Thr Ala Arg Gly Phe Ile Cys Lys Cys Pro Ala Gly Phe Glu Gly Ala
        1330                1335                1340

Thr Cys Glu Asn Asp Ala Arg Thr Cys Gly Ser Leu Arg Cys Leu Asn
1345                1350                1355                1360

Gly Gly Thr Cys Ile Ser Gly Pro Arg Ser Pro Thr Cys Leu Cys Leu
            1365                1370                1375

Gly Pro Phe Thr Gly Pro Glu Cys Gln Phe Pro Ala Ser Ser Pro Cys
        1380                1385                1390

Leu Gly Gly Asn Pro Cys Tyr Asn Gln Gly Thr Cys Glu Pro Thr Ser
    1395                1400                1405

Glu Ser Pro Phe Tyr Arg Cys Leu Cys Pro Ala Lys Phe Asn Gly Leu
        1410                1415                1420

Leu Cys His Ile Leu Asp Tyr Ser Phe Gly Gly Gly Ala Gly Arg Asp
1425                1430                1435                1440

Ile Pro Pro Pro Leu Ile Glu Glu Ala Cys Glu Leu Pro Glu Cys Gln
            1445                1450                1455

Glu Asp Ala Gly Asn Lys Val Cys Ser Leu Gln Cys Asn Asn His Ala
        1460                1465                1470

Cys Gly Trp Asp Gly Gly Asp Cys Ser Leu Asn Phe Asn Asp Pro Trp
    1475                1480                1485

Lys Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly Phe
1505                1510                1515                1520

Asp Cys Gln Arg Ala Glu Gly Gln Cys Asn Pro Leu Tyr Asp Gln Tyr
        1525                1530                1535

Cys Lys Asp His Phe Ser Asp Gly His Cys Asp Gln Gly Cys Asn Ser
        1540                1545                1550

Ala Glu Cys Glu Trp Asp Gly Leu Asp Cys Ala Glu His Val Pro Glu
    1555                1560                1565

Arg Leu Ala Ala Gly Thr Leu Val Val Val Leu Met Pro Pro Glu
    1570                1575                1580

Gln Leu Arg Asn Ser Ser Phe His Phe Leu Arg Glu Leu Ser Arg Val
1585                1590                1595                1600

Leu His Thr Asn Val Val Phe Lys Arg Asp Ala His Gly Gln Gln Met
            1605                1610                1615

Ile Phe Pro Tyr Tyr Gly Arg Glu Glu Glu Leu Arg Lys His Pro Ile
        1620                1625                1630

Lys Arg Ala Ala Glu Gly Trp Ala Ala Pro Asp Ala Leu Leu Gly Gln
    1635                1640                1645

Val Lys Ala Ser Leu Leu Pro Gly Gly Ser Glu Gly Gly Arg Arg Arg
    1650                1655                1660

Arg Glu Leu Asp Pro Met Asp Val Arg Gly Ser Ile Val Tyr Leu Glu
1665                1670                1675                1680

Ile Asp Asn Arg Gln Cys Val Gln Ala Ser Ser Gln Cys Phe Gln Ser
        1685                1690                1695

Ala Thr Asp Val Ala Ala Phe Leu Gly Ala Leu Ala Ser Leu Gly Ser
    1700                1705                1710

Leu Asn Ile Pro Tyr Lys Ile Glu Ala Val Gln Gly Pro Gly Asp Lys
    1715                1720                1725
```

```
Thr His Thr Cys Pro Pro Cys Pro Ala Pro Glu Leu Leu Gly Gly Pro
    1730            1735            1740

Ser Val Phe Leu Phe Pro Pro Lys Pro Lys Asp Thr Leu Met Ile Ser
1745            1750            1755            1760

Arg Thr Pro Glu Val Thr Cys Val Val Val Asp Val Ser His Glu Asp
                1765            1770            1775

Pro Glu Val Lys Phe Asn Trp Tyr Val Asp Gly Val Glu Val His Asn
            1780            1785            1790

Ala Lys Thr Lys Pro Arg Glu Glu Gln Tyr Asn Ser Thr Tyr Arg Val
        1795            1800            1805

Val Ser Val Leu Thr Val Leu His Gln Asp Trp Leu Asn Gly Lys Glu
    1810            1815            1820

Tyr Lys Cys Lys Val Ser Asn Lys Ala Leu Pro Ala Pro Ile Glu Lys
1825            1830            1835            1840

Thr Ile Ser Lys Ala Lys Gly Gln Pro Arg Glu Pro Gln Val Tyr Thr
            1845            1850            1855

Leu Pro Pro Ser Arg Asp Glu Leu Thr Lys Asn Gln Val Ser Leu Thr
            1860            1865            1870

Cys Leu Val Lys Gly Phe Tyr Pro Ser Asp Ile Ala Val Glu Trp Glu
        1875            1880            1885

Ser Asn Gly Gln Pro Glu Asn Asn Tyr Lys Thr Thr Pro Pro Val Leu
    1890            1895            1900

Asp Ser Asp Gly Ser Phe Phe Leu Tyr Ser Lys Leu Thr Val Asp Lys
1905            1910            1915            1920

Ser Arg Trp Gln Gln Gly Asn Val Phe Ser Cys Ser Val Met His Glu
            1925            1930            1935

Ala Leu His Asn His Tyr Thr Gln Lys Ser Leu Ser Leu Ser Pro Gly
            1940            1945            1950

Lys
```

THERAPEUTIC METHODS FOR INHIBITING TUMOR GROWTH WITH COMBINATION OF DLL4 ANTAGONISTS AND VEGF ANTAGONISTS

CROSS-REFERENCE TO RELATED APPLICATIONS

This application is a continuation-in-part application of U.S. application Ser. No. 11/264,243 filed Oct. 31, 2005, which claims the benefit under 35 U.S.C. §119(e) of U.S. Provisional Application No. 60/623,658 filed Oct. 29, 2004, and a continuation-in-part application of U.S. application Ser. No. 11/639,894 filed Dec. 15, 2006, which claims the benefit under 35 U.S.C. §119(e) of U.S. Provisional Application Nos. 60/751,173 filed Dec. 16, 2005, 60/771,276 filed Feb. 8, 2006, 60/788,456 filed Mar. 31, 2006, and 60/830,543 filed Jul. 12, 2006, which applications are herein specifically incorporated by reference in their entirety.

BACKGROUND OF THE INVENTION

1. Field of the Invention

This invention relates to delta-like ligand 4 (Dll4), in particular, Dll4 antagonists, and therapeutic methods using the same for inhibiting Dll4-mediated blood vessel development or growth and for inhibiting tumor growth. Dll4 antagonists are especially useful for treating tumor growth in tumors that are unresponsive to other anti-tumor agents. In addition, the combination of a Dll4 antagonist and another inhibitor of angiogenesis, such as a VEGF antagonist, is particularly effective in treating cancer and tumors that are resistant to either agent alone, or other anti-tumor agents.

2. Description of Related Art

The Notch-signaling pathway is a system for cell-to-cell communication used by a wide range of eukaryotes for many biological processes, such as differentiation, proliferation, and homeostasis. Delta like 4 (Dll4) or delta-like ligand 4 (Dll4) (hereinafter "Dll4") is a member of the Delta family of Notch ligands which exhibits highly selective expression by vascular endothelium (Shutter et al. (2000) Genes Develop. 14:1313-1318). Dll4 is a ligand for Notch receptors, including Notch1 (the nucleic acid and amino acid sequences for human Notch1 are shown in SEQ ID NOS:5-6, respectively) and Notch 4 (the nucleic acid and amino acid sequences for human Notch4 are shown in SEQ ID NOS:7-8, respectively). The nucleic acid and amino acid sequences for human and mouse Dll4 are shown in SEQ ID NOS:1-2 and SEQ ID NOS:3-4, respectively. Gene targeted Dll4 mice have been generated (Duarte et al. (2004) Genes & Dev. 18: doi: 10.1101/gad. 1239004; Krebs et al. (2004) Genes & Dev. 18: doi: 10.1101/gad. 1239204: Gale et al. (2004) Proc Natl Acad Sci USA 101:15949-15954).

BRIEF SUMMARY OF THE INVENTION

This invention is based in part on the observation that the expression of Dll4 is up-regulated in tumors over-expressing vascular endothelial growth factor (VEGF), and is down-regulated with exposure to a VEGF antagonist. The experiments described below show that Dll4 antagonists are effective in inhibiting tumor growth, particularly in tumors that are not responsive to other anti-tumor therapeutics, such as a vascular endothelial growth factor (VEGF) antagonists. Furthermore, the combination of Dll4 antagonists and VEGF antagonists are synergistically effective in treating cancer or tumors that are resistant to either agent, or both when administered independently of each other, or to other anti-cancer/anti-tumor agents.

In a first aspect, the invention features Dll4 antagonists capable of binding and inhibiting Dll4. In one embodiment, the antagonist is an antibody or fragment thereof ("Dll4 Ab"), which blocks the binding of Dll4 to the Notch receptors and/or neutralizes Dll4 activities. The antibody may be polyclonal, monoclonal, chimeric, humanized, or a wholly human antibody. Preferably the antibody is a fully human monoclonal antibody or monoclonal antibody fragment. The antibody fragment may be a single chain antibody, an Fab, or an $(Fab')_2$.

In another embodiment, the Dll4 antagonist of the invention is a fusion protein comprising at least one soluble Notch receptor or fragment thereof capable of binding Dll4, fused to a multimerizing component. In specific embodiments, the soluble Notch receptor is human Notch1 or Notch 4. In another embodiment, the Dll4 antagonist of the invention is a modified Dll4 protein that is capable of binding the Notch receptor(s) but such binding does not result in activation of the receptor(s). In specific embodiments, the Dll4 antagonist of the invention is a fusion protein comprising the extracellular domain of Dll4 or a fragment thereof fused to a multimerizing component. The multimerizing component may be any component capable of forming a higher order complex through interaction with a multimerizing component on a different fusion protein. In specific embodiments wherein the multimerizing component, may be selected from the group consisting of (i) a multimerizing component comprising a cleavable region (C-region), (ii) a truncated multimerizing component, (iii) an amino acid sequence between 1 to about 500 amino acids in length, optionally comprising at least one cysteine residue, (iv) a leucine zipper, (v) a helix loop motif, (vi) a coil-coil motif, (vii) an Fc-protein, and (viii) a combination thereof. The multimerizing component is preferably an immunoglobulin domain, such as for example an Fc domain of a human IgG (e.g., SEQ ID NO:20).

The fusion protein may optionally comprise a signal sequence, which may comprise any sequence known to a skilled artisan for directing secretion of a polypeptide or protein from a cell, and include natural or synthetic sequences. Generally, a signal sequence is placed at the beginning or amino-terminus of the fusion protein of the invention.

The components of the fusion protein of the invention may be connected directly to each other or connected via one or more spacer sequences. In one preferred embodiment, the components are fused directly to each other. In another preferred embodiment, the components are connected with a nucleic acid sequence encoding a spacer of 1-200 amino acids. Any spacer known to the art may be used to connect the protein components. A spacer sequence may also include a sequence used to enhance expression of the fusion protein, provide restriction sites, and allow component domains to form optimal tertiary and quaternary structures and/or to enhance the interaction of a component with its receptor. In one embodiment, the fusion protein of the invention comprises one or more peptide sequences of 1-25 amino acids between two or more components.

The components of the fusion protein of the invention may be arranged in a variety of configurations. For example, the soluble receptor component (1), and the multimerizing component (2) may be arranged in one of the following configurations: 1-2; 2-1; 1-1-2; 1-2-1, 2-1-1.

In another embodiment, the Dll4 antagonist of the invention is an agent identified by a screening method described herein. In one embodiment, Dll4 antagonists can be identified by in vitro screening methods, such as a cell-based assay system and a cell-free assay system. In a cell-based assay system, for example, cells expressing a Dll4 protein or a fragment thereof are contacted with a test compound or a control compound, and the ability of the candidate compound to bind Dll4 or a fragment thereof, or to block Dll4/Notch signaling, is determined. In a cell-free assay system, a native or recombinant human Dll4 protein or protein fragment is contacted with a candidate compound or a control compound, and the ability of the candidate compound to bind Dll4 or a fragment thereof is determined. In another embodiment, the Dll4 antagonists can be identified by in vivo screening methods well known in the art.

In a second aspect, the invention features a method of inhibiting blood vessel growth or development, or treating a Dll4-associated condition, such as tumor or cancer, in which it is desirable to inhibit blood vessel growth or development, comprising administering an agent capable of inhibiting Dll4 activity or expression. The agent may be a Dll4 antagonist, such as a blocking antibody, a modified Dll4 molecule which binds but does not activate its Notch receptor, a fusion protein comprising the extracellular domain of Dll4 or a fragment thereof, or at least one soluble Notch receptor, e.g., Notch1 or Notch4, or fragment thereof, fused to a multimerizing component, an antisense or siRNA molecule, or an agent identified by the method of the invention. The Dll4 antagonist of the invention may be particularly useful in treating tumors which are not responsive or are less than optimally responsive to other therapeutic agents, including VEGF antagonists. The Dll4 antagonist may block production of functional blood vessels and oxygen delivery to the tumors. Thus, in one embodiment, the Dll4 antagonist of the invention is used therapeutically to treat tumors which are not responsive to treatment with a VEGF antagonist. In another embodiment, the Dll4 antagonist of the invention can be co-administered with a VEGF antagonist to a subject in need thereof to treat tumors that are resistant to either VEGF blockade alone or Dll4 blockade alone, or both when applied independently of each other.

In a third aspect, the invention features a pharmaceutical composition useful for inhibition of blood vessel growth or development, or for treatment of Dll4-associated condition, including cancer and tumors, comprising the Dll4 antagonists described above and a pharmaceutically acceptable carrier.

Other objects and advantages will become apparent from a review of the ensuing detailed description.

BRIEF SUMMARY OF THE FIGURES

FIG. 7: Human HT1080 sarcoma; FIG. 8: Human A673-Rhabdomyosarcoma; FIG. 9: Mouse Lewis Lung carcinoma; and FIG. 10: Mouse Mammary Tumor (MTT).

DETAILED DESCRIPTION

Figure 1:
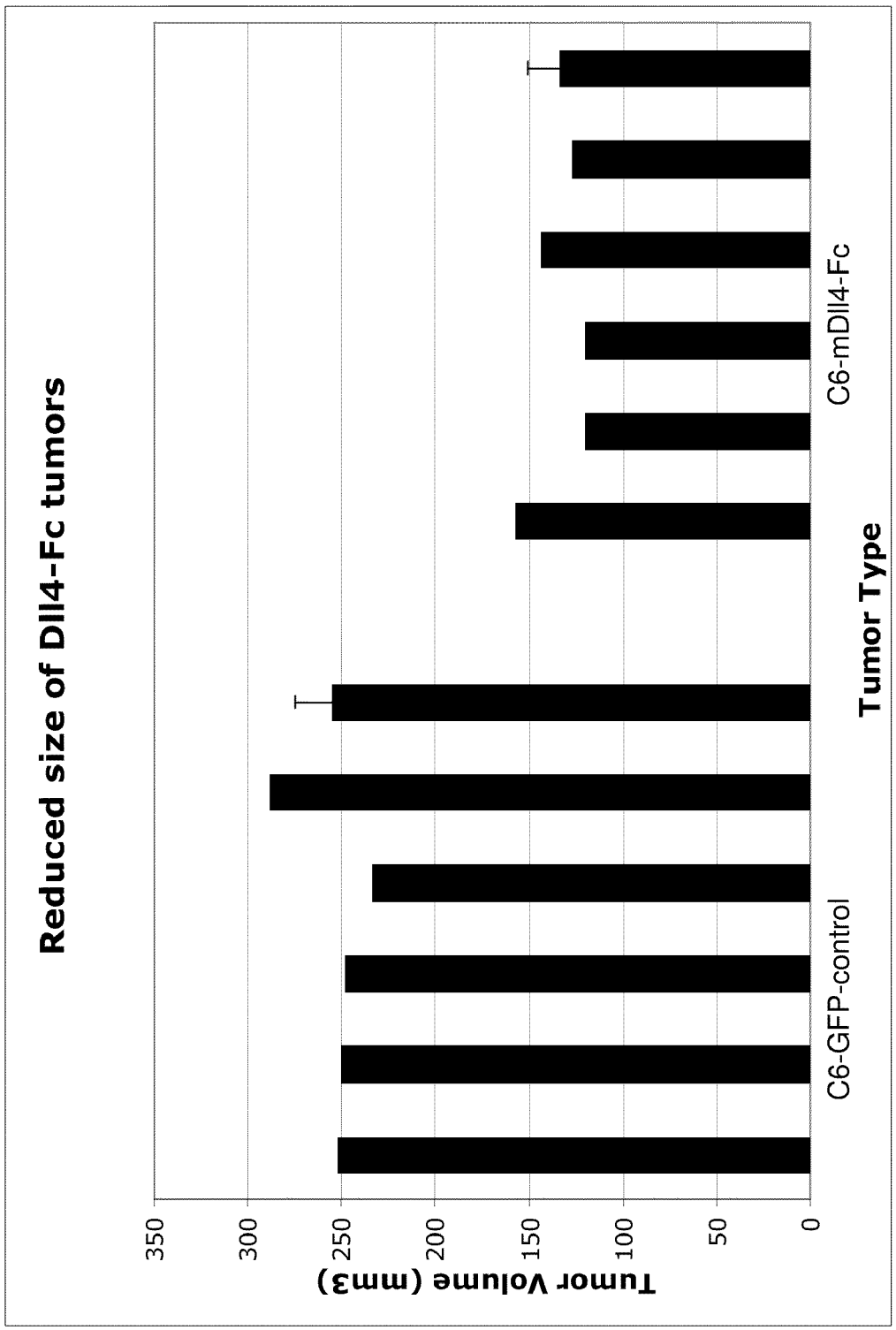
FIG. 1 shows that overexpression of mouse Dll4-Fc (mDll4-Fc) by C6 tumor cells results in smaller C6 tumors.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

DEFINITIONS

By the term "Dll4-associated" or "Dll4-mediated" condition or disease is meant a condition which is affected directly or indirectly by modulation of Dll4 activity. More specifically, Dll4 is now shown to be involved in blood vessel growth and development. Accordingly, in one embodiment, a Dll4-associated condition treatable by the method of the invention is one in which it is desirable to inhibit or reduce Dll4-mediated blood vessel growth or development or maturation, e.g., to inhibit tumor development.

By the term "inhibitor" or "antagonist" is meant a substance which retards or prevents a chemical or physiological reaction or response. Inhibition of Dll4 activity may be direct, through inhibition of receptor activation with a blocking antibody, for example, or indirect, resulting from interference with expression of the gene encoding Dll4. Common inhibitors include but are not limited to antibodies, soluble receptors, antagonists and their derivatives, and modified Dll4 ligands which bind their Notch receptor but are unable to activate signaling through such binding, and antisense molecules.

A "knock-out" animal is an animal generated from a mammalian cell which carries a genetic modification resulting from the insertion of a DNA construct targeted to a predetermined, specific chromosomal location which alters the function and/or expression of a gene that was at the site of the targeted chromosomal location. In both cases, the DNA construct may encode a reporter protein such as lacZ, protein tags, and proteins, including recombinases such as Cre and FLP. A "knock-in" animal is an animal generated from a mammalian cell which carries a genetic modification resulting from the insertion of a DNA construct targeted to a predetermined, specific chromosomal location which may or may not alter the function and/or expression of the gene at the site of the targeted chromosomal location.

A "neutralizing" or "blocking" antibody, is intended to refer to an antibody whose binding to Dll4 results in inhibition of the biological activity of Dll4. This inhibition of the biological activity of Dll4 can be assessed by measuring one or more indicators of Dll4 biological activity. These indicators of Dll4 biological activity can be assessed by one or more of several standard in vitro or in vivo assays known in the art (see examples below). Preferably, the ability of an antibody to neutralize Dll4 activity is assessed by inhibition of Dll4 binding to a Notch receptor, such as Notch1, thereby blocking Dll4/Notch signaling.

General Description

The Delta-like/Notch signaling pathway is necessary to establish an organized and hierarchical vasculature during development. Targeted deletions of various Delta-like/Notch genes, including Dll4, result in mice that die during embryonic development due to severe vascular defects. Using microarray analysis, we found that Delta-like ligand 4 (Dll4) is a VEGF-regulated gene in mouse xenograft tumor models. In addition, it was found that in these tumor models, Dll4 expression was significantly higher in tumor vessels compared to those in adjacent normal skin. To explore the effects of blocking Dll4/Notch signaling in tumors, xenograft studies were performed in mice, where a soluble Dll4-Fc molecule was delivered locally by retrovirally mediated over-expression in tumor cells or was delivered systemically using an adenoviral approach or by injecting purified protein. All methods of delivering Dll4-Fc resulted in reduced tumor growth compared to controls. Additionally, Dll4-Fc treated tumor vessels were more highly branched than controls, forming fine networks with dense vascular sprouting, but these vessels were less efficient than in those of control tumors. As revealed by array and Taqman™ analysis, these effects were associated with a decrease in Notch signaling. Similar effects on tumor growth were also observed using a polyclonal antibody solution that was injected into mice systemically. This polyclonal antibody solution was also found to inhibit binding of Dll4 to Notch1 receptor. Additionally, it was found that Dll4-Fc is more effective at reducing the growth of certain tumors than a receptor-based blocker of VEGF ("VEGF trap", U.S. Pat. No. 7,070,959). Furthermore, it was also found that the combination of Dll4 Ab and VEGF trap synergistically inhibits functional blood perfusion in tumors, which are resistant to the treatment with VEGF trap alone or Dll4 Ab alone. These findings show that Dll4 plays a key role in tumor growth, and support Dll4 as a target for the development of anti-angiogenic therapies.

Dll4 Antagonists

Dll4 antagonists include antibodies to Dll4 and fragments thereof capable of blocking the binding of Dll4 to a Notch receptor (such as Notch1), fusion proteins comprising the extracellular domain of Dll4 fused to a multimerizing component, or fragments thereof, or fusion proteins comprising at least one soluble Notch receptor component, e.g., Notch 1 or Notch 4, fused to a multimerizing component, or fragments thereof, and peptides and peptibodies (see for example, US patent publication 2003/0229023 Oliner et al., which is herein specifically incorporated by reference in its entirety).

Dll4 antibodies. The term "immunoglobulin or antibody" as used herein refers to a mammalian, including human, polypeptide comprising a framework region from an immunoglobulin gene or fragments thereof that specifically binds and recognizes an antigen, which, in the case of the present invention, is a Dll4 protein or portion thereof. If the intended antibody or antibody-like protein will be used as a mammalian therapeutic, immunoglobulin binding regions should be derived from the corresponding mammalian immunoglobulins. If the molecule is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (e.g., $IgG_1$, $IgG_2$, $IgG_3$, and $IgG_4$) as well as allotypes thereof.

An exemplary immunoglobulin (antibody) structural unit of human IgG, comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce F(ab)'$_2$, a dimer of Fab which itself is a light chain joined to $V_H$-$C_H$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms antibody, as used herein, also includes antibody fragments either produced by the modification of whole antibodies, or those synthesized de novo using recombinant DNA methodologies (e.g., single chain Fv (scFv) single variable domains (Dabs)) or those identified using display libraries such as phage, *E. coli* or yeast display libraries (see, for example, McCafferty et al. (1990) Nature 348:552-554).

Methods for preparing antibodies are known to the art. See, for example, Kohler & Milstein (1975) Nature 256:495-497; Harlow & Lane (1988) *Antibodies: a Laboratory Manual*, Cold Spring Harbor Lab., Cold Spring Harbor, N.Y.). Antibodies that are isolated from organisms other than humans, such as mice, rats, rabbits, cows, can be made more human-like through chimerization or humanization.

"Humanized" or chimeric forms of non-human (e.g., murine) antibodies are immunoglobulins, immunoglobulin chains or fragments thereof (such as Fv, Fab, Fab', F(ab')$_2$ or other antigen-binding subsequences of antibodies) that contain minimal sequences required for antigen binding derived from non-human immunoglobulin. They have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. A typical chimeric antibody is thus a hybrid protein consisting of the V or antigen-binding domain from a mouse antibody and the C or effector domain from a human antibody. Humanized antibodies have variable region framework residues substantially from a human antibody (termed an acceptor antibody) and complementarity determining regions (CDR regions) substantially from a mouse antibody, (referred to as the donor immunoglobulin). See, Queen et al., Proc. Natl. Acad Sci. USA 86:10029-10033 (1989) and WO 90/07861, U.S. Pat. Nos. 5,693,762, 5,693,761, 5,585,089, 5,530,101 and 5,225,539. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly; (2) is adjacent to a CDR region; (3) otherwise interacts with a CDR region (e.g., is within about 6 Å of a CDR region), or (4) participates in the $V_L$-$V_H$ interface. Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Methods for generating human antibodies include, for example, VelocImmune™ (Regeneron Pharmaceuticals), XenoMouse™ technology (Abgenix), the "minilocus" approach, and phage display. The VelocImmune™ technology (U.S. Pat. No. 6,596,541) encompasses a method of generating a high specificity fully human antibody to a select antigen. This technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody. In specific embodiment, the cell is a CHO cell.

The XenoMouse™ technology (Green et al. (1994) Nature Genetics 7:13-21) generates a mouse having both human variable and constant regions from both the heavy chain and kappa light chain loci. In an alternative approach, others have utilized a 'minilocus" approach in which an exogenous Ig locus is mimicked through inclusion of individual genes from the Ig locus (see, for example, U.S. Pat. No. 5,545,807). The DNA encoding the variable regions can be isolated with or without being operably linked to the DNA encoding the human heavy and light chain constant region.

Alternatively, phage display or related display technologies can be used to identify antibodies, antibody fragments, such as variable domains, and heteromeric Fab fragments that specifically bind to Dll4. (see for example US patent publication 2003/0229023).

Screening and selection of preferred immunoglobulins (antibodies) can be conducted by a variety of methods known to the art. Initial screening for the presence of monoclonal antibodies specific to Dll4 may be conducted through the use of ELISA-based methods or phage display, for example. A secondary screen is preferably conducted to identify and select a desired monoclonal antibody. Secondary screening may be conducted with any suitable method known to the art. One preferred method, termed "Biosensor Modification-Assisted Profiling" ("BiaMAP") is described in U.S. patent application publication 2004/101920, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody:antigen interactions. Alternatively, ELISA-based, bead-based, or Biacore®-based competition assays can be used to identify binding pairs that bind different epitopes of Dll4 and thus are likely to cooperate to bind the ligand with high affinity.

Fusion proteins. When the Dll4 antagonist is a fusion protein, the multimerizing component may be selected from the group consisting of (i) an immunoglobulin domain, (ii) a truncated multimerizing component, (iii) an amino acid sequence between 1 to about 500 amino acids in length, optionally comprising at least one cysteine residue, (iv) a leucine zipper, (v) a helix loop motif and (vi) a coil-coil motif. In a preferred embodiment, the multimerizing component is an immunoglobulin domain, preferably an Fc domain, e.g., a human Fc (SEQ ID NO:20). The fusion protein may optionally comprise a signal sequence, which may comprise any sequence known to a skilled artisan for directing secretion of a polypeptide or protein from a cell, include natural or synthetic sequences. Generally, a signal sequence is placed at the beginning or amino-terminus of the fusion protein of the invention. Such a signal sequence may be native to the cell, recombinant, or synthetic. The components of the fusion protein of the invention may be connected directly to each other or connected via one or more spacer sequences. In one preferred embodiment, the components are fused directly to each other. In another preferred embodiment, the components are connected with a nucleic acid sequence encoding a spacer of 1-200 amino acids. Any spacer known to the art may be used to connect the protein components. A spacer sequence may also include a sequence used to enhance expression of the fusion protein, provide restriction sites, and allow component domains to form optimal tertiary and quaternary structures and/or to enhance the interaction of a component with its receptor. In one embodiment, the fusion protein of the invention comprises one or more peptide sequences of 1-25 amino acids between two or more components.

In one embodiment, the fusion protein may comprise the extracellular domain of Dll4. The extracellular domain of Dll4 is composed of a Delta/Serrate/Lag-2 (DSL) domain and a tandem of eight epidermal growth factor (EGF)-like repeats. Generally, the EGF domains are recognized as occurring at about position 218-251 (domain 1), 252-282 (domain 2), 284-322 (domain 3), 324-360 (domain 4), and 362-400 (domain 5), with the DSL domain at about position 173-217 and the N-terminal domain at about position 27-172 of hDll4 (SEQ ID NO:2). In specific embodiments, the hDll4 antagonist capable of inhibiting Dll4 activity is the extracellular domain of Dll4 (amino acid residues 1-529 of SEQ ID NO:2, with or without a signal peptide) fused to a human Fc, DSL-hFc (SEQ ID NO:21) comprising about amino acid 173 to about 217 of SEQ ID NO:2 fused to hFc (SEQ ID NO:20), N-terminal domain-DSL-hFc (SEQ ID NO:22) comprising about 27-217 of SEQ ID NO:2 fused to hFc, EGF domains 1-5-hFc (SEQ ID NO:23) comprising about 218-400 fused to hFc, EGF domains 1-4-hFc (SEQ ID NO:24) comprising about 218-360 fused to hFc, EGF domains 1-3-hFc (SEQ ID NO:25) comprising about 218-322 fused to hFc, EGF domains 1-2-hFc (SEQ ID NO:26) comprising about 218-282 fused to hFc, or variants thereof optionally comprising linkers between the domain components. The components of the fusion protein may also be arranged in a variety of configurations while retaining the ability to act as Dll4 antagonists.

In another embodiment, the fusion protein may comprise at least one soluble Notch receptor. The soluble extracellular domain of a Notch receptor is composed of multiple EGF-like domains. Accordingly, the instant invention envisions using the full length extracellular domain as well as fragments of the extracellular domain which retain the capacity to bind Dll4. In a specific embodiment, the soluble Notch receptor is from Notch1. The nucleotide (cDNA) sequence and the amino acid sequence of human Notch1 are shown as SEQ ID NO:5 and SEQ ID NO:6, respectively. In a more specific embodiment, the fusion protein comprises the extracellular ligand-binding portion of Notch1 fused to an oligomerizing domain, such as the Fc domain of human IgG. The nucleotide (cDNA) and amino acid sequences of mouse Notch1-Fc are shown as SEQ ID NOS:27 and 28, respectively. In a preferred embodiment, the fusion protein is a human Notch1-Fc comprising the nucleotide and amino acid sequences of SEQ ID NOS:29 and 30, respectively.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Pharmaceutical Compositions

The present invention also provides pharmaceutical compositions. Such compositions comprise a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention which will be effective in the treatment of a Dll4-mediated condition can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 0.5 to 20 milligrams of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Combination Therapies

In numerous embodiments, the Dll4 antagonists of the present invention may be administered in combination with one or more additional compounds or therapies. For example, multiple fusion proteins or anti-Dll4 antibodies can be co-administered, or be administered in conjunction with one or more therapeutic compounds. Co-administration and combination therapy are not limited to simultaneous administration, separately or together, but also include sequential administrations. The combination therapies may be especially effective for treating cancer or tumors that are resistant to particular types of therapeutic compounds. For example, a Dll4 antagonist may be administered in combination with another inhibitor of blood vessel growth or development, such as VEGF antagonist, for treating cancer or tumors that are resistant to either Dll4 antagonists or VEGF antagonists, or both when administered independently. Although little is known about the effects of blocking the both pathways on the functional perfusion of tumors, the experiments described below have indicated that such combination therapies indeed have synergistic effects on the inhibition of functional perfusion of tumors. Thus, in a preferred embodiment, the Dll4 inhibitor of the invention is administered with a VEGF antagonist, such as an anti-VEGF antibody or a VEGF trap. Preferred embodiments of a VEGF trap is VEGFR1R2-Fc$\Delta$C1(a) (SEQ ID NO:19) (as described in WO 00/75319, which publication is herein specifically incorporated by reference in its entirety).

Combination therapy includes administration of a single pharmaceutical dosage formulation which contains a Dll4 antagonist of the invention and one or more VEGF antagonist(s), or other therapeutic agents; as well as administration of a Dll4 antagonist and one or more additional agent(s) in its own separate pharmaceutical dosage formulation. For example, a Dll4 antagonist and a VEGF antagonist, a cytotoxic agent, a chemotherapeutic agent, or a growth inhibitory agent can be administered to the patient together in a single dosage composition such as a combined formulation, or each agent can be administered in a separate dosage formulation. Where separate dosage formulations are used, Dll4 antagonist of the invention and one or more additional agents can be administered concurrently, or separately at staggered times, i.e., sequentially.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate;

defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Targeting the Dll4 Gene in Mice.

Gene Targeting. Velocigene™ technology (Valenzuela et al. (2003) Nat. Biotechnol. 21:652-9) was used to generate a precise deletion and exchange of the Dll4 coding region, extending from the initiation to the termination codon (corresponding an 8.1 kB region comprising all of the coding exons and intervening introns), with the b-galactosidase reporter gene as well as a neomycin selection cassette. Briefly, a bacterial artificial chromosome (BAC) containing the 8.1 kb Dll4 coding region and 140 Kb of flanking sequences (clone 475d4 from a 129/SvJ BAC library obtained from Incyte Genomics) was modified to generate a BAC-based targeting vector which was then linearized and used as a targeting vector to replace the Dll4 gene in F1H4 (C57BL/6:129 hybrid) mouse embryonic stem (ES) cells. Correctly targeted embryonic stem cells were identified using the loss of native allele (LONA) assay (Valenzuela et al. (2003) supra). Two independent correctly targeted ES lines were used to generate chimeric male mice that were complete transmitters of ES-derived sperm. Chimeras were then bred to C57BL/6 and/or ICR females to generate F1 mice or embryos, which were genotyped by LONA assays and β-galactosidase histochemical assays. Mice derived from both ES lines behaved identically, and pooled data from both clones were used for statistics.

Results. Targeting the Dll4 gene in mice resulted in embryonic lethality and severe vascular defects, even in mice targeted at a single allele (see Gale et al. (2004) Proc Natl Acad Sci USA 101:15949-15954).

Tumor implantations. Lewis lung carcinoma cells (ATCC) were subcutaneously implanted into the flank of Dll4 chimeric mice, harvested after 16 days, cut into 80 micron sections, and stained for CD31/PECAM or β-galactosidase as described (Holash et al. (2002) Proc Natl. Acad. Sci. USA 99:11393-8).

PECAM and reporter staining. Staining of whole-mounted embryos, as well as tissue sections from embryos and adults, were performed as previously described for CD31/PECAM to define the vascular endothelium and for β-galactosidase to visualize the Dll4 reporter gene product (Gale et al. (2004) PNAS 101:15949-54).

Example 2

Dll4-Fc Construct and Mouse Xenograph Studies.

Dll4-Fc (−TM) construct. Mouse Dll4-Fc (mDll4-Fc) was constructed with 2297 nucleotides corresponding to the extracellular domain of mouse Dll4 (SEQ ID NO:18), without the transmembrane region (−TM), and a human Fc domain. The encoded amino acid sequence had 765 amino acids and a molecular weight of approximately 85 kDa. Likewise, human Dll4-Fc (hDll4-Fc) construct was also prepared in which the extracellular domain (residues 1-529 of SEQ ID NO:2) of human Dll4 was fused with a human Fc domain.

FIG. 1 shows that mDll4-Fc over-expression by C6 tumor cells resulted in smaller C6 tumors (mean±SD).

Retroviral engineering of tumor cells to over-express Dll4-Fc. C6 rat glioma tumor cells (ATCC) were infected with retrovirus to over-express green fluorescent protein (GFP) and soluble mDll4-Fc; cells infected with GFP alone were used as controls. Cells were FACS sorted for GFP fluorescence twice.

Retrovirus delivered mDll4-Fc. $10^6$ cells/mouse were implanted subcutaneously into the shaved right flank of male SCID/CB17 mice (8-10 wk old) with either GFP or mDll4-Fc retrovirally engineered C6 cells.

Tumor volume measurements: After tumors became palpable, size measurements were recorded every three days using a caliper (size=(length×width$^2$)/2). Once animals were sacrificed, ex vivo measurements were obtained with calipers and volume was calculated using the formula length×width× height).

Tumor Histology. Twelve to sixteen days after tumor cell implantation, tumors were harvested and processed for histological or expression analysis. Tumors were cut into 80 μm sections, stained with antibodies to CD31/Pecam-1 followed by DAB-peroxidase reaction, and counterstained with pyroninY. Vessel morphometric analysis was performed using the NIH Image 1.62 analysis program.

Northern Blotting and Real Time-PCR. Total RNA was prepared from tumor tissue using Trizol reagent (Life Technologies, Grand Island, N.Y.). RNA (10 mg) was separated on 1.2% agarose gels, transferred to nylon membrane and immobilized by UV crosslinking. After prehybridization, 32P-labeled Dll4 or glyceraldehyde-3-phosphate dehydrogenase (GAPDH)-specific probes were added, and the filters were hybridized at 42° C. overnight. Stringent washes were performed by standard protocols (one wash 0.5×SSPE buffer followed by two washes with 0.2×SSPE buffer performed at 55° C. for 30 minutes each). An autoradiograph was obtained after 48 h exposure to x-ray film with intensifying screens. In addition, tissue specific expression was analyzed in separate reactions using the Taqman® (Applied Biosystems, Foster City, Calif.) real-time PCR chemistry and detection system with the primers pairs and labeled probes specific for Dll4, the notch receptors 1 and 4 and notch downstream targets, Hes1, Hey2, HeyL and Nrarp. The number of cycles necessary to reach the threshold for amplification of the cDNA (or CT values) was obtained, and normalized to a housekeeping reference (GAPDH) (=2-DCT). The results were normalized to a baseline, the vehicle control for the experiment, giving the relative mRNA abundance change (=2DDCT) and is expressed as the mean±S.E.M. for at least 4 separate samples run in triplicate (Livak and Schmittgen (2001) Methods. December; 25(4):402-8).

Quantitative RT-PCR analysis for Dll4 HeyL, Nrarp and Hes1. The RT-PCR analysis was performed as described (Livak et al. (2001) Methods 24:402-8). Results are expressed as the ratio of the amount of the RNA of interest to the amount of control RNA (GAPDH) as described (Daly et al. (2004) Genes Dev. 18:1060-71) on an Applied Biosystems 7900HT using specific primers and probes as follows: Dll4 Primers: Dll4-1574F (SEQ ID NO:9) and Dll4-1644R (SEQ ID NO:10) and Dll4 Probe: Dll4-1594T (SEQ ID NO:11); HeyL Primers: mHeyL-135F (SEQ ID NO:12) and mHeyL-216R (SEQ ID NO:13) and HeyL Probe: mHeyL-154T (SEQ ID NO:14); Nrarp Primers: mNrarp-350F (SEQ ID NO: 15) and mNrarp-418R (SEQ ID NO:16) and Nrarp probe: mNrarp-373T: (SEQ ID NO:17) and mHesI (ID Mm00468601 m1, Hes1) (ABI, Assay on demand services). cDNAs were derived from C6-Dll4-Fc and C6-Dll4 tumors In vitro assay to determine if secreted mDll4-Fc expressed in C6 cells can activate Notch signaling in HUVEC. $4 \times 10^5$ HUVEC cells were plated onto 60 mm dish to obtain ~50% confluent cultures the following day. The next day, $8 \times 10^5$ C6 cells were plated on top of HUVECs. After 24 hrs of co-culture, cells were scrapped into 1 ml of Tri Reagent and total RNA was prepared as previously described. Samples were analyzed by Taqman® using human specific Hes1, HeyL and Nrarp probes.

Example 3

Effect of Systemic Administration of Dll4-Fc.

Dll4-Fc protein. Plasmid encoding hDll4-Fc cDNA construct described above was transfected into CHO cells, and secreted protein was purified from the supernatant. hDll4-Fc protein was purified and used to treat tumor bearing mice via subcutaneous injection (10 mg/kg, 3× per week).

Figure 2:
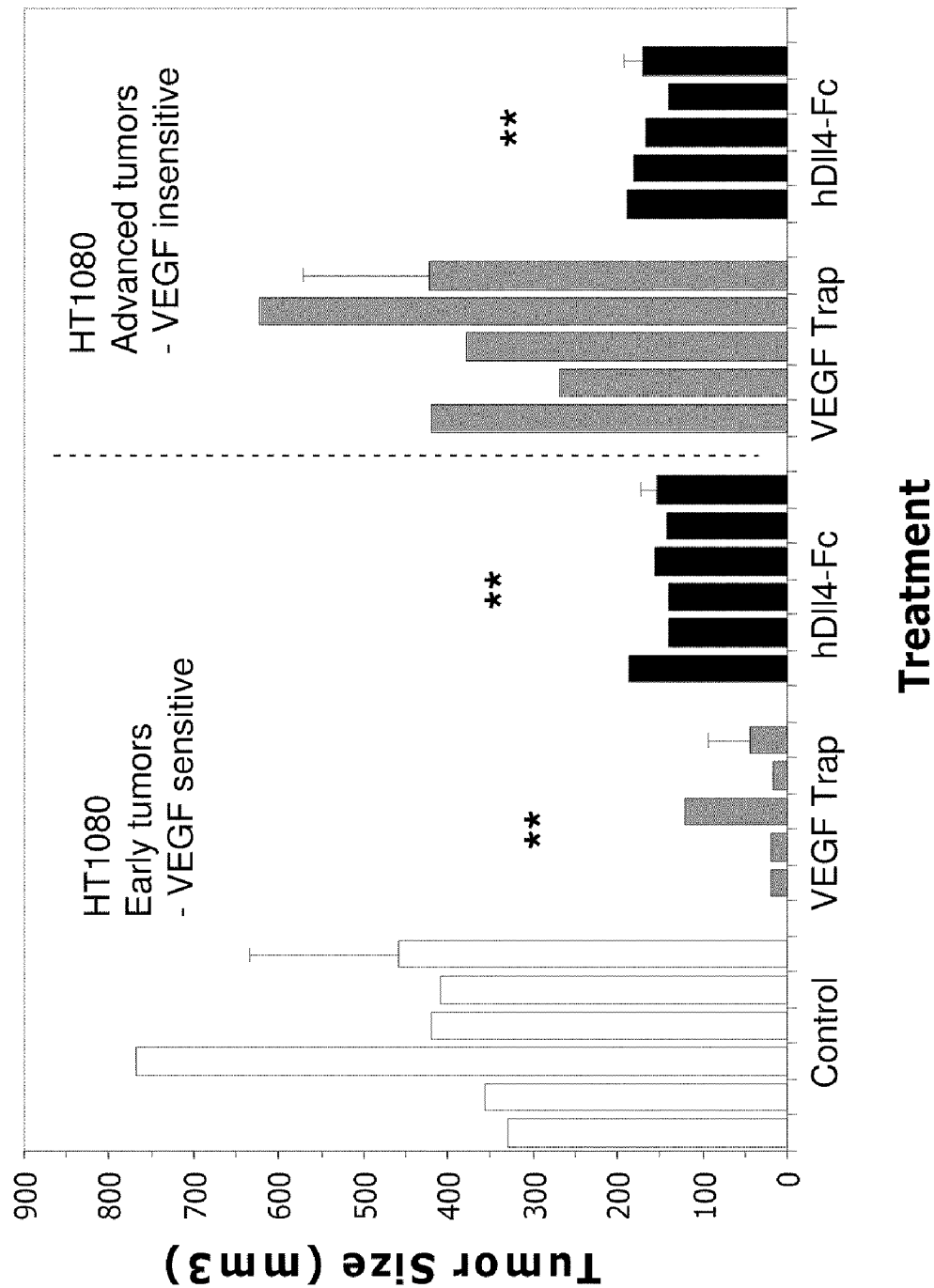
FIG. 2 shows that systemically-delivered human Dll4-Fc (hDll4-Fc) is highly effective in reducing HT1080 tumors relative to a receptor-based VEGF antagonist. Left panel: hDll4-Fc or VEGF Trap protein given at time of tumor implant, tumors harvested day 25; Right panel: hDll4-Fc or VEGF Trap protein given day 15 after implant, tumors harvested day 25.

Results. Experiments were conducted in which HT1080 tumors were implanted into mice as described above at day 0. Starting on either day 0 or day 15 (at 100 mm³ in size), mice were treated with purified hDll4-Fc protein (10 mg/kg, 3× per week) or control protein. Other groups were treated with VEGF antagonist (VEGF Trap, SEQ ID NO:19) at a dose of 25 mg/kg, three times per week. The results are shown in FIG. 2. In tumors treated from day 0 (left panel), both VEGF antagonist and hDll4-Fc were effective at controlling tumor growth. In tumors treated from 100 mm³ in size (right panel), hDll4-Fc was again effective at controlling tumor growth, and was in fact more effective than VEGF antagonist.

Quantification of circulating hDll4-Fc and hFc. Serum samples obtained from GFP or hDll4-Fc treated mice bearing tumors were analyzed by ELISA assay. ELISA was performed by coating plates with hFc as the capture antibody, blocked with 0.2% I-Block solution (Tropix) and using hFc conjugated to peroxidase as a report antibody. Purified hFc and hDll4-Fc proteins were included as standard curves.

VEGF-Inhibitor treatment. VEGF trap (R1R2) (Regeneron Pharmaceuticals) (SEQ ID NO:19) or placebo (5% vol/vol PBS/glycerol) was administered subcutaneously to mice bearing 100 mm³ tumors at a dose of 25 mg/kg every three days until the end of the study.

Adenovirus delivery of mDll4-Fc. Other experiments not shown have used adenovirus to deliver mDll4-Fc systemically. C6, HT1080, or MMT tumor cells were implanted subcutaneously into the shaved right flank of male SCID/CB17 mice (8-10 wk old). After 24 hours, $1 \times 10^9$ pfu of adeno-hFc or adeno-mDll4-Fc was injected into the jugular vein of the mice. Similar results on tumor growth were seen with adeno-mDll4-Fc as with systemic treatment with hDll4-Fc protein.

Example 4

Effect of Polyclonal Antibodies to Dll4-Fc on HT1080 Tumors.

Figure 3:
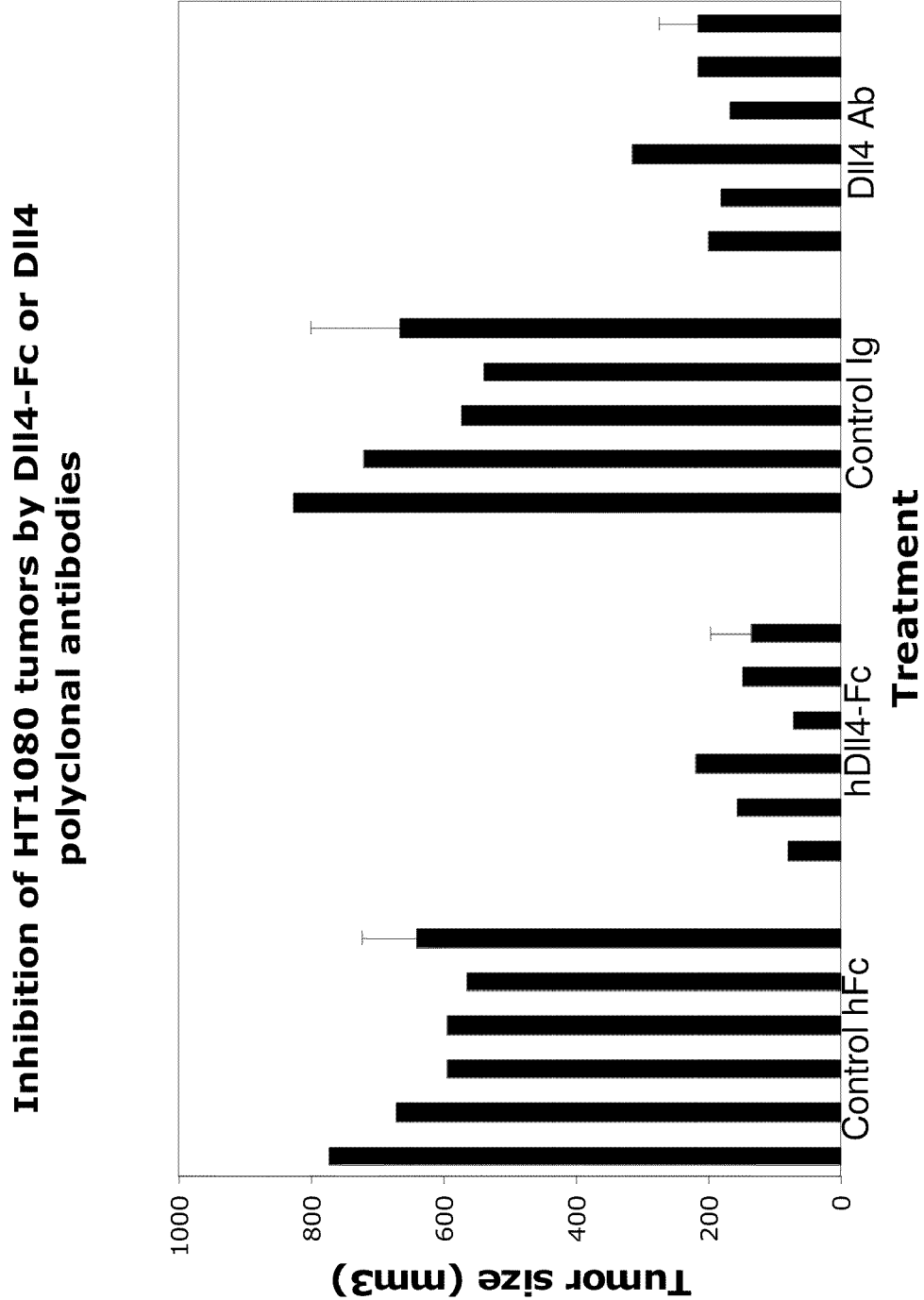
FIG. 3 shows that purified hDll4-Fc protein or polyclonal Dll4 antibodies inhibits HT1080 tumor growth.

Experiments were conducted in which HT1080 tumors were implanted into mice on day 0 as described above. When the tumors reached 100 mm³ (approximately at day 15), mice were treated three times per week with hDll4-Fc alone (25 mg/kg), control antibody (rabbit Ig), or rabbit anti-Dll4 polyclonal antibodies raised against the extracellular domain of human Dll4 and depleted for binding to human Fc (10 mg/kg). Results show tumor size in each treatment group±S.D. (FIG. 3). Dll4 antibodies were highly effective against HT1080 tumor growth and had effectiveness similar to that seen with hDll4-Fc. These results show that a specific blocker of Dll4 is a potent anti-tumor agent.

Figure 4:
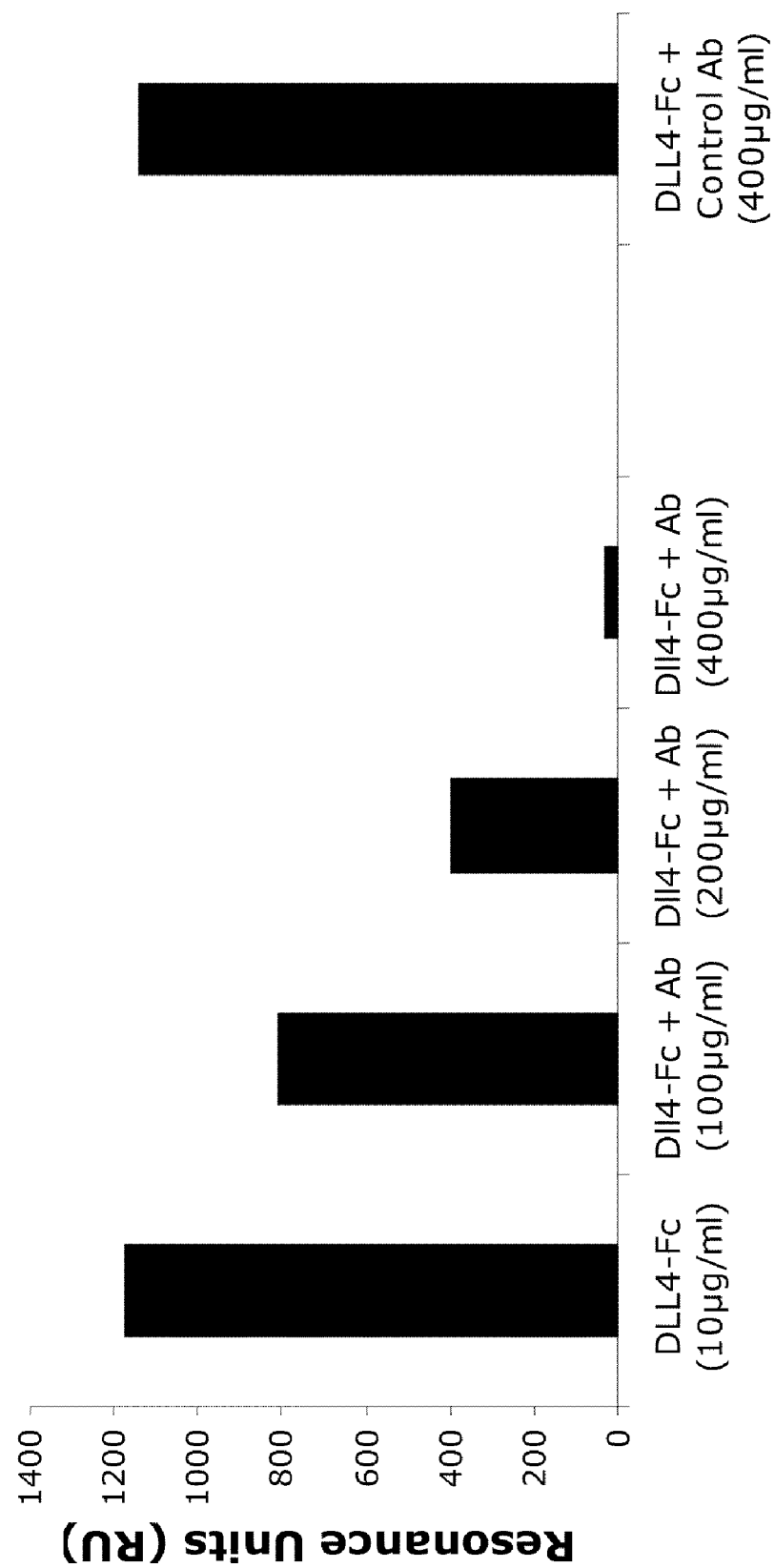
FIG. 4 shows inhibition of hDll4-Fc binding to the Notch1 receptor by the increasing amount of polyclonal antibodies to Dll4, in a surface plasmon resonance (BiaCore®) assay.

Surface plasmon resonance (BiaCore®) assays were performed confirming the Dll4 antibodies were capable of blocking Dll4 binding to Notch receptor. Notch 1 was coated on the chip surface and hDll4-Fc was incubated with increasing amounts of rabbit polyclonal anti-Dll4 antibody (described above). The results in FIG. 4 show that increasing amount of Dll4 antibody increasingly blocked hDll4-Fc binding to Notch1 (control=hDll4-Fc+non-specific rabbit polyclonal antibody).

Example 5

Effects of Dll4 Ab and VEGF Trap on HT1080 Tumor Perfusion

Figure 5:
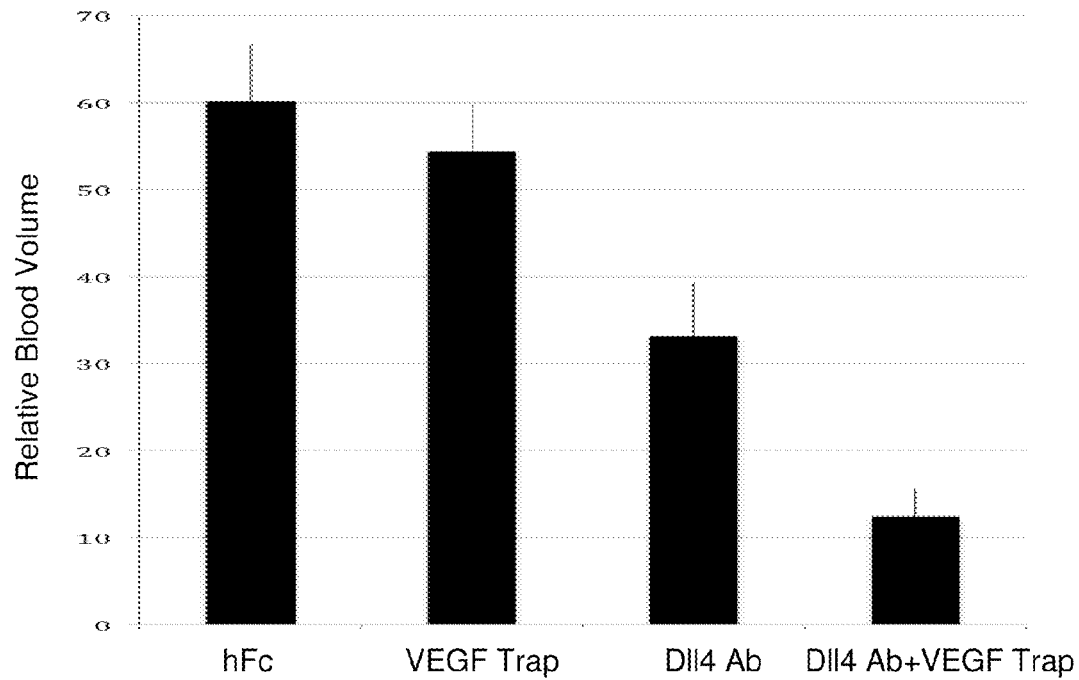
FIG. 5 shows relative blood volumes, measured by micro-ultrasound imaging using a vascular contrast-enhancing agent, of VEGF-Trap-resistant HT1080 human fibrosarcomas that were implanted in SCID mice and treated with hFc, VEGF-Trap, anti-Dll4 antibody ("Dll4 Ab"), or combination of VEGF-Trap and Dll4 Ab. The error bars indicate the standard errors of the mean (SEM).

HT1080 human fibrosarcoma is very resistant to VEGF Trap, showing no change in tumor growth and only a minimal reduction in vessel density. However, Dll4 blockade causes the reduction of HT1080 tumor growth despite an apparent increase in the density of tumor vascular structures. The effects of Dll4-Notch inhibitor and VEGF inhibitor, each alone or in combination, on the functional perfusion of HT1080 tumor cells were studied in this experiment. Immunodeficient male CB17 SCID mice were implanted with $2\times10^6$ HT1080 tumor cells subcutaneously into the right flank. When the tumors reached a size of approximately 100 mm$^3$, the mice were subcutaneously treated with hFc control protein (25 mg/kg), VEGF Trap (25 mg/kg), Dll4 Ab (10 mg/kg), or a combination of VEGF Trap and Dll4 Ab. The Dll4 Ab was prepared in-house, based on the published sequence (WO 2007/143689), and designated as REGN 577. REGN 577 binds to human and mouse Dll4, but does not detectably binds human Dll1 and JAG1. Twenty-four hours after the treatment, each mouse was anesthetized with isoflurane and injected intravenously via tail vein with 50 μl vascular contrast agent (MicroMarker Contrast™ Agent, VisualSonics, Canada). Tumor perfusion was assessed by micro-ultrasound acquisition of 2-dimensional image series that include images prior to contrast agent injection, during injection and after injection. The image series allow the calculation of the relative contrast intensity by subtracting the reference frames (prior to contrast agent injection) from the frames that contain contrast agent within the selected tumor tissue area. The relative blood volume for each animal was calculated as the plateau value in the average contrast intensity vs time curve. The relative blood volumes (i.e., tumor perfusion) of the different mice in each treatment group were then averaged and displayed in a bar graph (error bars: SEM). The results are shown in Table 1 and FIG. 5.

TABLE 1

| TREATMENT | NUMBER OF ANIMALS | AVERAGE OF RELATIVE CONTRAST INTENSITY | SEM |
|---|---|---|---|
| hFc | 11 | 60 | 7 |
| VEGF Trap | 9 | 54 | 5 |
| Dll4 Ab (REGN577) | 9 | 33 | 6 |
| Dll4 Ab (REGN577) + VEGF Trap | 5 | 12 | 3 |

Dll4 inhibition produced a ~45% decrease in HT1080 tumor perfusion (relative contrast intensity decreased from 60 in hFc group to 33 in the Dll4 group), whereas VEGF Trap produced only a ~10% decrease (relative contrast intensity 54), effects that were mirrored in the relative effects on tumor growth. Interestingly, the combination of Dll4 and VEGF inhibitors resulted in a dramatic decrease in HT1080 tumor perfusion (~80% compared to Fc-treated HT1080 tumors; relative contrast intensity 12) as well as potent inhibition of growth.

Example 6

Effects of Dll4 Ab and VEGF Trap on C6 Tumor Perfusion

Figure 6:
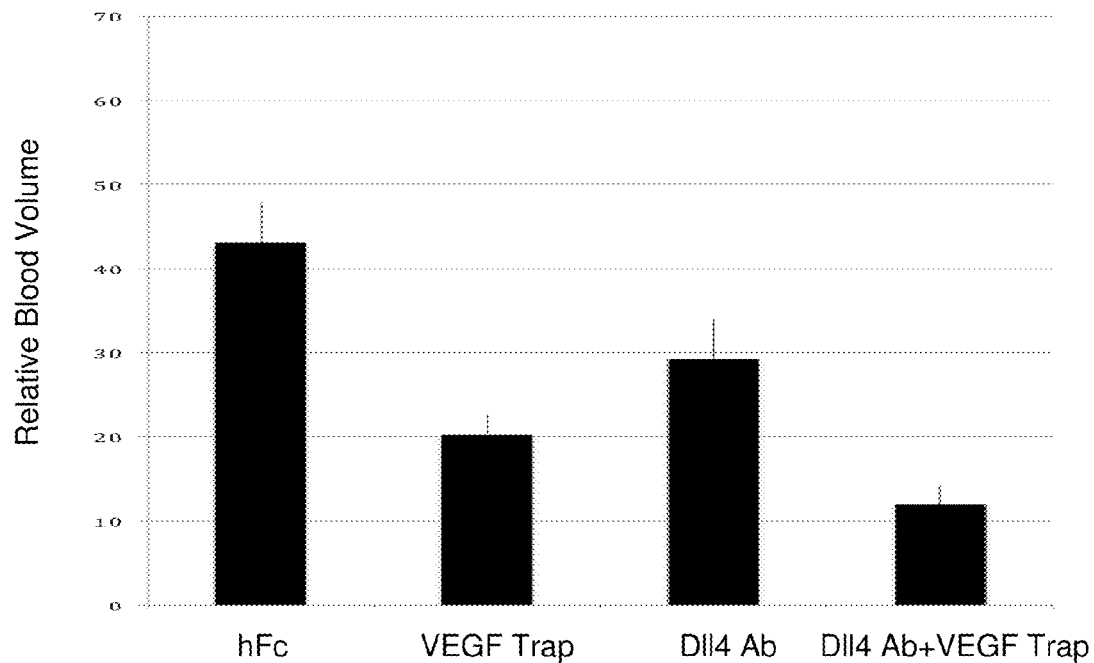
FIG. 6 shows relative blood volumes, measured by micro-ultrasound imaging using a vascular contrast-enhancing agent, of Dll4-blockade-resistant C6 rat glioblastoma tumors that were implanted in SCID mice and treated with hFc, VEGF-Trap, Dll4 Ab, or combination of VEGF-Trap and Dll4 Ab. The error bars indicate SEM.

C6 rat glioblastoma tumors are sensitive to VEGF Trap, showing a delay in tumor growth and a dramatic decrease in vessel density. In contrast, Dll4 blockade does not affect C6 tumor growth as dramatically as VEGF Trap. The effects of Dll4-Notch inhibitor and VEGF inhibitor, each alone or in combination, on the functional perfusion of C6 tumors were studied in this experiment. Immunodeficient male CB17 SCID mice were implanted with $1\times10^6$ C6 tumor cells subcutaneously into the right flank. When the tumors reached a size of approximately 100 mm$^3$ the mice were subcutaneously treated with hFc control protein (25 mg/kg), VEGF Trap (25 mg/kg), REGN 577 Dll4 Ab (10 mg/kg), or a combination of VEGF Trap and Dll4 Ab. Twenty-four hours after the treatment, each mouse was anesthetized with isoflurane and injected intravenously via tail vein with 50 μl vascular contrast agent (MicroMarker Contrast™ Agent, VisualSonics, Canada). Tumor perfusion was assessed by micro-ultrasound acquisition using vascular contrast enhancing agent as described above and the relative blood volume for each animal was calculated. The results are shown in Table 2 and FIG. 6 (error bars: SEM).

TABLE 2

| TREATMENT | NUMBER OF ANIMALS | AVERAGE OF RELATIVE CONTRAST INTENSITY | SEM |
|---|---|---|---|
| hFc | 11 | 43 | 5 |
| VEGF Trap | 11 | 20 | 2 |
| Dll4 Ab (REGN577) | 5 | 29 | 5 |
| Dll4 Ab (REGN577) + VEGF Trap | 6 | 12 | 2 |

VEGF inhibition produced a ~53% decrease in C6 tumor perfusion (relative contrast intensity decreased from 43 in hFc Group to 20 in the VEGF Trap treated group), whereas Dll4 blockade produced a decrease of ~32% (relative contrast intensity 29), effects that were mirrored in the relative effects on tumor growth. The combination of Dll4 and VEGF inhibitors resulted in a dramatic decrease in C6 tumor perfusion (~72% compared to Fc-treated C6 tumors; relative contrast intensity 12).

Example 7

Effects of hDll4-Fc and VEGF Trap on HT1080 Tumor Growth

Figure 7:
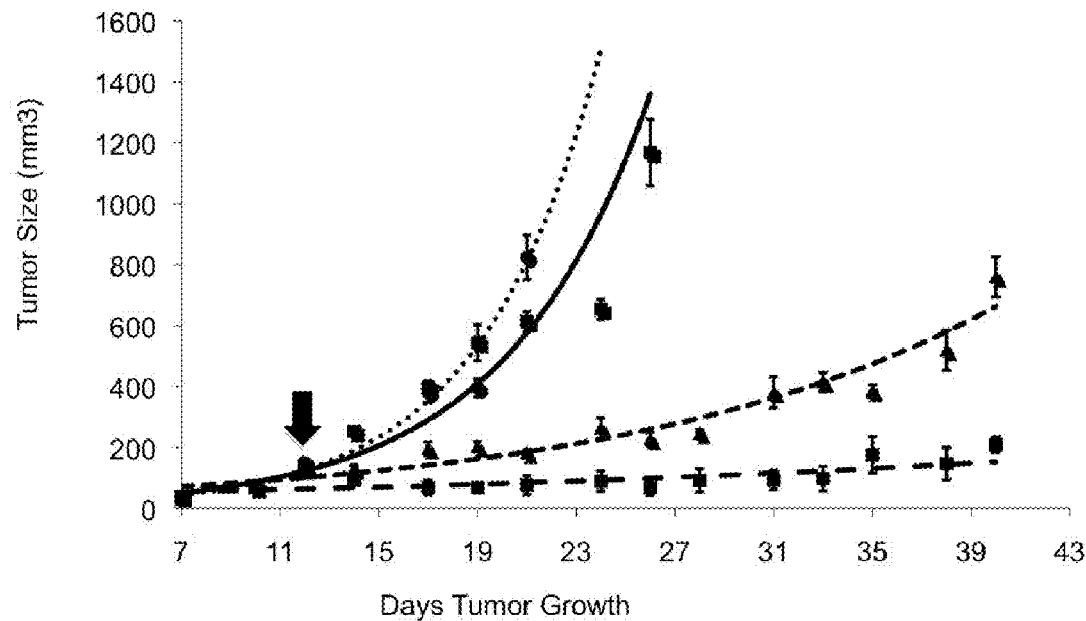
FIGS. 7-10 show that the combination of VEGF-Trap and hDll4-Fc greatly inhibits various types of tumor growth compared to the treatment by either agent alone. Symbols: hFc—; VEGF-Trap . . . ; hDll4-Fc - - - ; VEGF-Trap+hDll4-Fc— — —. The error bars indicate SEM. The tested tumors are.

The effects of Dll4-Notch inhibitor and VEGF inhibitor, each alone or in combination, on the growth of HT1080 tumor cells were studied in this experiment. Immunodeficient male CB17 SCID mice were each implanted with $2.5\times10^6$ HT1080 tumor cells subcutaneously into the right flank. When the tumors reached a size of approximately 150 mm$^3$, the mice were subcutaneously treated with hFc control protein (25 mg/kg), VEGF Trap (25 mg/kg), hDll4-Fc (25 mg/kg), or a combination of VEGF Trap and hDll4-Fc, three times per week beginning on day 12. FIG. 7 shows the tumor size in each treatment group±SEM. The combination of VEGF Trap and hDll4-Fc were highly effective against HT1080 tumor growth compared to the treatment with each agent alone.

Example 8

Effects of hDll4-Fc and VEGF Trap on the Growth of Various Types of Tumor

Figure 8:
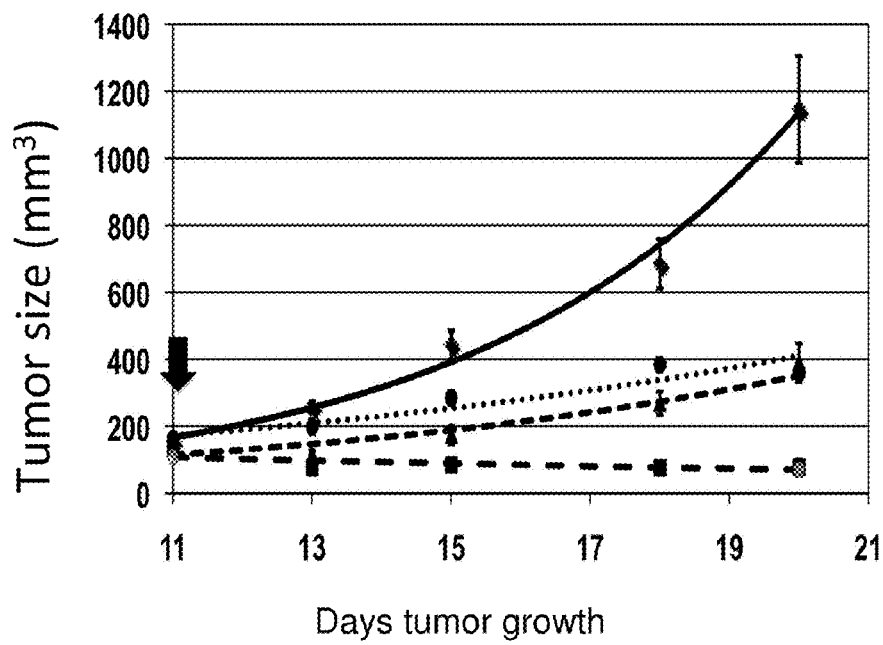
Figure 9:
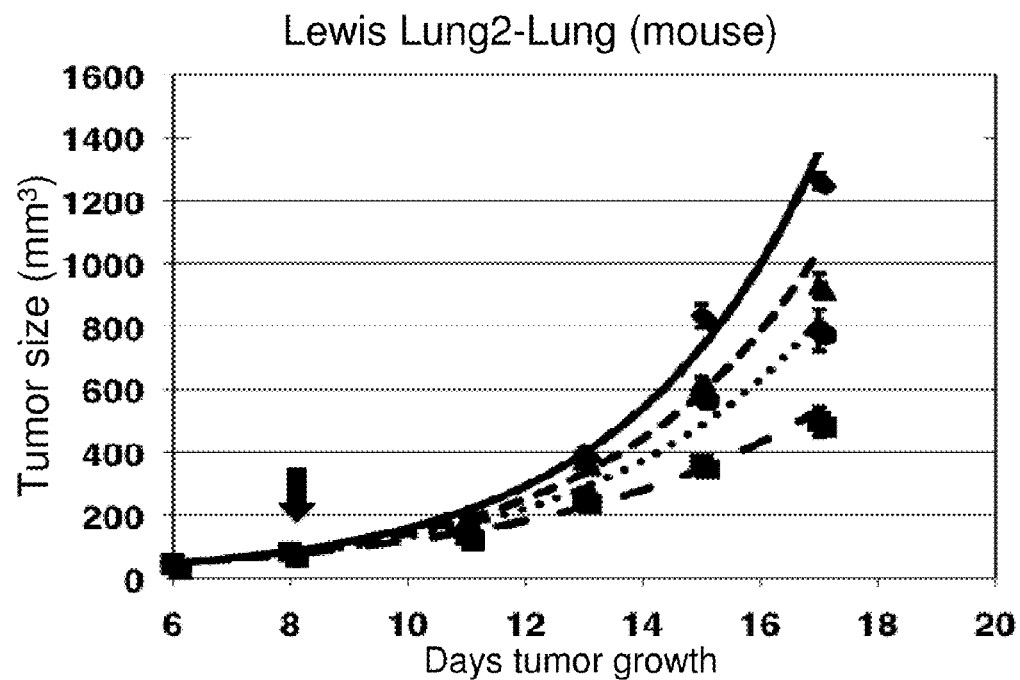
Figure 10:
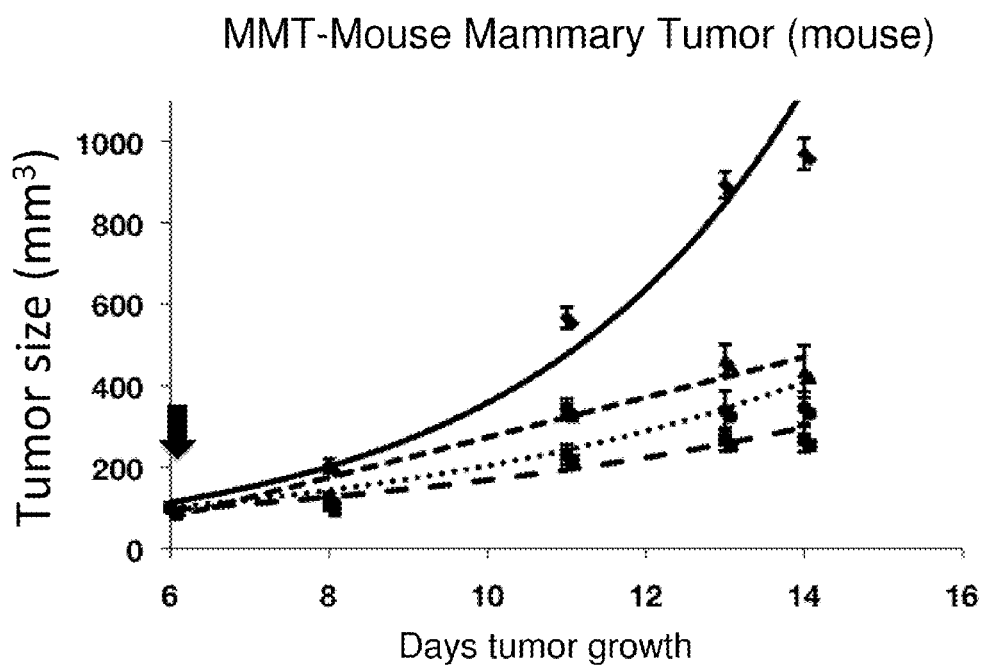

Similar experiments to Example 7 above were conducted with SCID mice implanted with human A673-Rhabdomyosarcoma ($2.5\times10^6$ cells/mouse), mouse Lewis lung carcinoma ($1\times10^6$ cells/mouse), or mouse mammary tumor (MMT) ($1\times10^6$ cells/mouse). The results are shown in FIGS. 8-10, respectively.

The results from Examples 5-8 above indicate that although VEGF inhibitors and Dll4 inhibitors have very different effects on tumor vascular morphology, they can both reduce tumor perfusion as well as tumor growth. Furthermore, the combination of VEGF inhibitors and Dll4 inhibitors appears more effective than either single agent, clearly exhibiting synergistic effects. Such synergistic effects were observed in both VEGF-blockade-resistant tumors and Dll4-Notch-blockade-resistant tumors. Thus, the combination therapy using Dll4 antagonists and VEGF antagonists are especially useful in treating cancer or tumors that have failed to respond to, or are known to be resistant to, either or both of Dll4-Notch and VEGF blockades when applied independently of each other. These studies begin to provide a mechanistic link between the acute functional vascular effects of anti-angiogenic treatments and their effects on tumor growth.

What is claimed is:

1. A method for treating a tumor or cancer that is resistant to vascular endothelial growth factor (VEGF) inhibition or delta-like ligand 4 (Dll4) inhibition, or both, comprising administering to a subject in need thereof an effective amount of a Dll4 antagonist in combination with an effective amount of a VEGF antagonist, wherein the Dll4 antagonist comprises the amino acid sequence of SEQ ID NO:22, and the VEGF antagonist comprises the amino acid sequence of SEQ ID NO:19.

2. The therapeutic method of claim 1, wherein the Dll4 antagonist and the VEGF antagonist are concurrently administered.

3. The therapeutic method of claim 1, wherein the Dll4 antagonist and the VEGF antagonist are sequentially administered.

4. A method for treating a tumor or cancer that is resistant to vascular endothelial growth factor (VEGF) inhibition or delta-like ligand 4 (Dll4) inhibition, or both, comprising administering to a subject in need thereof an effective amount of a Dll4 antagonist in combination with an effective amount of a VEGF antagonist, wherein the Dll4 antagonist comprises the amino acid sequence of SEQ ID NO:30, and the VEGF antagonist comprises the amino acid sequence of SEQ ID NO:19.

5. The therapeutic method of claim 4, wherein the Dll4 antagonist and the VEGF antagonist are concurrently administered.

6. The therapeutic method of claim 4, wherein the Dll4 antagonist and the VEGF antagonist are sequentially administered.

* * * * *